(12) United States Patent
Bender et al.

(10) Patent No.: US 11,013,819 B2
(45) Date of Patent: May 25, 2021

(54) CHLORINE DIOXIDE DECONTAMINATION SYSTEM AND METHODS

(71) Applicant: Controlled Performance with Gases, LLC, Louisville, KY (US)

(72) Inventors: Lawrence F. Bender, Louisville, KY (US); James F. Knoer, Taylorsville, KY (US)

(73) Assignee: Controlled Performance with Gases, LLC, Louisville, KY (US)

( * ) Notice: Subject to any disclaimer, the term of this patent is extended or adjusted under 35 U.S.C. 154(b) by 490 days.

(21) Appl. No.: 15/899,309

(22) Filed: Feb. 19, 2018

(65) Prior Publication Data

US 2018/0177905 A1  Jun. 28, 2018

Related U.S. Application Data

(63) Continuation-in-part of application No. 15/832,388, filed on Dec. 5, 2017, now Pat. No. 10,596,284, which is a continuation-in-part of application No. 14/837,017, filed on Aug. 27, 2015, now Pat. No. 9,943,620.

(Continued)

(51) Int. Cl.
*A61L 2/20* (2006.01)
*A61L 9/12* (2006.01)
*C01B 11/02* (2006.01)

(52) U.S. Cl.
CPC ............... *A61L 2/20* (2013.01); *A61L 9/122* (2013.01); *C01B 11/022* (2013.01); *A61L 2202/11* (2013.01); *A61L 2202/121* (2013.01); *A61L 2202/122* (2013.01); *A61L 2202/13* (2013.01); *A61L 2202/14* (2013.01); *A61L 2202/15* (2013.01); *A61L 2202/16* (2013.01); *A61L 2202/24* (2013.01); *A61L 2202/25* (2013.01); *A61L 2209/111* (2013.01);

(Continued)

(58) Field of Classification Search
CPC .......... A61L 2/20; A61L 9/122; C01B 11/022
See application file for complete search history.

(56) References Cited

U.S. PATENT DOCUMENTS

| 5,597,645 | A | 1/1997 | Pike | |
| 5,906,794 | A * | 5/1999 | Childers | G05D 27/02 422/111 |

(Continued)

OTHER PUBLICATIONS

PCT International Search Report and Written Opinion for PCT/US15/47091; Printed Jul. 12, 2016.

*Primary Examiner* — Kevin Joyner
(74) *Attorney, Agent, or Firm* — Neustel Law Offices

(57) ABSTRACT

A scalable, portable and modular chlorine dioxide fumigant decontamination system having an activating area and a neutralizing area which may be housed separately or as a single operationally connected unit, and which may be configured as a closed loop system connected to a decontamination chamber for decontamination of articles, or as an open loop system for decontamination of interiors and large confined spaces, and employing a specialized activating cup that is permeable to air yet substantially impermeable to water and chlorine dioxide reaction by-products such that directing air through the activation cup releases nearly pure chlorine dioxide fumigant. Methods and articles relating to the system are also described.

20 Claims, 24 Drawing Sheets

Related U.S. Application Data

(60) Provisional application No. 62/042,398, filed on Aug. 27, 2014.

(52) U.S. Cl.
CPC ..... *A61L 2209/134* (2013.01); *A61L 2209/14* (2013.01); *A61L 2209/16* (2013.01)

(56) References Cited

U.S. PATENT DOCUMENTS

| | | |
|---|---|---|
| 6,607,696 B1 | 8/2003 | Hamilton |
| 8,524,167 B2 | 9/2013 | Regits |
| 2003/0133834 A1 | 7/2003 | Karle |
| 2004/0022673 A1 | 2/2004 | Protic |
| 2004/0211731 A1 | 10/2004 | Ferguson |
| 2006/0110280 A1 | 5/2006 | Nelson |
| 2008/0025870 A1 | 1/2008 | Groenewegen |
| 2010/0266448 A1 | 10/2010 | Regits |
| 2012/0164025 A1 | 6/2012 | Stockley, III |
| 2013/0101477 A1 | 4/2013 | Both |
| 2013/0216437 A1 | 8/2013 | Sperry |
| 2016/0206767 A1 | 7/2016 | Park |

\* cited by examiner

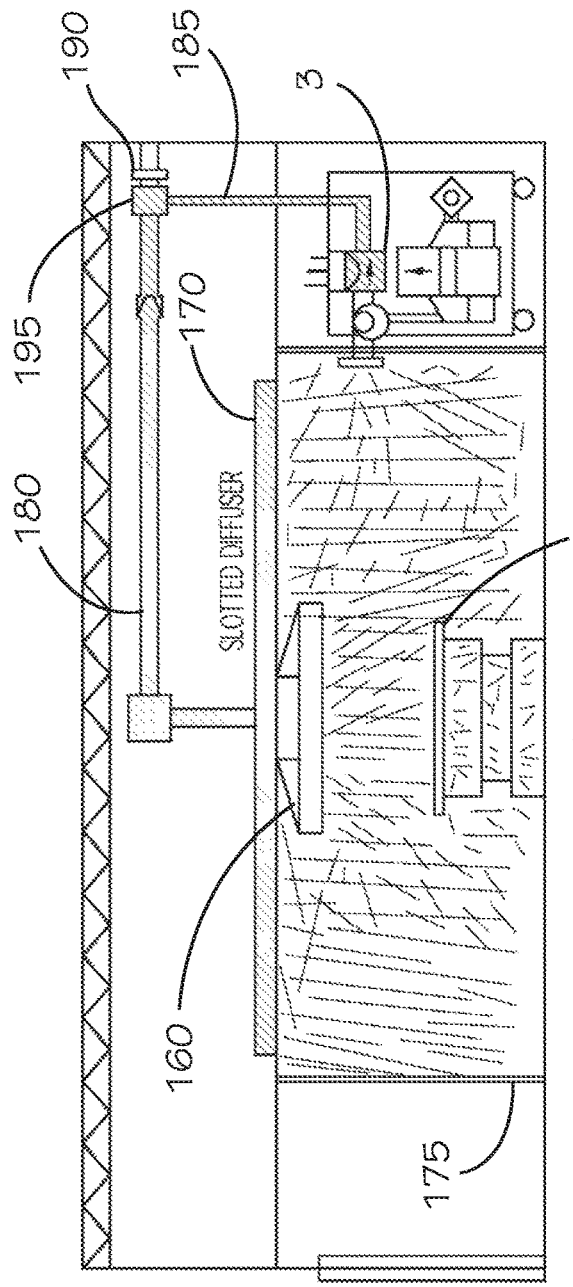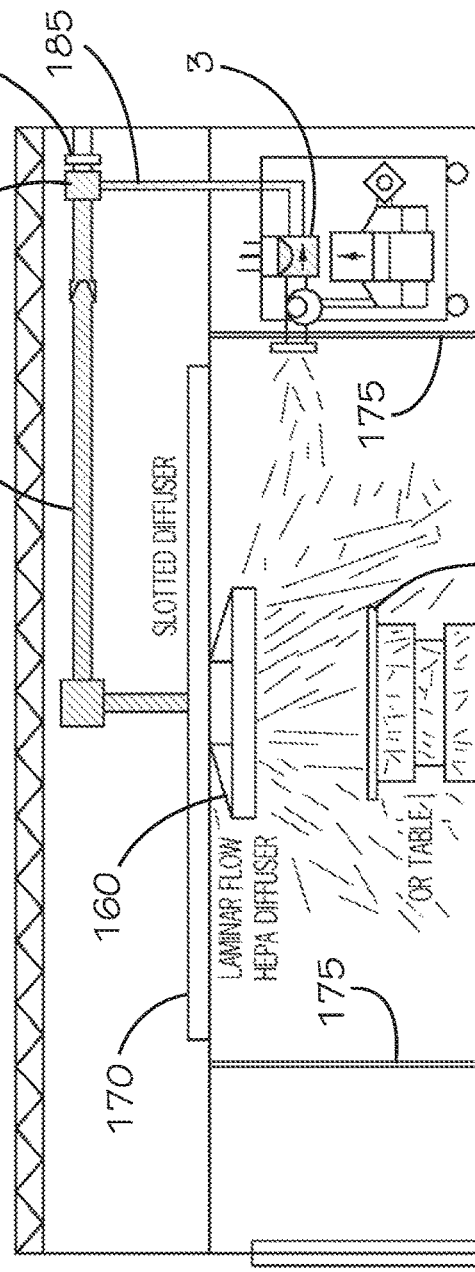

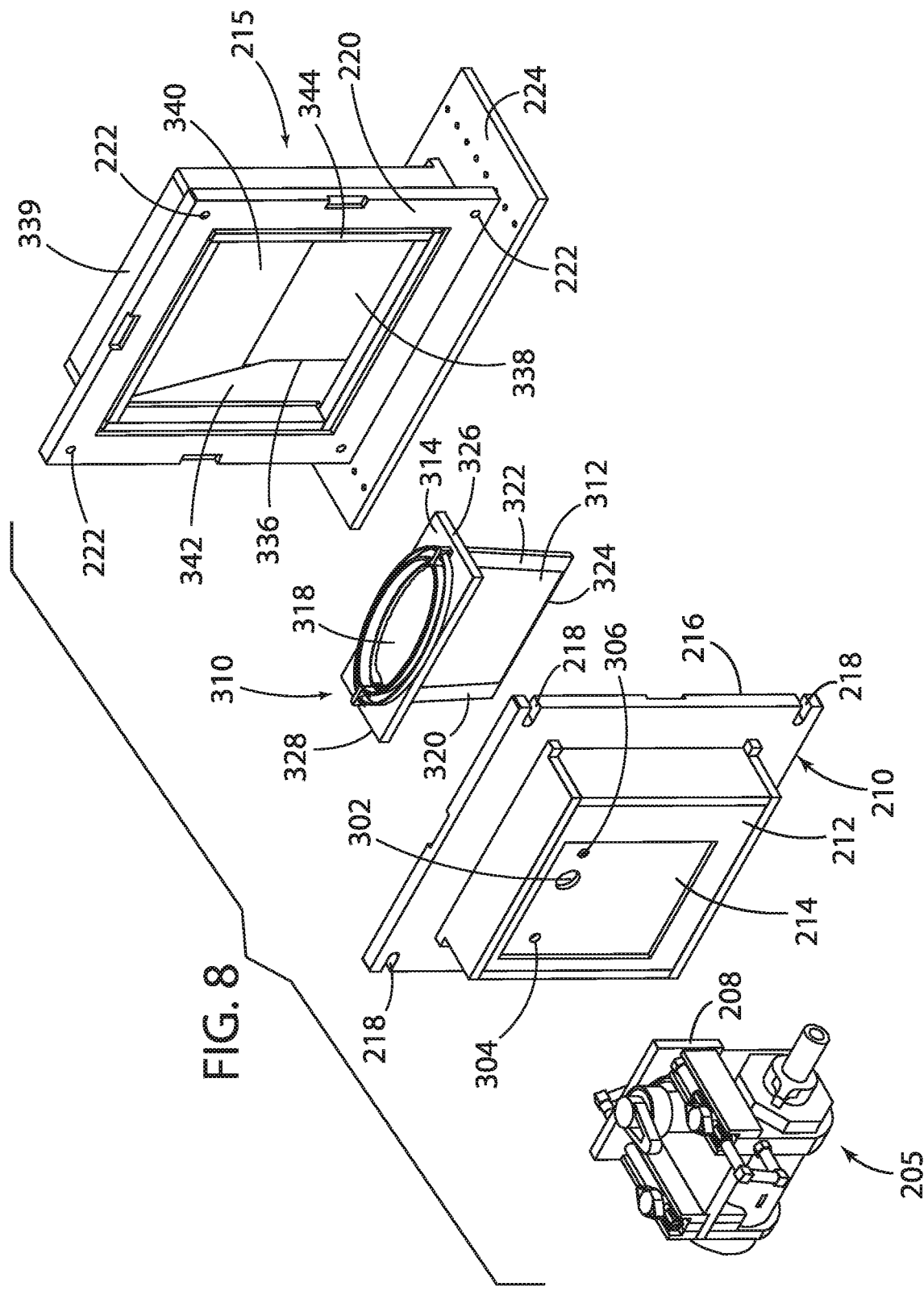

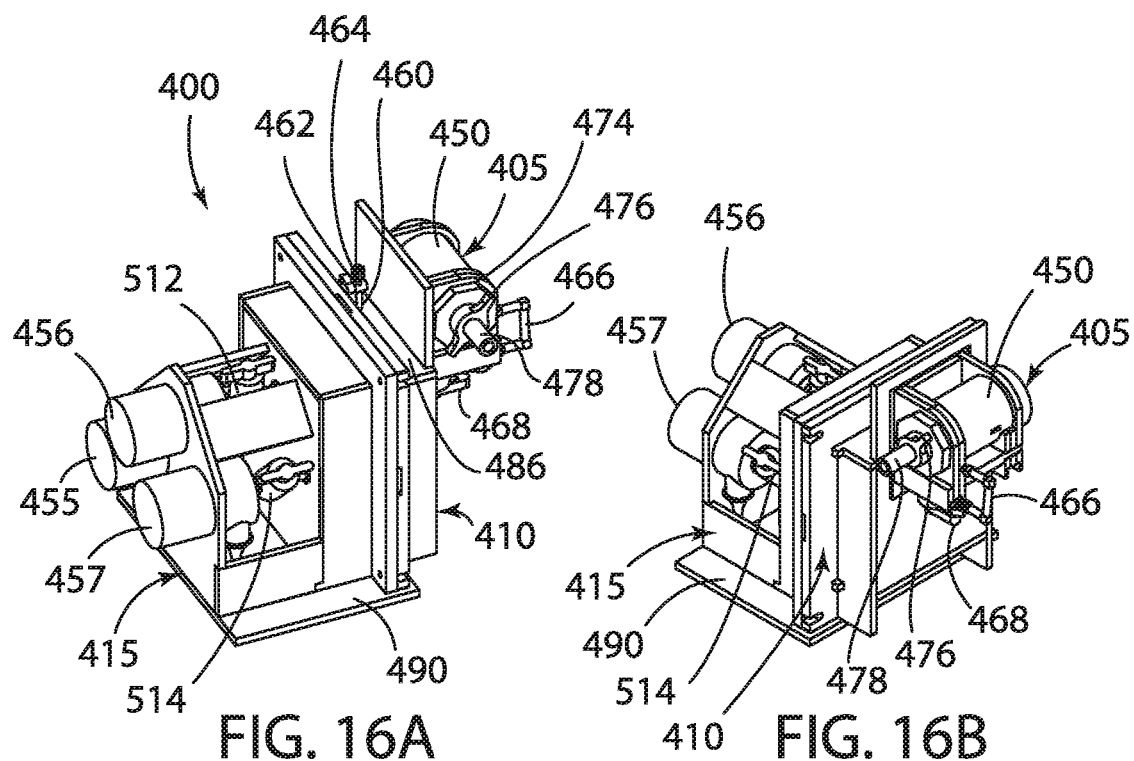
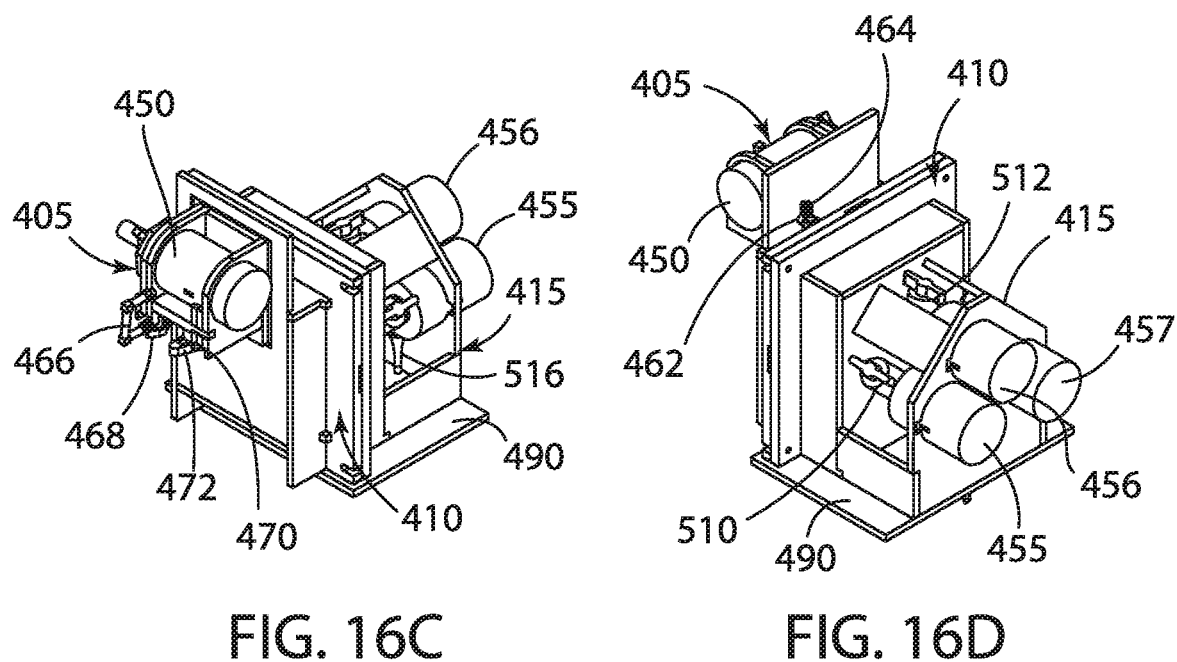
FIG. 16A  FIG. 16B  FIG. 16C  FIG. 16D

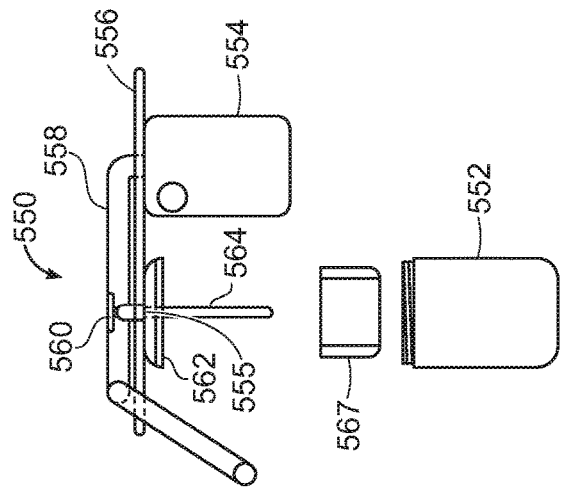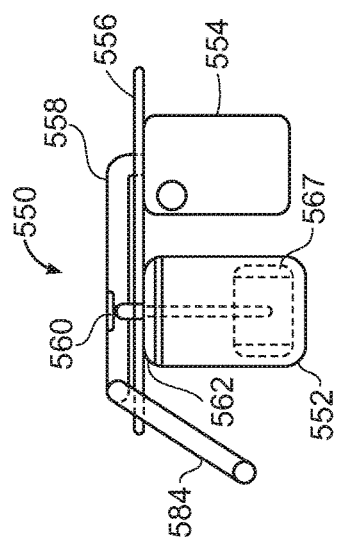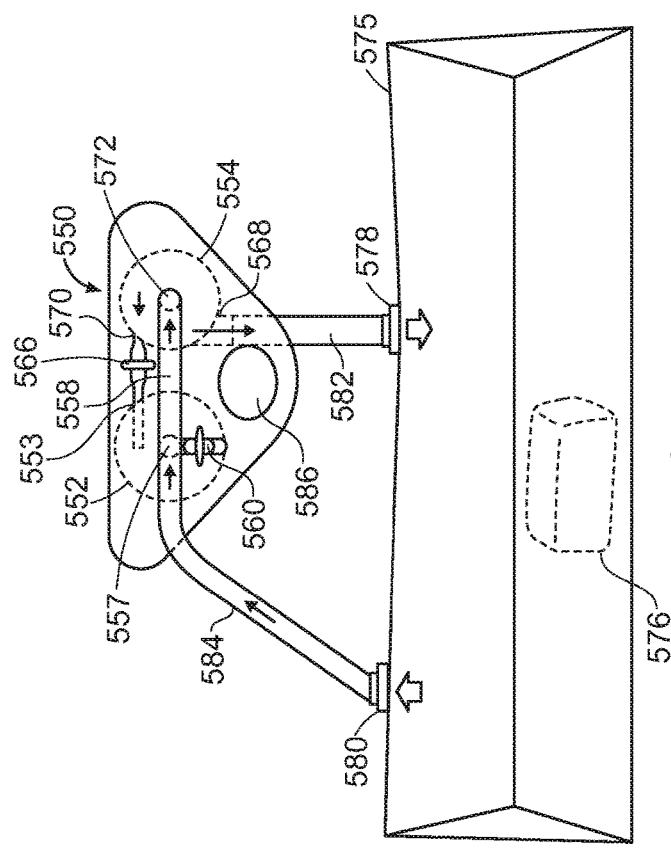

CHLORINE DIOXIDE DECONTAMINATION SYSTEM AND METHODS

CROSS REFERENCE TO RELATED APPLICATIONS

The present application is a continuation-in-part of U.S. application Ser. No. 15/832,388 filed on Dec. 5, 2017, which is a continuation-in-part of U.S. application Ser. No. 14/837,017 filed on Aug. 27, 2015, which claims priority to U.S. Provisional Application No. 62/042,398 filed Aug. 27, 2014. Each of the aforementioned patent applications, and any applications related thereto, is herein incorporated by reference in their entirety.

STATEMENT REGARDING FEDERALLY SPONSORED RESEARCH OR DEVELOPMENT

Not applicable to this application.

BACKGROUND

Field

Example embodiments in general relate to a chlorine-dioxide fumigant based decontamination system and method.

Related Art

Any discussion of the related art throughout the specification should in no way be considered as an admission that such related art is widely known or forms part of common general knowledge in the field.

Chlorine dioxide (CD or $ClO_2$) was discovered in the early 1800's, and has been approved for a wide variety of commercial disinfecting/sterilizing applications by the EPA, FDA and USDA. Due to its demonstrated efficacy with respect to a wide variety of contaminated surfaces, $ClO_2$ has been called the ideal biocide and the ability of chlorine dioxide to reduce or eliminate microbes, e.g., bacteria, viruses, fungi, mold spores, algae and protozoa, at relatively low concentrations is well-documented. Because $ClO_2$ inactivates microorganisms by oxidizing critical components of a microorganism's membrane proteins, tolerance to $ClO_2$ does not develop, making it an ideal disinfectant/sterilant for repeated-use applications such as in a hospital environment.

$ClO_2$ is a green-yellowish gas with a chlorine-like odor; however $ClO_2$ is a neutral chlorine compound. $ClO_2$ is a small, volatile and very strong molecule. In diluted, watery solutions $ClO_2$ is a free radical. At high concentrations it reacts strongly with reducing agents. Chlorine dioxide is an unstable gas that dissociates into chlorine gas and oxygen gas readily. Further, $ClO_2$ may be photo-oxidized by sunlight and therefore decontamination applications generally proceed in the absence of light. The end-products of $ClO_2$ neutralization/degradation reactions are chloride (Cl—), chlorite (ClO—) and chlorate ($ClO_3$—).

$ClO_2$ is not as reactive as ozone or chlorine and it generally reacts only with sulphuric substances, amines and some other reactive organic substances. In comparison to chlorine and ozone, less chlorine dioxide is required to obtain an active residual disinfectant. It can also be used when a large amount of organic matter is present in the environment.

A significant drawback of $ClO_2$ is that it is explosive under pressure, thus making it difficult to transport. It cannot be transported in liquid phase or under pressure; hence it is typically manufactured on site (in situ). $ClO_2$ is usually produced as a watery solution or gas. It is produced in acidic solutions of sodium chlorite ($NaClO_2$), or sodium chlorate ($NaClO_3$). Sodium chlorite, chlorine gas ($Cl_2$), sodium hydrogen chlorite ($NaHClO_2$) and sulphuric or hydrogen acid are typically used for the production of chlorine dioxide on site. In the presence of sunlight, $ClO_2$ in air will decompose to chlorine and oxygen. The chlorine will react with any moisture in the air to form a hydrochloric acid mist. If the concentration of $ClO_2$ in air in a confined space is above 10%, the chlorine dioxide is at an explosive concentration and can be ignited by almost any form of energy such as sunlight, heat or sparks, including for example, static electrical energy. Concentrations above 40% will generate a decomposition/shock wave if set off by any ignition source.

Other decontamination systems which exploit the beneficial properties of $ClO_2$ fumigant are known in the art. However, these systems generally suffer from production of excess humidity with the fumigant, resulting in production of hydrochloric acid mist and potential to corrode electronic equipment, making the system inconvenient for large-scale building decontamination, since removal of corrosion-sensitive articles must be effectuated prior to decontamination. Further, even when corrosion-sensitive articles are removed from the area, metallic structural components of buildings may be affected. In addition to the corrosive effects of moisture, salts existing as by-products of $ClO_2$ generation reactions and often present in the fumigant, are known to cause damage to structures and articles undergoing decontamination. This is particularly problematic to areas that must be repeatedly disinfected, such as in the medical/hospital context, since the damaging effects accrue.

U.S. Pat. No. 8,524,167 (the '167 patent) discloses a $ClO_2$ decontamination system, however it suffers from failure to provide mechanisms for removal of byproducts and relies on humidification as a necessary aspect of effective $ClO_2$ fumigant decontamination, going so far as to add a humidifier to a decontamination chamber. The '167 patent system is unsuitable for corrosion-sensitive articles and environments. A critical consideration is that that the registered concentration of $ClO_2$ cannot be trusted, since chlorine gas is known to influence the sensors toward detection of chlorine dioxide and to result in artificially high concentration read-outs. Chlorine gas is produced as a result of the humidification. Further, the '167 fumigant scrubber relies heavily on carbon, which is rendered less effective by the presence of water. Notably, the use of carbon filtration with non-degraded $ClO_2$ can create an explosive potential because $ClO_2$ can build up in the carbon pores in problematic concentrations. Hence, the use of carbon as a primary neutralizer/scrubber presents a significant fire and safety hazard.

Known $ClO_2$ fumigant systems generally utilize a reaction sachet (bag) for generation of the gas with water, and sparging of the gas product from the liquid. The result is that acid vapor and chlorine gas are often present in the CD fumigant. As noted, both of these gases are highly corrosive to metals, and chlorine, in particular, is incompatible with many non-metallic substances as well. Neutralization of the fumigant is complicated by the presence of these additional toxic gases. Prolonged treatment time results where multiple passes are required for neutralization.

U.S. Pat. App. Pub. No. US 2012/0164025A1 discloses a package and method for disinfecting microbiologically contaminated products using a $ClO_2$ gas generating sachet. A predetermined volume of reactants for generating and neutralizing the $ClO_2$ disinfectant gas are pre-sealed within the gas generating sachet and separated by a frangible seal. A product to be disinfected is inserted into a package with the sachet and the package is sealed. The gas generation sachet is then physically activated by manually breaking the frangible seal. After a period of time, the package is unsealed and the product removed. In addition to the other shortcomings related to sachet-based gas generation systems noted above, pre-packaged gas generation sachets and disinfection methods employing them suffer from a lack of flexibility and control over the disinfection process. Both the length of the process and the concentration of disinfection gas are predetermined by the volume and amount of the reactants pre-sealed in the gas generating sachet. Thus, both the required concentration of disinfecting gas and the required disinfection time must be estimated in advance. Because it is not possible to terminate or otherwise control or adjust the disinfection process once it is underway, if the advance estimates are wrong, more disinfection than necessary may take place with an attendant waste of time, money, and chemicals, or insufficient disinfection may take place and require additional disinfection cycles.

In a highly publicized recent decontamination effort by the U.S. government, a $ClO_2$ fumigant system was employed to decontaminate a building contaminated with Anthrax spores that were released from a letter opened in a mail room. The building was tented prior to fumigation and sparged $ClO_2$ gas was pumped into the building's heating, ventilating and air conditioning (HVAC) system to achieve a target concentration of 500 ppm at 75° F. and 75% relative humidity for 18 hours. Biological indicators (BI) comprising standard *B. subtilus* spore strips were placed throughout the facility. (Standard BIs contain 106 natural pathogens—sufficient to indicate a maximum 6-log spore reduction, however the BI's were not normed to Anthrax). Hence the effectiveness of decontamination was also tested via swipe sampling. Reportedly, the original plan to neutralize the $ClO_2$ with ascorbic acid was abandoned when very high concentrations of chlorine gas were found localized throughout the building. Because the presence of chlorine molecules interferes with $ClO_2$ monitoring to yield false high concentration readings, it was presumed therefore that concentration targets were not actually met and the procedure had to be repeated three times over 9 months for a total cost of nearly 50 million dollars to U.S. taxpayers.

Clearly there remains a need in the art for safe and effective $ClO_2$ fumigant decontamination systems that minimize the use of water, minimize agitation/degradation of the CD fumigant, and that avoid dispersal of water vapor, acid and chlorine gas along with the fumigant. In addition, there remains a need for such systems that provide flexibility and control over the decontamination process while it is underway. There also is a need for such systems that are adapted not only for decontaminating large objects and spaces, such as buildings and rooms, but also for disinfecting and sterilizing small objects and spaces, such as medical instruments enclosed within sealed packages. Moreover, there remains a need for a system that can provide assurance a sterilized item remains sterilized even after repeated handling, moves, and changes in chain of custody.

SUMMARY

Example embodiments are directed to a chlorine dioxide decontamination system and method. The present investigators have developed a $ClO_2$ fumigant decontamination system and method that overcomes the foregoing and other deficiencies in the art. In particular, the disclosed system provides a $ClO_2$ fumigant that is substantially free of water vapor, acid vapors and other by-products of $ClO_2$ gas production. Thus, the $ClO_2$ decontamination system may be utilized in a broad range of applications, including for example, sterilization of corrosion-sensitive electronic equipment and metallic substrates, sterilization of environments for human habitation, and sterilization of operating rooms, medical devices, and other environments/devices that may be subject to repeated sterilization. Further, the $ClO_2$ fumigant decontamination system provides an aspect of one-pass neutralization, simplifying and decreasing the expense and time associated with large-scale decontamination projects generally. The system is modular and portable, offering not only increased convenience, but the operational capacity to locate additional $ClO_2$ fumigant activating areas throughout a large area to be decontaminated dependent on target concentrations and area to be decontaminated. The system also provides flexibility and control over the decontamination process while it is underway. Still further, the system is adapted to provide not only decontamination of large objects and spaces, but also sterilization of small objects, including objects enclosed in sealed packages and the openings and internal channels and spaces within such objects. Still further, the system provides assurance an item once sterilized remains sterile even after repeated handling, movement, and changes in chain of custody.

One embodiment of the invention provides decontamination systems comprising: a chlorine dioxide ($ClO_2$) fumigant activating area, optionally, a by-pass flow area, and a neutralizing area; a first air blower, preferably having variable speed and in direct fluid communication with the $ClO_2$ fumigant activating area, the by-pass flow area and the neutralizing area; and a valve system for dedicating air flow from the blower to one or more of the areas. The activating area comprises a novel activation cup configured to receive reagents for the in situ generation of $ClO_2$ fumigant. The activation cup is fabricated to be permeable to air and substantially impermeable to water and reaction by-products. The activation cup may be positioned or located in the activation area such that air flowing from the first variable speed air blower into the activation area flows through and around the activation cup such that generated $ClO_2$ fumigant passes out of the activation cup with the air flow, while water and reaction by-products remain in the activation cup. Thus, $ClO_2$ fumigant produced according to the inventive decontamination system is substantially free of water vapor, acid vapor and chlorine gas.

Another embodiment of the invention provides a $ClO_2$ fumigant activation unit comprising an activator, an activation chamber containing an open-top activation pouch, and an adjustable back plate adapted for interfacing the activation unit directly to a vent of an HVAC or similar air distribution system in a plurality of selectable orientations. The activator comprises conduits and valves for selectively delivering reagents and water into the activation pouch within the activation chamber to generate $ClO_2$ gas in situ, and an air blower to direct $ClO_2$ fumigant from the activation chamber through the adjustable back plate into a vent of an HVAC or similar air distribution system. The activator also is operable to selectively deliver neutralizing reagents into the activation pouch and to recirculate air between the activation unit and the HVAC or similar system in order to halt the further generation of $ClO_2$ fumigant and to neutralize any $ClO_2$ fumigant remaining in the system. In certain variations of the embodiment, the adjustable portion of the back plate is not necessary and the activation unit can be mounted directly to a surface defining a window opening, duct opening, or other opening.

Yet another embodiment of the invention provides a system adapted for sterilizing items contained within sealed packages and comprises a $ClO_2$ fumigant activation unit comprising an activator, an activation chamber containing an improved open-top activation pouch, and a back plate adapted for interfacing the activation unit to an item to be sterilized enclosed within a sealed package. The activator comprises valves and conduits for selectively delivering reagents and water into the activation pouch within the activation chamber to generate $ClO_2$ gas in situ, and an air blower to direct $ClO_2$ fumigant from the activation chamber into a back plate. The back plate may be provided with one or more blowers and corresponding valves and conduits to selectively direct $ClO_2$ fumigant directly to an item to be sterilized within a sealed package. The activator also is operable to selectively deliver neutralizing reagents into the activation pouch and to recirculate air between the activation chamber and the sealed package to halt the generation of additional $ClO_2$ gas and to neutralize remaining $ClO_2$ fumigant within the package. In another embodiment, the back plate is adapted to interface the fumigant activation unit to a sealed enclosure containing a sealed package so that the sealed package itself also may be sterilized.

Still another embodiment of the invention provides a compact portable sterilization system for sterilizing an item contained in a sealed package, comprising an open top activator housing adapted to receive water and reagents to generate $ClO_2$ fumigant, a flexible sealable substantially gas impermeable package adapted to contain an item to be sterilized, and an air/gas blower adapted to create a flow of air/gas. The activator housing, air/gas blower and flexible package are connected by air/gas conduits in a closed-loop configuration such that when $ClO_2$ gas is generated in the activator housing and the air/gas blower is activated, $ClO_2$ fumigant circulates through the closed loop to fill the flexible package and sterilize the item contained therein.

Other embodiments provide methods for generating chlorine dioxide fumigant in a directed flow with a minimum of water. The methods comprise (a) providing an activation cup comprising: an outer layer of crush-resistant thermally bondable non-woven fibers molded into a transversely bisected aerodynamically-shaped shell, said shell open at the top and having an interior surface and an exterior surface, said exterior surface and interior surface comprising a pattern of corrugations; at least one filter layer including one filter layer adjacent and adherent to an inner surface of the outer layer, wherein at least one filter layer comprises high-loft electret charged fluorine-coated polyolefin microfibers, wherein the activation cup is adapted to retain water and reaction by-products while permitting gas to pass through; (b) flexibly suspending the activation cup; (c) adding dry reagents for production of $ClO_2$ fumigant to the cup; (d) directing an air flow toward the cup at a low speed such that the corrugations create turbulence resulting in vibration of the cup and acceleration of $ClO_2$ generation, "low" being defined as insufficient to degrade $ClO_2$; (e) adding water to the cup; thereby initiating generation of $ClO_2$ fumigant that is directed out of the cup with the air flow while water and $ClO_2$ generation reaction by-products are substantially retained in the cup.

Still other embodiments provide similar methods for generating $ClO_2$ fumigant gas in situ employing an improved open pouch which can be constructed of essentially the same material as the previously referred to activation cup. Similarly, embodiments for methods for neutralizing $ClO_2$ fumigant gas employing such an improved open pouch are provided.

Further embodiments provide methods for neutralizing chlorine dioxide ($ClO_2$) fumigant in a sealed neutralizing area, said neutralizing area comprising a leak abatement space and a neutralizing space, said neutralizing space comprising a series of treatment stations and at least one blower, the method comprising: (a) blowing $ClO_2$ fumigant to-be-neutralized into a treatment station comprising ultraviolet light, resulting in partially neutralized air, said blowing effectuated at a speed high enough to degrade $ClO_2$; (b) blowing the partially neutralized air from the UV treatment station through a diffusion plate and into a treatment station comprising a neutralizing solution reservoir, thereby creating bubbling and frothing in the reservoir and resulting in substantially neutralized air; (c) capturing and returning solution to the reservoir with a treatment station comprising a humidification filter that permits the substantially neutralized air to pass through the filter and into a treatment area comprising coated zeolite; (d) passing the substantially neutralized air through the coated zeolite to neutralize any remaining $ClO_2$ and other toxic gaseous by-products remaining, resulting in neutralized air; and, (e) optionally, passing the neutralized air through activated carbon to remove odiferous molecules which may be present in the neutralized air.

Embodiments directed to a fumigant activation cup are also disclosed. The cup comprises (a) an outer layer of crush-resistant thermally bondable non-woven fiber molded into a transversely bisected aerodynamically-shaped shell, said shell open at the top and having an interior surface and exterior surface; (b) at least one filter layer, including one filter layer adherent and adjacent to an inner surface of the outer molded layer; (c) an inner layer of crush-resistant fibrous material adjacent and adherent to the at least one filter layer; wherein the at least one filter layer comprises high-loft electrically charged fluorinated polyolefin microfibers and exhibits a higher melting point than the molded layers.

Other embodiments directed to an improved $ClO_2$ fumigant activation pouch are also disclosed. The improved fumigant activation pouch comprises essentially the same materials as described above with respect to the fumigant activation cup. In one variation, the pouch comprises a body of a unitary piece of material with opposing first and second sides that are sealed at their corresponding outer edges to define an open top and an enclosed bottom comprising a fold in the material. In another variation, the pouch may be formed of multiple discrete pieces of material overlaid, sealed on the sides, cut to a desired length, and then sealed on the bottom while leaving the top open. A substantially flat pouch retaining plate has an opening adapted to receive and retain the pouch while expanding the open top to facilitate receipt of reagents and water. The facing sides of the pouch are preferably substantially trapezoid-shaped and taper from the open top to the closed bottom to facilitate entry of the pouch in the opening of the retaining plate while retaining the pouch and expanding the open top of the pouch. However, other shapes, such as squares, rectangles, and cones are contemplated depending on the particular application and design of the embodiment. A flexible retention ring may be secured to the pouch near the open end and used to securely retain the top of the pouch in the retention plate opening, as well as to hang or suspend the pouch in a desired position or location in an activation chamber.

There has thus been outlined, rather broadly, some of the embodiments of the chlorine dioxide decontamination system and methods in order that the detailed description thereof may be better understood, and in order that the present contribution to the art may be better appreciated. There are additional embodiments of the chlorine dioxide decontamination system and methods that will be described hereinafter and that will form the subject matter of the claims appended hereto. In this respect, before explaining at least one embodiment of the chlorine dioxide decontamination system and methods in detail, it is to be understood that the chlorine dioxide decontamination system and methods is not limited in its application to the details of construction or to the arrangements of the components set forth in the following description or illustrated in the drawings. The chlorine dioxide decontamination system and methods is capable of other embodiments and of being practiced and carried out in various ways. Also, it is to be understood that the phraseology and terminology employed herein are for the purpose of the description and should not be regarded as limiting.

BRIEF DESCRIPTION OF THE DRAWINGS

Example embodiments will become more fully understood from the detailed description given herein below and the accompanying drawings, wherein like elements are represented by like reference characters, which are given by way of illustration only and thus are not limitative of the example embodiments herein.

FIG. 5D shows the fumigant diffused into the operating room and contained within the air curtain.

FIG. 5E shows the fumigant directed into the decontamination system where it may be neutralized or re-circulated depending on valve manipulation and need.

FIG. 8 is an exploded perspective view of a $ClO_2$ fumigant activation unit according to an example embodiment.

FIGS. 16A-16D are perspective views from several angles of a fumigant activation unit of a $ClO_2$ sterilization system according to an example embodiment.

FIG. 21 is a side view of a fumigant activation unit of a $ClO_2$ sterilization system according to an example embodiment.

FIG. 22 is an exploded side view of a fumigant activation unit of a $ClO_2$ sterilization system according to an example embodiment.

FIG. 23 is a top plan view of a $ClO_2$ sterilization system according to an example embodiment connected by conduits to a sealed package.

DETAILED DESCRIPTION

Figure 1:
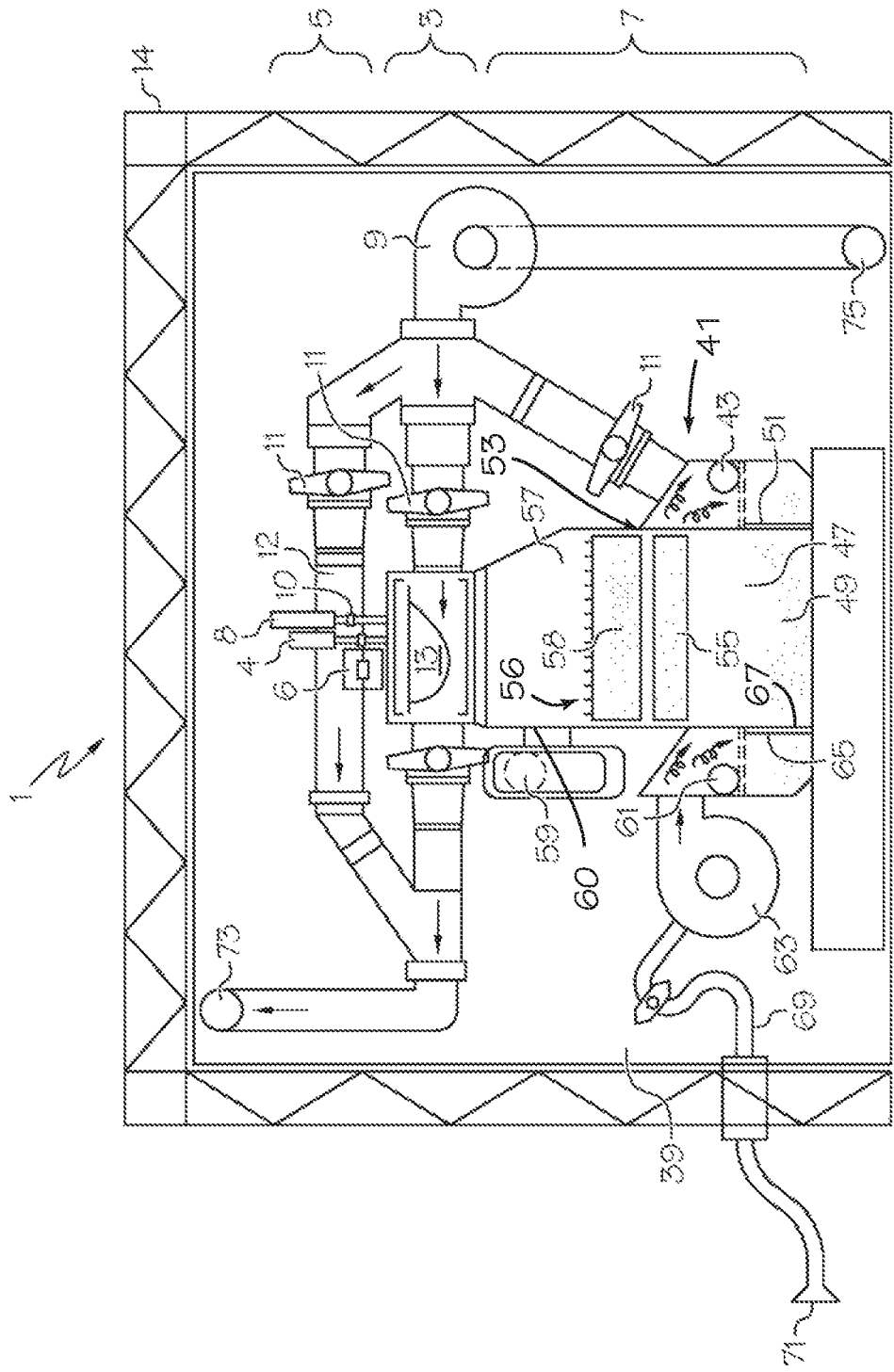
FIG. 1 depicts a cross-sectional schematic view of an exemplary combined activating area, bypass area, and neutralizing area; all operationally connected and contained in a single cabinet.
Figure 2A:
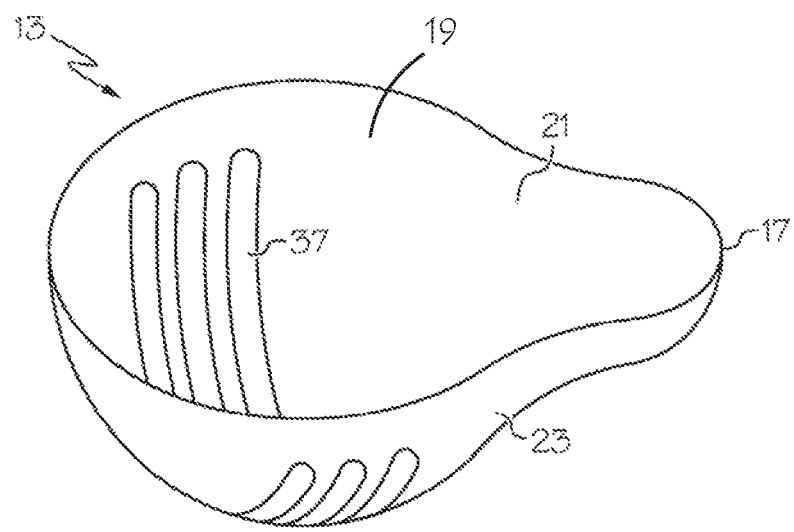
FIG. 2A shows an illustrative cup with a saddle-shaped horizontal cross-sectional shape.
Figure 2B:
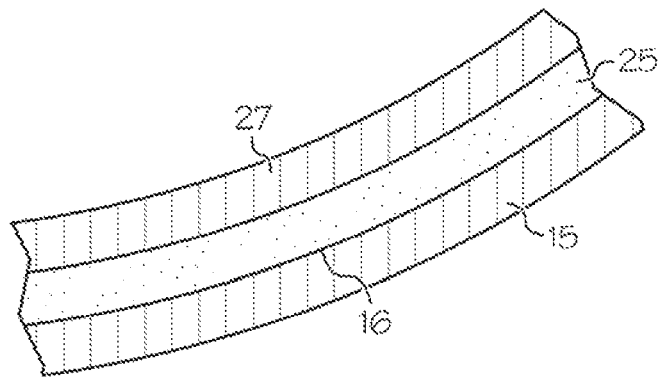
FIG. 2B shows a schematic cross-section of a thickness of an edge of the cup illustrating a filter layer disposed between two molded layers.
Figure 2C:
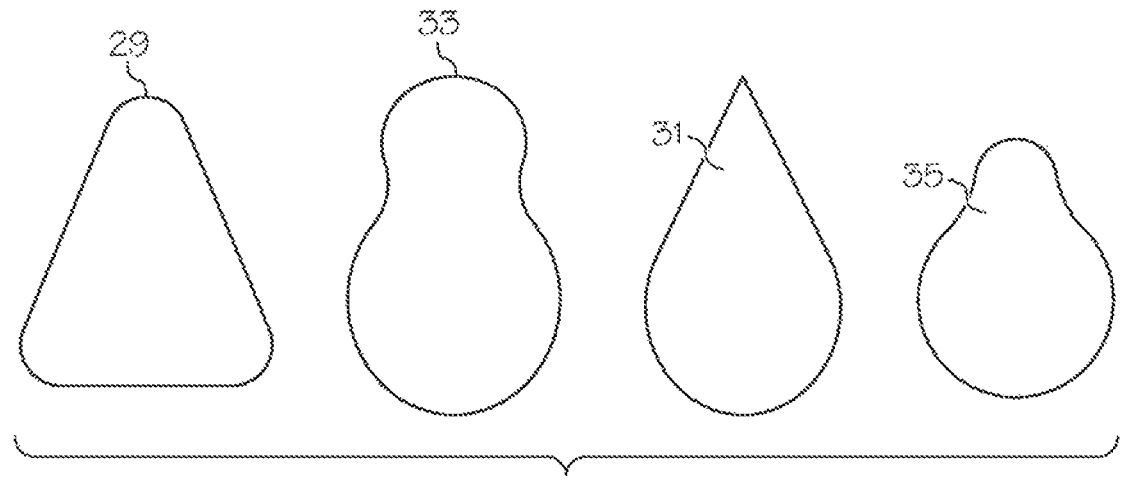
FIG. 2C illustrates several shapes suitable as the aerodynamic horizontal cross-sectional shape of the top perimeter of an activating cup.

When describing example embodiments of the system and methods of the invention, the term decontamination may be used to refer to all levels of sanitizing, sterilizing, disinfecting and deodorizing. Decontamination is a term used broadly to describe a process or treatment that renders a medical device, instrument, surface, content, or environmental surface safe for humans. Decontamination includes sterilization and disinfection. Disinfection eliminates virtually all pathogenic non-spore-forming microorganisms but not necessarily all microbial forms on inanimate objects (work surfaces, equipment, etc.). Effectiveness is influenced by the kinds and numbers of organisms, the amount of organic matter, the object to be disinfected and chemical exposure time, temperature and concentration. The CDC recognizes three levels of disinfection: (1) High-level Disinfection: A procedure that kills all organisms with the exception of bacterial spores and certain species, such as the Creutzfeldt-Jakob prion. Most high-level disinfectants can produce sterilization with sufficient contact time. (2) Intermediate-level Disinfection: A procedure that kills vegetative bacteria, including acid-fast *Mycobacterium tuberculosis*, most fungi, and viruses but not bacterial spores. (3) Low-level Disinfection: A procedure that kills most vegetative bacteria (but not *M tuberculosis*), some fungi, and viruses but no spores. Sterilization is destruction all microbial life, including highly resistant bacterial endospores.

A. Overview

An example embodiment of the novel $ClO_2$ decontamination system and method as described herein generally comprises a specialized activation area, a by-pass flow area, and a neutralizing area contained in a sealed portable cabinet. A specially constructed activation cup suspended in the activation area receives reagents and a small amount of water to generate $ClO_2$ fumigant gas. Air flow is directed around and through the activation cup to provide target residential concentrations of $ClO_2$ to any desired area for the purpose of decontamination, disinfecting, sterilization, and deodorization. After a period of time, the $ClO_2$-containing air is drawn through the neutralizing area where it is treated and made suitable for release into the environment. In one example application, an example embodiment of the system is interfaced with a remote portable decontamination chamber. In another example application, an example embodiment of the system is interfaced with the local ductwork of an operating room to be decontaminated. In yet another example application, an example embodiment having multiple separately housed activation areas and a separately housed neutralizing area are interfaced to the air distribution ductwork of a central HVAC system of a building to be decontaminated.

Another example embodiment generally comprises a sealed fumigant activation unit including an activator, an activation chamber, and a back plate. A specially constructed activation pouch is located in the activation chamber. The activation pouch is adapted to contain a reaction solution of a $ClO_2$-generating reagent and water and to release generated $ClO_2$ gas into the activation chamber to produce a decontamination fumigant. The activator includes valves and conduits for selectively introducing a small amount of water into the activation pouch to initiate the $ClO_2$-generating reaction. The activator also is adapted to introduce a neutralizing solution into the pouch to stop the generation of $ClO_2$ gas and neutralize $ClO_2$ fumigant. The activator includes a blower operable to selectively direct a flow of air around and through the activation pouch and to direct a decontamination fumigant of air and generated $ClO_2$ gas from the activation chamber to the back plate. Alternatively, the blower is operable to recirculate $ClO_2$-containing air for neutralization. In one embodiment, the back plate is adjustable and is adapted for mounting the fumigant activation unit directly with a vent of an air distribution system of an HVAC or similar system in a plurality of selected orientations. In another embodiment, the back plate includes one or more air/gas blowers and valves for directing decontamination fumigant via conduits directly to the openings and internal passages of an item to be sterilized within a sealed package. In yet another embodiment, the back plate is adapted to interface the fumigant activation unit to a sealed enclosure containing a sealed package and item to be sterilized and is adapted to direct decontamination fumigant to both the interior and exterior of the sealed package.

Still another example embodiment comprises a compact portable sterilization system for sterilizing an item contained in a sealed package. A fumigant activation unit comprises an open top activator housing adapted to receive water and reagents to generate $ClO_2$ fumigant. The water and reagents can be introduced directly into the activator housing or indirectly via an open top pouch. An activator housing top enclosure attaches to seal the activator housing. An air/gas blower is connected to the activator housing via an air/gas conduit and is operable to create a flow of $ClO_2$ fumigant. The air/gas blower is also connected to an inlet of a flexible sealable substantially gas impermeable package via an air/gas conduit. The package contains an item to be sterilized. An outlet of the package is connected to an outlet of the activator housing. The activator housing, air/gas blower, and package are configured in a closed air/gas circulation loop so that when $ClO_2$ gas is generated in the activator housing and the air/gas blower is activated, $ClO_2$ fumigant circulates through the closed loop to fill the flexible package and sterilize the item. The fumigant activation unit is portable with the activator housing and air/gas blower being mounted to a portable mounting platform and the flexible package is disposable after use.

The components of the various example embodiments of the system operate in synchrony to achieve safe and highly efficient production of substantially pure $ClO_2$ fumigant. "Substantially pure" $ClO_2$ as used herein is defined as a gas that is between 90 and 99.9% $ClO_2$ by weight, or between 95 and 99.9% $ClO_2$ by weight, or between 98 and 99.5% $ClO_2$ by weight, or over 99% $ClO_2$ by weight.

The system according to the invention is versatile in that it can be configured and scaled for small, large and complex configurations and environmental applications. Components of the system may be separated and used independently or in multiples, depending on the decontamination environment and needs.

Example embodiments and aspects of the invention will be described with reference to the Figures, which are intended to be illustrative and not limiting of the scope of the invention as defined by the claims.

B. $ClO_2$ Decontamination System and Method

FIG. 1 sets forth an exemplary aspect of a decontamination system 1: a chlorine dioxide ($ClO_2$) fumigant activating area 3, a by-pass flow area 5, and a neutralizing area 7. A first variable speed air blower 9 is in direct fluid communication with the $ClO_2$ fumigant activating area 3, the by-pass flow area 5 and the neutralizing area 7. As illustrated, the activating, bypass and neutralizing areas may be housed in a single sealed container or "cabinet." Variable speed is advantageous in order to adapt the flow speed to particular decontamination needs and environmental sizes and configurations. Further, where the blower is directed to the activating area relatively low flow force may be desirable in order to avoid degrading the $ClO_2$ and producing chlorine gas; whereas when flow is directed to the neutralizing area higher speeds may be desired in order to promote degradation of the $ClO_2$. The system further comprises a valve system 11 for dedicating air flow from the blower 9 to one or more of the areas 3, 5, 7.

The activating area 3 comprises an activation cup 13 configured to receive reagents for in situ generation of $ClO_2$ fumigant. The activation cup 13 is permeable to air; yet substantially impermeable to water and reaction by-products. The activation cup is flexibly suspended in the activation area 3 such that air flowing from the first variable speed air blower 9 into the activation area flows through and around the activation cup such that generated $ClO_2$ fumigant passes out of the activation cup 13 with the air flow while water and reaction by-products remain in the activation cup 13.

C. Activation Cup

Referring now to FIGS. 2A and 2B, according to certain embodiments the activation cup 13 comprises: an outer layer 15 of crush-resistant thermally bondable non-woven fiber molded into a transversely bisected aerodynamically-shaped shell 17. The shell 17 is oriented in the activating area such that it is open at the top 19. As illustrated in FIG. 2B, the shell has an interior surface 21 and an exterior surface 23 and at least one filter layer 25 interposed between the molded outer layer 15 and a molded inner layer 27. At least one filter layer 25 is adjacent and adherent to an inner surface 16 of the outer molded layer 15. The cup also has an inner molded layer 27 of crush-resistant fibrous material that is adjacent and adherent to the at least one filter layer 25. The at least one filter layer 25 is fabricated from a high-loft electrically charged polymeric microfibers. "High-loft" is understood in the art to mean a fiber structure that contains more air then fiber. In more specific embodiments, the polymeric microfibers comprise electret charged fluorinated melt-blown polyolefin microfibers having an effective fiber diameter of between about 0.5 μm and 12 μm, or more specifically between about 0.7 μm and 8 μm, or even more specifically having an average effective fiber diameter of about 1 μm. In particular embodiments, the air permeability of the fiber layer is between 80 $l/m^2/s$ and 8000 $l/m^2/s$, and according to specific embodiments is between 100 $l/m^2/s$ and 1000 $l/m^2/s$. Air flow resistance according to some embodiments is between 1.5 Pa and 100 Pa. Fibrous filter media suitable for embodiments of the invention are available from Hollingsworth & Vose of East Walpole, Mass.

As shown in FIG. 2C, according to some embodiments the shell has a generally aerodynamic shape as defined from the front to the rear, the front being the leading edge of the air flow. Nearly any shape resulting in a substantially laminar flow of air around the contour of the shell is suitable. Non-limiting examples of suitable shapes of the horizontal cross-section of the shell include a substantially triangular shape 29, a teardrop shape 31, a pear shape 33, an aerofoil shape, or a saddle shape 35. In a very specific embodiment, the shape is saddle-shaped.

According to some embodiments, the exterior surface 23, or both the exterior surface 23 and the interior surfaces 21, of the shell 17 include a pattern of corrugations 37 effective to create turbulence in the airflow around and through the cup 13 resulting in vibration of the cup 13 and accelerated activation of $ClO_2$ fumigant. Any pattern of surface features is suitable; however generally the patterning should be symmetric about a horizontal axis lengthwise through the shell in order to avoid excessive agitation.

D. Activation Area

The activation area 3 comprises a series of conduits for addition of water, reagents and neutralizing solution to either the activation cup or directly into the air flow. The conduits include a first conduit 4 adapted for controlled metered addition of water to the activation cup 13, a second conduit 6 adapted for addition of dry reagents to the activation cup 13, and a third conduit 8 adapted for addition of neutralizing reagents to the activation cup. Any commercially available dry reagents for the production of $ClO_2$ are suitable. In specific embodiments, the dry reagents are added as a tablet, for example, a tablet comprising sodium chlorite and sodium dichloroisocyanurate dihydrate. Inorganic acids and inorganic salts may also be included. Suitable dry-reagent tablets activated to produce $ClO_2$ upon addition of water are available from Quip Laboratories, Inc. of Wilmington, Del.

The conduits 4, 6, 8 may be controlled by ball-valves 10 which may be opened and closed by manual turning, or by automated turning achieved without manual touching. In some embodiments, the by-pass area 5 comprises at least one conduit 8 in communication with a pipe or tube traversing the by-pass area 5 for addition of neutralizing reagents directly to the air flow.

E. Neutralizing Area

The neutralizing area 7 comprises two distinct functional spaces—a leak abatement space 39 and a $ClO_2$ fumigant neutralization space 41. Although the neutralizing space will be described as a series of treatment centers in sequential order, it is understood that any additional treatment stations may be included at any point as determined by particular needs. Air flow may be directed into the neutralizing space by valve manipulation. The $ClO_2$ fumigant neutralizing space 41 comprises: a first treatment station 43 comprising ultraviolet light (UV). According to specific embodiments, the inside of the UV treatment center includes a UV light source and a reflective interior surface to increase exposure of the $ClO_2$ gas to the UV light in the station. The UV treatment station is contained within a compartment that may be irregularly shaped to further increase disruption in the $ClO_2$ air flow, which results in increased dwell/residential time in the UV station. In some embodiments, the variable speed blower is positioned to direct fumigant air flow to a wall of the UV compartment, further creating disruption in the flow and UV exposure dwell time. The user is protected from exposure to the UV light since the system is contained within a sealed opaque container, such as a cabinet. In very specific embodiments the UV light is designed to turn off when the cabinet is opened.

The first treatment station 43 is in operational communication with a variable air blower 45. Generally, when the activating area and neutralizing area are housed together, a single variable air blower with dedication capability comprising, for example, flow valves, may be utilized, although this is not always necessary. In embodiments where the activating area and neutralizing area are contained separately, different variable air blowers may be employed for the activating versus neutralizing functionality. It is clear that various configurations of air blowers may be utilized without departing from the spirit of the invention. In comparison to the relatively low flow force generated by the air blower for activation functionality, the air blower 45 is set to blow fumigant waste air at a relatively high speed through the first treatment station. "High" in this context is defined as at a force sufficient to agitate and degrade $ClO_2$ present in the fumigant waste air, thereby resulting in partially treated air. The air flow from the variable air blower 45 is directed to an interior surface of the UV station compartment in order to create flow disturbances as the air flow passes into the second treatment area. Partially treated air may include both $ClO_2$ and degradation products of $ClO_2$.

Upon exiting the first treatment center, the now-disrupted air flow enters a second treatment station 47 comprising a reservoir 49 of liquid neutralizing solution. $ClO_2$ neutralizing solutions are known in the art. According to a preferred embodiment, the neutralizing solution comprises sodium thiosulfate and water. In some embodiments a diffusion plate 51 or baffle separates the first and second treatment stations. As the disrupted flow is forced into the neutralizing solution reservoir 49, frothing and bubbling and formation of turbulent flow features such as eddies occurs, further aiding the neutralizing process effectuated by the neutralizing solution, both by the agitation and the extended residential time in the reservoir that results. In some embodiments the reservoir 49 is separated into at least three chambers (not shown). Diffusion plates or baffles may be utilized to separate/create the chambers, however all chambers contain the neutralizing solution reservoir. The second chamber, which in preferred embodiments is also the largest chamber, is the chamber from which the air flow enters the third treatment center, such as third treatment center 53 described below. The second chamber is positioned between the first and third chambers. The first chamber is in direct communication with the first treatment center 41 and the flow passes into the first chamber at an angle, causing disruptions in the flow. The third chamber on the opposite side of the second chamber from the first chamber is positioned to receive air flow from the leak abatement space 39 powered by another blower 63 functioning as a re-circulating blower. A person of ordinary skill in the art will realize that additional configurations of chambers designed to promote turbulence and thereby increase the rate of the neutralizing reaction in the reservoir may utilized. Generally, more chambers results in greater turbulence and reaction mechanics favoring enhanced neutralization.

The waste fumigant air leaves the second treatment center 47 as substantially treated air. As used herein, "substantially treated" means that only residual amounts of $ClO_2$ may remain in the air flow. The solution in the reservoir is bubbling and frothing from the flow disruptions and forced flow through diffusion plates into the reservoir. The second treatment station is in communication with a third treatment station 53 comprising a humidification filter 55 positioned over the reservoir 49. The humidification filter 55 is configured to capture, contain and return neutralizing solution to the reservoir while permitting substantially treated air to pass through. In specific embodiments the humidification filter 55 is fabricated from open-celled polymeric material. Localized high concentrations of neutralizing liquid may form in some of the cells, further providing enhanced neutralization capacity. According to specific embodiments, the humidification filter 55 comprises a humidification pad and humidification fins. In more specific embodiments the humidification fins comprise grooves. Generally the fins are aligned above the reservoir 49 and beneath the humidification pad.

As the air flow passes through the third treatment station it enters a fourth treatment station 56 comprising coated zeolite 58. The zeolite 58 may be coated with sodium thiosulfate or another suitable $ClO_2$ degradant or neutralizer. Specific organic materials are known in the art as effective coatings for neutralization of $ClO_2$. In other specific embodiments calcium hydroxide may be coated over the zeolite to remove carbon dioxide.

In some embodiments a treatment station 57 comprising activated charcoal suitable for removing odiferous molecules from the treated air may be included. For example, sulfur gas may be present in the treated air. The activated charcoal may be sprinkled into the zeolite or may form a layer over the zeolite, or may in some aspects be a layer distinct from the zeolite. It is an important consideration to the design of the neutralizing area that the waste fumigant is not contacted with a carbon-based filter until after the $ClO_2$ has been neutralized so as to avoid a fire hazard resulting from localized $ClO_2$ concentration build up in the spaces and pores of carbon filtration media.

According to some embodiments, the leak abatement space 39 comprises: a blower 59 adapted for pulling treated air through an exit port 60 of the neutralizing space 41 and into the leak abatement space 39. This blower acts as a pull-blower and also aids in creating circulation of air in the leak abatement space to ensure that any leaks into the internal space of the cabinet are dispersed and re-circulated into the neutralizing space. A fifth treatment station 61 comprising UV light is located in the leak abatement space. A second variable air blower 63 is positioned to blow air from the leak abatement space 39 through the fifth treatment station 61 and into a chamber of the reservoir 49 at a high speed. In some embodiments, the air flow from the fifth treatment station is disrupted by directing the air flow from the blower 63 at an oblique angle to a containment wall of the UV treatment space such that it enters the chamber of the reservoir as a disrupted air flow, creating turbulence and eddy formation in the reservoir. A second diffusion plate 65 or baffle may be positioned at an interface 67 between the fifth treatment center 61 and the reservoir 49 to create bubbling and frothing in the reservoir. As used herein, "high" flow rate is defined as sufficient to agitate and degrade $ClO_2$ present in the leak abatement space 39.

In some embodiments the leak abatement 39 space may be connected to an environment external 71 to the sealed housing by one or more hoses 69 including at least one hose connected to the variable speed blower 63 to provide a vacuum force effective to pull potentially contaminated air from the external environment 71 and direct it into the fifth treatment station 61. A user may immediately decontaminate the external environment where a leak is indicated by one or more sensors located in the external environment by utilizing the vacuum hose. The air blowers of the system are sealed and configured to operate on direct-current power for safety. Ventilation blowers designed for marine (boating) use are suitable as the blowers of the decontamination system because they are sealed to the immediate environment and water/moisture resistant. Such blowers are available from a number of suppliers including Attwood Marine Products, Inc.

According to some embodiments the activating area 3 and neutralizing area 7 may be housed together in one sealed housing 14, for example in a cabinet. In other embodiments the areas may be housed separately in independent sealed housings. In particular embodiments suited for decontamination of buildings via the HVAC system, multiple independently housed activating areas 3 may be employed throughout the building along with at least one neutralizing area 7. The cabinets, whether housing independent activating or neutralizing areas or combinations thereof, may include wheels for simple portability, or other portability means (handles, pull handles and the like). In this way the decontamination system may be configured as a modular and portable system. Further, systems may be converted readily from closed to open systems by manipulation of sealed valves placed within the system piping.

F. Decontamination Chamber

Figure 3:
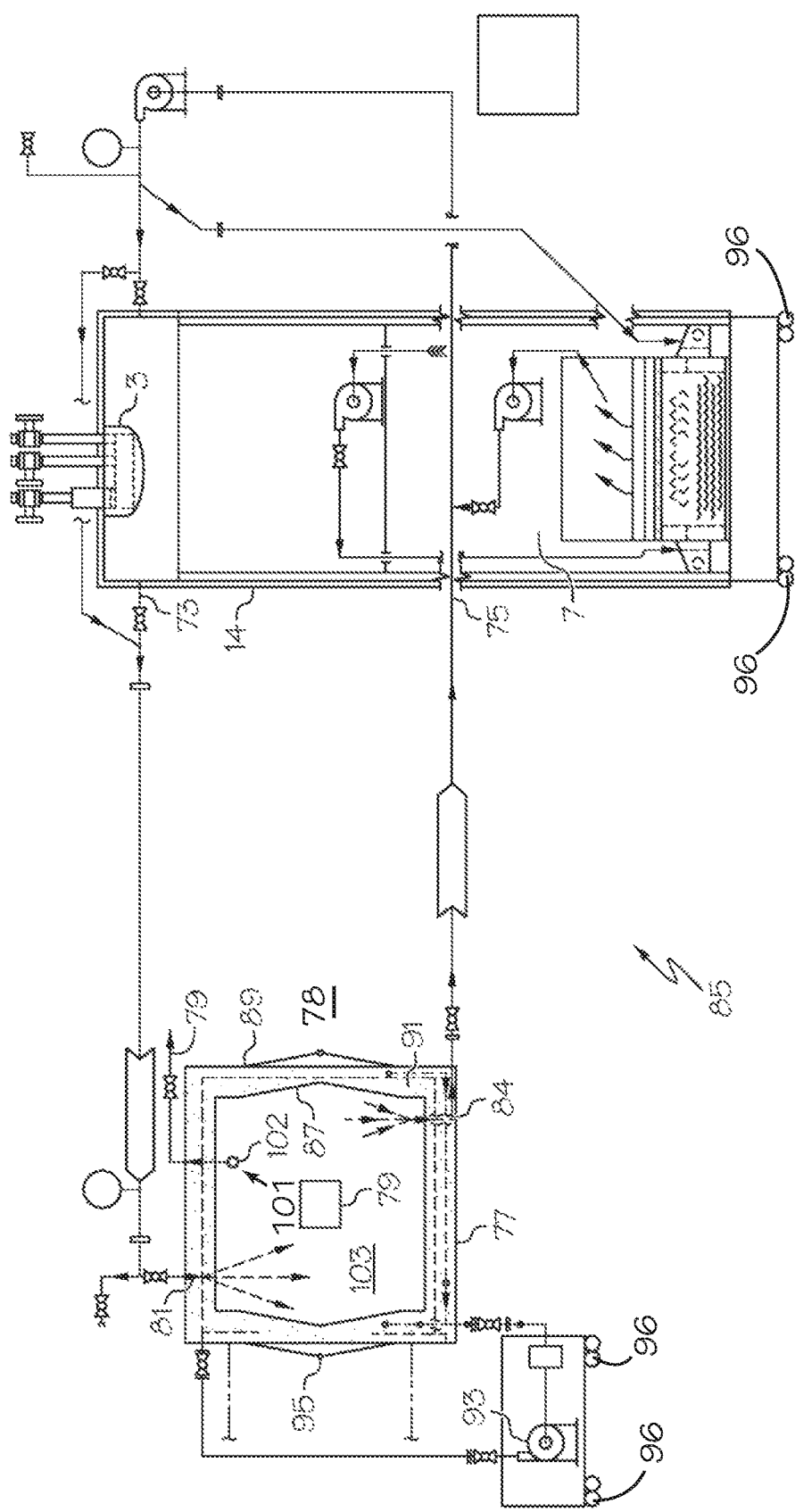
FIG. 3 sets forth an exemplary schematic representation (not scaled) of a closed loop system including activating and neutralizing areas which may or may not be combined into a single contained unit, operationally connected to a decontamination chamber.

According to some embodiments, the activation area 3 and neutralizing area 7 are housed together in one sealed housing 14 and the system further comprises a separate decontamination chamber 77. The sealed housing comprises a $ClO_2$ fumigant outlet port 73 and a $ClO_2$ waste air inlet port 75. The decontamination chamber 77 is scalable and configured to hold a product 79 to be decontaminated and comprising an inlet port 81 sealingly connected by a positive flow line to the $ClO_2$ fumigant outlet port 73 and an outlet port 84 sealingly connected by a negative flow line to the $ClO_2$ waste air inlet port 75 to form a closed loop decontamination system 85. As shown in FIG. 3, the sealed housing 14 may be fitted with wheels 96 for portability.

Specific size, dimension, and functionality of decontamination chamber 77 will vary according to the decontamination needs. The chamber may be scaled down for small articles or scaled up for very large articles and may be made collapsible for portability needs. According to some embodiments, and with reference to the exemplified embodiment of FIG. 3, the chamber comprises an inner containment structure 87 and an outer "skin" 89 and has an air space 91 between the inner containment structure 87 and outer skin 89. The inner structure 87 and outer skin 89 are fabricated from a fire and blast retardant material and may include an anti-static coating on surfaces contemplated as being operationally contacted with $ClO_2$ fumigant or $ClO_2$, waste air. In other specific embodiments all piping and tubing of the system through which $ClO_2$ traverses comprise a static-resistant material. Further, the decontamination system is grounded and utilizes DC current/batteries to avoid realizing an ignition risk associated with $ClO_2$ gas.

In some embodiments, the decontamination chamber further comprises at least one air blower 93 positioned to inject air in the air space 91, wherein the at least one blower 93 is sealed and operates on direct current. The chamber 77 may include one or more doors 95 and a blower 93 may be positioned in proximity to each door 95. In very specific embodiments the decontamination chamber is constructed to be erected and collapsed by the use of ambient air. In particular air may be pumped into support tubes arranged along the periphery, the tubes become rigid and pull the fabric of the chamber as they expand, thus erecting the chamber. As shown in FIG. 3, the air blower 93 may be fitted with wheels 96 for portability.

G. Open Loop System

The inventive decontamination system is particularly suitable for decontamination of a building 150 or contained area within a building via the ductwork of the building's HVAC system 97, which also serves to decontaminate the HVAC system. Residual contamination present in HVAC duct work is responsible for recontamination of decontaminated buildings where the decontamination methods fail to account for it. In this application, the decontamination system is configured as an open-loop system with activating areas (referred to as activators) connected to neutralizing areas (referred to as neutralizers) by connections to the building's HVAC system 97 comprising an HVAC unit 99 and HVAC duct work 100. At least one activating area 3 is in fluid communication with a neutralizing area 7 via the HVAC duct work. Referring to an embodiment illustrated by FIG. 4, multiple independently housed activating areas 3 are located in the building relative to the HVAC unit 99 such that gravity aids in distribution of $ClO_2$ fumigant through the duct work 100. The number of activators should correspond to the size of the building and the number of rooms into which the floor or building is divided, as well as the desired target concentration of $ClO_2$. The optimization of a particular configuration of the system will be readily apparent to one of skill in the art.

A series of sensors and read-outs may be utilized to monitor the $ClO_2$ concentration throughout the decontamination and neutralizing cycles. Where a decontamination chamber is utilized, concentration of $ClO_2$ fumigant in the decontamination chamber 77 is monitored by a monitoring device 101. The device comprises at least one $ClO_2$ sensor 102, which may be located in an interior space 103 of the decontamination chamber 77 or external to a sampling port 79 in communication with the interior space 103 of the decontamination chamber 77. $ClO_2$ fumigant leakage may be monitored by one or more monitoring devices comprising $ClO_2$ sensors 102 located in a space exterior 78 to the decontamination chamber 77 or exterior to any of the modular components according to particular embodiments of the invention. Suitable sensors and monitors are well known in the art and available from multiple manufacturers.

H. Decontamination Methods

1. $ClO_2$ Fumigant Generation Methods

Embodiments of the invention also include methods based on utilizing the inventive system technology, either as individual components or in any modular configuration of components. Methods for generating chlorine dioxide fumigant in a directed flow with a minimum of water comprise providing an activation cup according to embodiments of the invention and directing an air flow through the cup. According to specific embodiments, the cup comprises an outer layer 15 of crush-resistant thermally bondable non-woven fibers molded into a transversely bisected aerodynamically-shaped shell 17 where the shell 17 is open at the top 19 and has an interior surface 21 and an exterior surface 23. The exterior surface 23 and interior surface 21 may include a pattern of corrugations 37 to create turbulence in the air flow such that the reaction mechanics are enhanced to increased production of fumigant. The cup comprises at least one filter layer 25 interposed between the outer molded layer 15 and an inner molded layer 27 and including one filter layer adjacent and adherent to an inner surface 16 of the outer layer 15. The filter layer may comprise multiple layers, however at least one layer 25 comprises high-loft electret charged fluorine-coated polyolefin microfibers such that the activation cup 13 is adapted to retain water and reaction by-products while permitting gas to pass through, directed by the air flow. In specific embodiments, the cup is flexibly suspended in the air flow. Dry reagents for production of $ClO_2$ fumigant are added to the cup 13 and the directed air flow is initiated. Corrugation patterns in the cup create mild turbulence in the flow resulting in a slight vibration of the cup. "Corrugation" herein is meant to include any surface feature that disrupts air flow. It is an important consideration to keep the air flow speed low during this process to avoid degrading $ClO_2$, which is a relatively fragile molecule. The addition of water to the cup initiates generation of $ClO_2$ fumigant that is directed out of the cup 13 with the air flow while water and $ClO_2$ generation reaction by-products are substantially retained in the cup 13. Analysis of the resultant $ClO_2$ fumigant flow reveal that it is comprised almost entirely of $ClO_2$ fumigant without a significant presence of water or acid vapor.

Although the activation cup aspect is described herein in relation to generation of $ClO_2$ fumigant, it is contemplated that the cup would provide similar benefits with respect to the in situ generation of any chemical gas.

2. Neutralizing Methods

Embodiments of the invention further include methods for neutralizing fumigant chlorine dioxide ($ClO_2$) in a sealed neutralizing area 7. The neutralizing area 7 comprises a leak abatement space 39 and a neutralizing space 41, and the neutralizing space 41 comprises a series of treatment stations and at least one blower. Methods may include the liquid neutralizing solution reservoir treatment station in combination with at least one additional treatment station described herein. A preferred embodiment includes the UV 43, neutralizing solution 47, humidification filter 53, and zeolite 56 treatment stations in sequential order. In some embodiments the method comprises blowing $ClO_2$ fumigant to-be-neutralized into a treatment station comprising ultraviolet light, resulting in partially neutralized air. The blowing is effectuated at a speed high enough to degrade $ClO_2$. The air flow is directed to hit a compartment wall of the UV station at an oblique angle in order to create disruptions in the air flow as it enters the liquid neutralizing solution reservoir. The partially neutralized air from the UV treatment station may be blown through a diffusion plate 51 and into a treatment station comprising a liquid neutralizing solution reservoir.

The reservoir may be divided into chambers (not shown) separated by diffusion media in the form of plates or baffles, resulting in bubbling and frothing in the reservoir and enhanced neutralization reaction mechanics and degradation, resulting in substantially neutralized air. In a preferred embodiment the liquid neutralizing solution comprises sodium thiosulfate and water. In specific embodiments bubbled solution is captured and returned to the reservoir by a treatment station 53 comprising a humidification filter 55 that permits the substantially neutralized air to pass through the filter. In further specific embodiments the substantially neutralized air then passes and into a treatment area 56 comprising coated zeolite 58 (coated with one or more of sodium thiosulfate and calcium hydroxide) to neutralize any remaining $ClO_2$ and to remove other toxic gaseous byproducts remaining in the substantially neutralized air, resulting in neutralized air; and, optionally, passing the neutralized air through activated carbon to remove odiferous molecules which may be present in the neutralized air. The activated carbon may be in particle form intermixed with the zeolite, or sprinkled over the top of the zeolite layer, or may form a distinct layer through which the neutralized air passes.

The neutralized air is then pulled into the leak abatement space 39 by a blower 59 acting as a pull blower, where it may be circulated in the leak abatement space and recirculated through the neutralizer by a variable speed blower 63 directing air from the leak abatement space into the neutralizing space 41 and through another UV treatment station 61. A valve controls whether or not recirculation is effectuated. Leaks detected on the outside of the sealed housing 14 by sensors/monitors (such as sensors 102 in FIG. 3) may be vacuumed into the leak abatement space by one or more hoses 69 sealingly connecting the leak abatement space to an environment 71 exterior to the housing. The re-circulation loop is opened and contaminated air is pulled through by the variable speed blower directing it into the UV treatment center 61 and into the reservoir 49 as described earlier.

I. Decontamination Chamber Application

The decontamination chamber system of the present invention may be configured into a specific embodiment, such as shown in FIG. 3, having utility for sterilization and transportation of sterilized product in a single chamber. In this embodiment the "decontamination chamber" 77 is the transported chamber and a closed loop is formed with a combined activator/neutralizer unit 14 by connecting outlet port 73 of activation area 3 with inlet port 81 of decontamination chamber 77 and outlet port 84 of decontamination chamber 77 with inlet port 75 of neutralizing area 7 as described herein. An article 79 in need of decontamination is placed into the decontamination chamber 77 and the method comprises generating $ClO_2$ fumigant and directing the generated $ClO_2$ fumigant through the closed loop to achieve a concentration of $ClO_2$ fumigant in the decontamination chamber across a time frame sufficient to achieve target sterilization of the product. The concentration may be monitored and affirmed by at least one $ClO_2$ concentration sensor 102. Once the target concentration is reached and held for the target residential time, the decontamination chamber 77 is decoupled from the sealed housing 14 while maintaining sealing of the decontamination chamber from the environment. The sterilized article is then transported to a target destination in the chamber. It is contemplated that the decontamination chamber in specific aspects of this embodiment may be adapted to suitcases, trunks, coolers, medical containment cabinets, and the like.

J. Room Sterilization Application

With reference to FIG. 5, a specific application illustrating use of a decontamination system according to certain embodiments of the invention to provide and maintain a sterile operating room environment is described. $ClO_2$ gas is theoretically an ideal sterilant for this environment, which contains a wide variety of substrates. A safe and effective system for providing a target concentration to an operating area of an operating room has heretofore not been developed.

Figure 5A:
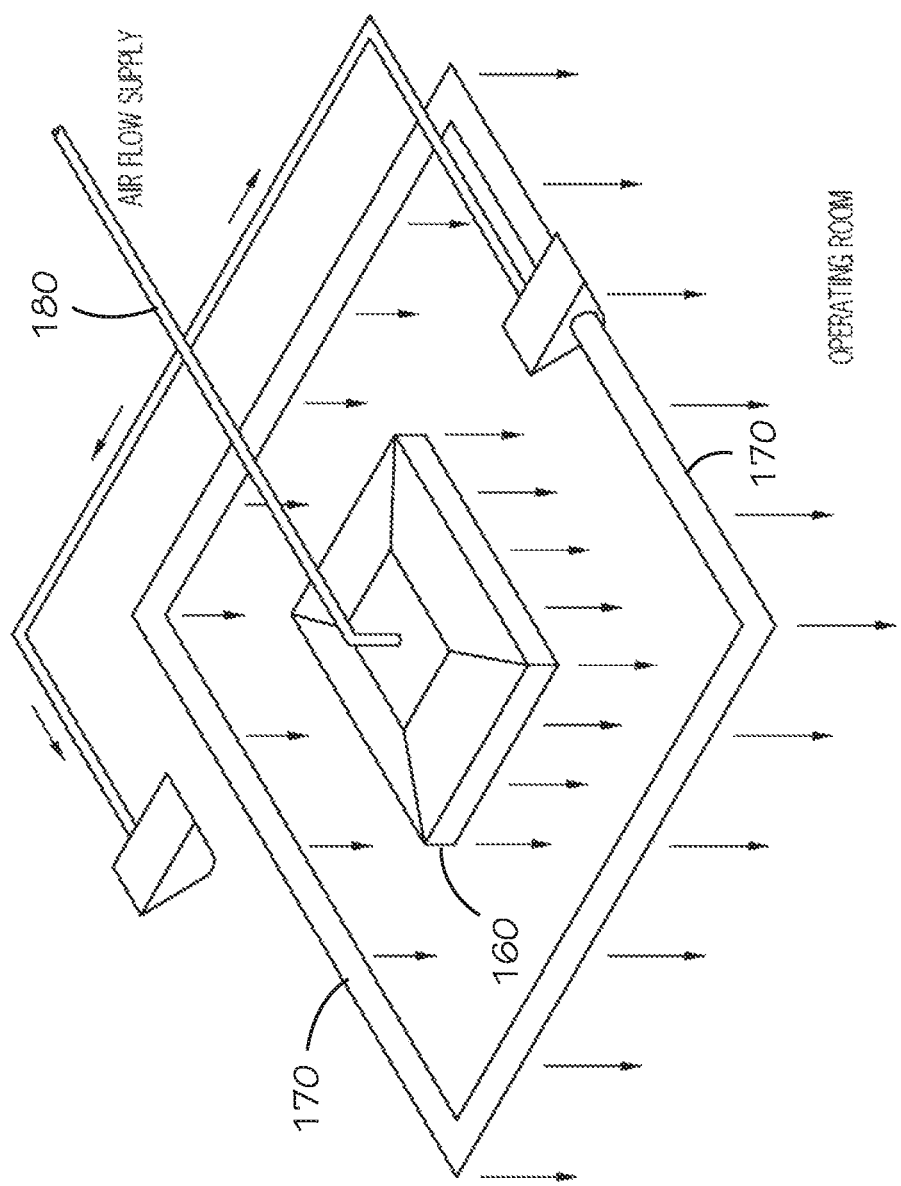
FIG. 5A illustrates a top view of a hospital operating room undergoing decontamination utilizing a main HVAC system and having a temporary wall installed around the operation room, showing a fumigant air flow into a high-efficiency particulate arrestance (HEPA) filter/diffuser positioned centrally over the operating table and into slotted diffusers placed at either side of the operating area in order to create an air curtain around the operating area.
Figure 5B:
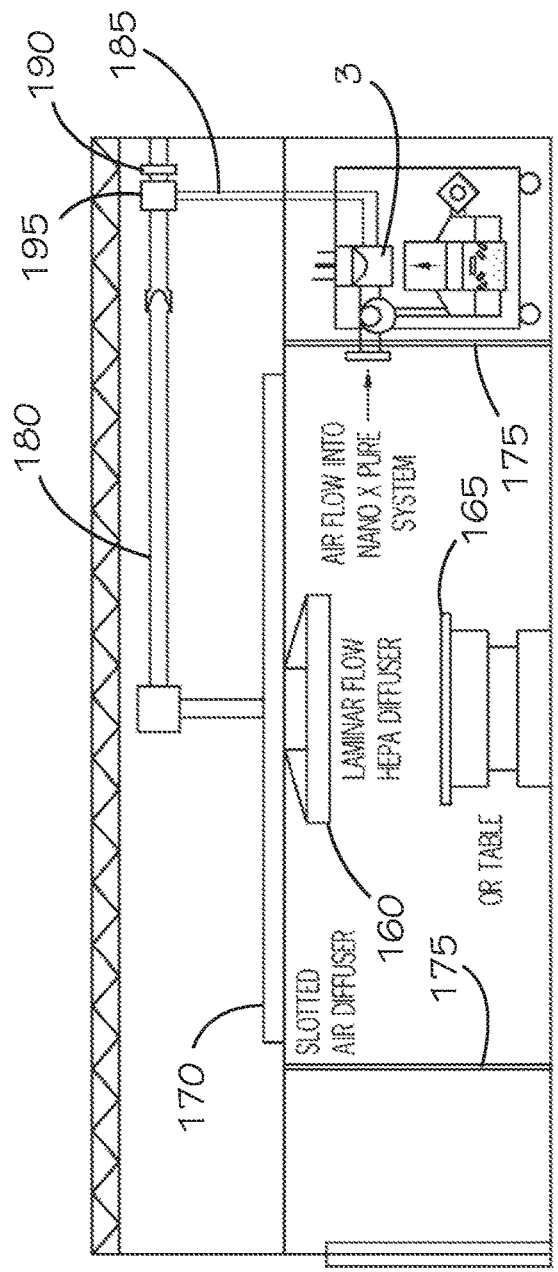
FIG. 5B shows a schematic representation of the operational combination of the decontamination system with the operating room via the HVAC system.
Figure 5C:
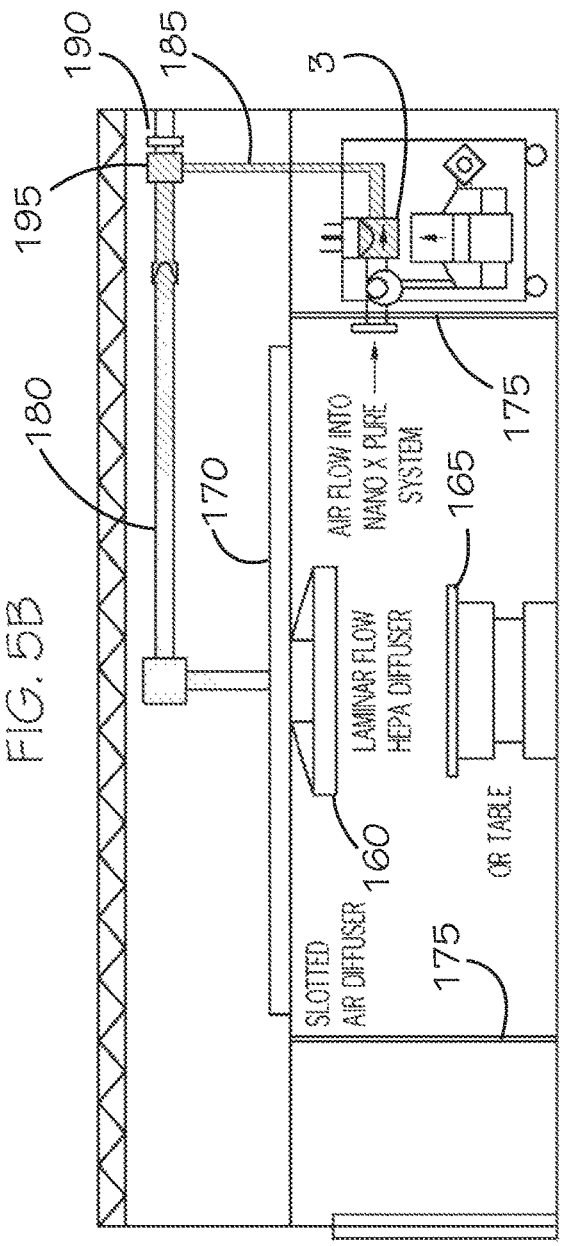
FIG. 5C illustrates generation of $ClO_2$ fumigant and flow into the air supply duct via an access port and then over the operating room via the HVAC system.

$ClO_2$ gas is activated in a system activator 3 as described above. With reference to FIG. 5A, the system comprises a laminar diffuser 160 comprising a HEPA diffuser is set over the operating table 165 area, and one or more slotted diffusers 170 set up around the periphery of the operating table area. The diffusers are in communication with the room's air supply duct work 180 connected to the main HVAC system (not shown). A temporary plastic wall 175 is installed to section off an operating room area just outside the contemplated air curtain. A conduit 185 from the activator to the air duct supply is set up so that $ClO_2$ fumigant may enter an air supply duct of the room. A damper 190 in the air supply duct is installed if not already present, in order to seal off the OR's air supply. An access port 195 to the decontamination system is installed downstream from the damper. The damper is closed. Air from the air supply duct is directed through the laminar diffuser and the slotted diffusers, forming a $ClO_2$ air curtain around the operating area. FIGS. 5B through 5E show how the fumigant is distributed and dispersed into the OR. When the decontamination need ceases, a valve may direct the air from the operating room area to the neutralizer. Recirculation enhances the neutralization process.

Target concentration may be determined by decontamination needs and regulatory requirements for particular environments. The decontamination system as described herein is capable of reaching and maintaining sterilization conditions for a variety of substrates.

K. Decontamination Examples

The following Examples are presented to illustrate and clarify certain aspects and embodiments of the invention and should not be construed to limit the full scope of the invention as defined by the appended claims.

For purposes of the Examples, dry reagents for $ClO_2$ were provided as MB-10 6 gm tablets (available from Quip Laboratories, Inc. of Wilmington, Del.). Each tablet contains 25-35% by weight inorganic acid, 35-45% inorganic salt, 15-24% sodium chlorite, and 5-10% by weight sodium dichloroisocyanurate dihydrate.

1. Example 1

This example illustrates an embodiment directed to activation of chlorine dioxide in the activation cup and demonstrates that $ClO_2$ gas is produced and directed through the cup, while water and reaction by-products and salts remain contained within the activation cup. A well-known problem in the art of $ClO_2$ decontamination systems is that production of the gas in water from dry reagents involves corrosive salts as a byproduct of the reaction. The salts shorten the life of delivery and dispersal equipment. Another well-known problem is the amount of water typically present in the $ClO_2$ fumigant, since water is necessary to catalyze the $ClO_2$ production reaction. This is particularly problematic where corrosion-sensitive articles such as electronic devices are in need of treatment. Prevention of dispersal of the salts as well as minimization of water in the treatment air flow is therefore highly desirable.

The filter layer of a specific activation cup embodiment was fabricated of polymeric microfibers comprise electret charged fluorinated melt-blown polyolefin microfibers having an effective fiber diameter of about 0.7 µm. The shell itself was formed by layering the filter material between layers of the crush-resistant thermal molding polymer and press-molding under temperatures sufficient to mold the outer and inner layers; however lower than the melting point of the fiber layer. This is essentially the same technology utilized in the respirator industry to fabricate face-worn respiration masks to protect the wearer from inhaling particles other than gas molecules, and for trapping exhaled moisture in the apparatus to prevent excessive build-up and inhalation of moisture by the wearer.

Two MB-10 tablets were activated with 30 ml water in the activation cup. The total weight of the cup, water and tablets was 50.6 g. Gas was blown with a variable air blower through the cup and into a 36 cu. ft. stainless steel tunnel. Electronic equipment was placed in the tunnel. Gas concentration was verified by ATI Porta Sens gas detector through ports in the chamber.

Gas concentration reached 240 ppm and was held for 6 hours. Total weight of activation cup and contents after cessation of reaction was 45.1 gm; hence approximately 5.5 g $ClO_2$ gas was produced. The activation cup was dried and inspected. By-product salts were found trapped in the bottom of the activation cup and in the filter layer. Neither the fan nor the computer equipment showed any effect from the gas.

2. Example 2

This example illustrates operation of one embodiment of the decontamination system using recirculation to aid in the penetration of the $ClO_2$. Demonstration of partial neutralization of $ClO_2$ with ultraviolet light was confirmed.

A roll of moldy filter material having an approximate volume of 7 cu. ft. and exhibiting a moldy odor was placed into a 36 cu. ft. stainless steel chamber. The decontamination system cabinet was fitted with an inlet and an outlet port for recirculation. Two MB-10 tablets were activated utilizing the activation cup in accordance with Example 1, and gas concentration in the chamber was monitored by an ATI Porta Sens detector. Two biological indicators were placed about 4 inches inside the roll on either end and five Rodac plates were used to sample every 20 ft. when the material was unrolled. The gas was held for three hours and reached a maximum concentration of 661 ppm. After the decontamination period was over, the $ClO_2$ gas was neutralized with UV light and gas remaining in the chamber was sampled every 5 minutes. The biological indicators and Rodac plates were sent to Air Filter Testing Labs for verification of results.

The results showed no growth in the biological indicators or the Rodac plates. The moldy smell was no longer perceptible, indicating sterilization. The UV light dropped the gas concentration about 8 to 14 ppm every 5 minutes, which is relatively slow but effective. Recirculation enhanced the penetrating ability of $ClO_2$ and the process sterilized the entire roll.

3. Example 3

This example illustrates an aspect of the system comprising a collapsible decontamination chamber fabricated of fire and blast retardant material with an air layer created between an inner scaffold and an outer layer. The volume of the chamber was about 300 cu. ft., which is the volume necessary, for example, to contain a complete hospital bed or around ten standard-sized hospital mattresses. The entire decontamination system was designed to be portable. This example also illustrates that recirculation is an effective alternative to 24 hour evacuation in off-gassing environments.

An office chair of faux leather, end table, hospital bed, and a roll of filter material were placed in the decontamination chamber in order to provide data on a range of materials and surfaces. Two biological indicators were used, one inside the drawer of the table and the other placed about three feet inside the roll of filter material. Two MB-10 tablets were activated in the activation cup spaced 70 minutes apart in order to illustrate boosting gas concentration. The gas was recirculated through two openings fitted at the end of the chamber. The test ran for three hours and an ATI Porta Sens was used to monitor gas concentration.

Fumigant gas concentration reached 93 ppm, and then started to drop. The second tablet boosted the concentration to 226 ppm. Biological indicators showed negative growth indicating sterilization. When the monitor read zero, the fan was turned off; however the monitor showed that the $ClO_2$ gas concentration rose back to 10 ppm after several minutes. This is the result of absorbent material in the chamber off-gassing absorbed $ClO_2$. The fan was restarted and set to high, and the remaining $ClO_2$ was evacuated in ten minutes as confirmed by monitoring.

4. Example 4

This example illustrates safe control of $ClO_2$ gas indoors in a confined space. The test embodiment of the neutralizing area included a neutralizing solution of sodium thiosulfate along with a finishing filter composed of zeolite coated with sodium thiosulfate plus carbon granules atop the zeolite layer to trap any residual odors. The whole system comprised two loops, one that delivered the gas into the chamber to effectuate decontamination. The second loop was an internal loop that swept any escaped gas past a UV light back into the neutralization solution as a safety feature. The system was contained in a medical grade cabinet on wheels for easy portability.

Two MB-10 tablets were used to produce a gas concentration of 72 ppm at the highest concentration point. Biological indicators were placed inside the collapsible decontamination chamber at the entering and exiting portals. The valves were manipulated and the data demonstrated that opening the valve a quarter turn on the intake side while opening the neutralization valve resulted in effective one-pass neutralization. The ATI Porta Sens detector was again used to monitor gas concentration.

The results further demonstrated that during the initial surge some $ClO_2$ gas escaped inside the cabinet but was quickly swept into the neutralizing chamber (within two minutes). Biological indicators showed no growth of microbes. The entire process took about two hours with no gas detected outside the cabinet at any time. Activation fluid inside the activating cup was neutralized and brought to a safe pH of 7.

5. Example 5

This example illustrates sterilization of a laboratory incubator in a real-world context. Price Institute for medical research at the University of Louisville reported experiencing molding of tissue samples by an incubator contaminated with mold spores. Repeated attempts to disinfect the incubator failed.

A decontamination system according to one embodiment of the invention was taken on-site to the lab. The incubator measured 2×2×3 ft=12 cu. ft. It was assumed that the internal circulation of the incubating device had become infected with mold which could not be reached by conventional scrubbing. Ambient temperature was 72° F. and ambient humidity was 57%. Temperature of activation was 113° F. A bag attached to the decontamination system was taped over the door of the incubator with the door open. Two biological indicators were placed inside beforehand. One MB-10 tablet was activated and the generated $ClO_2$ fumigant was pumped into the incubator. The door was closed and taped. The gas was held overnight, the tape was removed, the bag was placed over the door and the door was then opened. $ClO_2$ gas was evacuated and neutralized. Neutralization took about ten minutes. Biological indicators were sent to Air Filter Testing Lab for third party verification of sterilization.

The biological indicators provided positive verification of sterilization and follow-up reports from the lab indicate that the formally chronic and intransigent contamination problem has resolved.

6. Example 7

This example, when taken with Example 6, illustrates scalability of the decontamination system. The Price Institute at University of Louisville reported a black mold growing in a walk-in cooler in lab 330. The cooler had a distinct moldy odor and contained several boxes and other items. It was requested that the mold be removed so that new tissue samples and sensitive research items could be safely stored without threat of contamination.

Three biological indicators were placed inside the cooler. One was placed at the top near the internal blower, one at the bottom near the floor, the other between boxes on one of the shelves. The cooler's blower was turned off and plastic sheeting was taped over the door opening. An entering hole and exiting hole were cut and the hose that delivered the $ClO_2$ gas was inserted and sealed with tape. A total of 6 MB-10 tablets were used two at a time until the gas concentration reached sterilization levels. The process lasted about two hours. The internal blower was turned back on just before we began neutralization of the gas.

The results demonstrated complete efficacy with respect to sterilization and the gas was neutralized with no leakage. The ability of the inventive decontamination system to remove black mold in a confined space without evacuation of the facility is a significant improvement over systems known in the art.

7. Example 8

Figure 4:
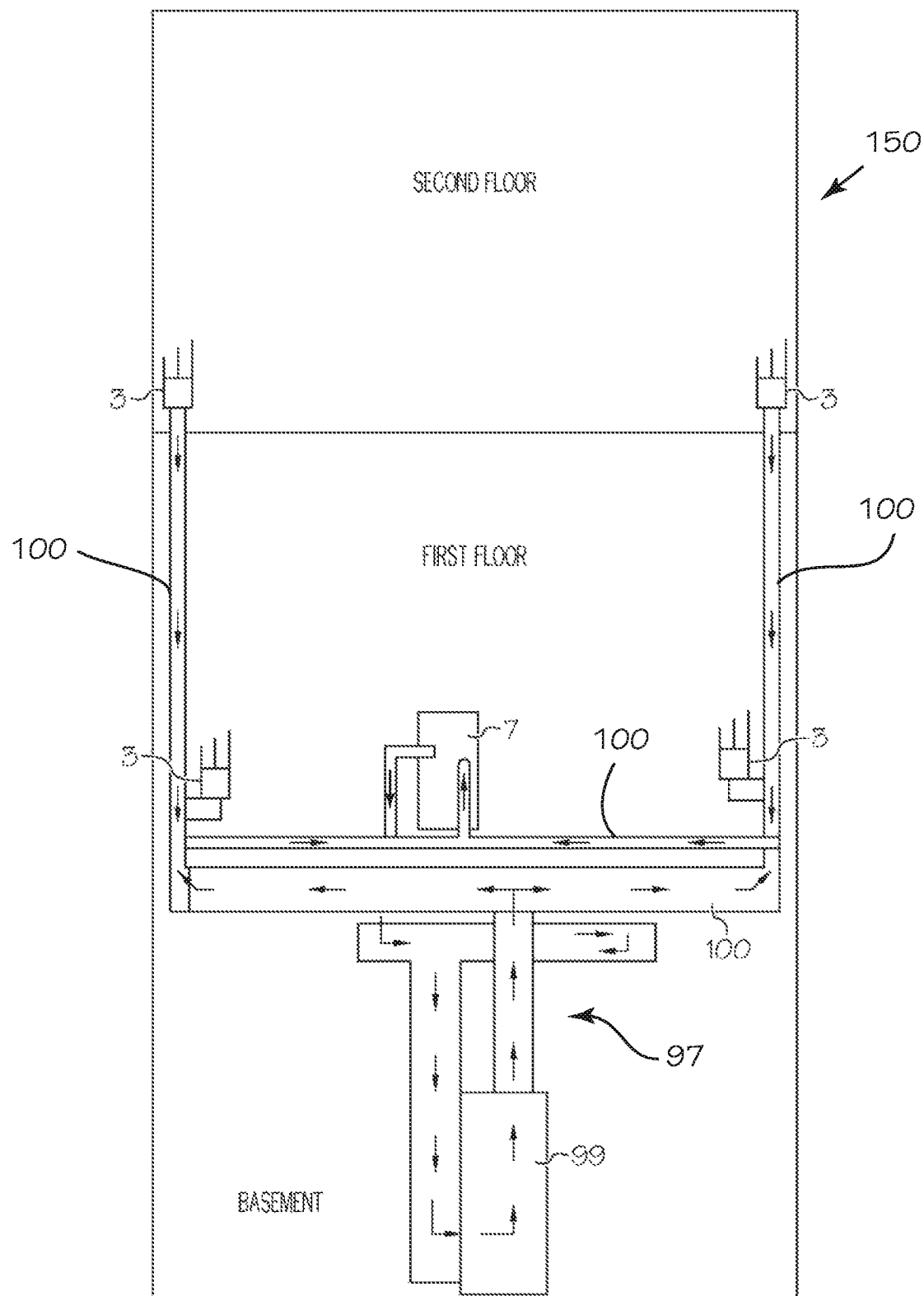
FIG. 4 sets forth a schematic representation of decontamination of a multiple-floored building where decontamination is via the HVAC system of the building and multiple additional portable activating areas are located on each of the floors over the HVAC unit location, all in communication with the main decontamination unit.

This Example illustrates decontamination of a 363 cu. ft. HVAC/duct space and the flexibility in implementing the modular/portable system for effective decontamination of multiple-story buildings. FIG. 4 illustrates a basic schematic of the design. Application of embodiments comprising multiple portable independent activation areas contained in, for example, rolling or easily transportable cabinets, is contemplated for convenient decontamination/sterilization of hospital rooms. It is critical to clean air ducts coming into the room or once air is resumed, the room may become re-contaminated. A very specific application of this embodiment relates to sterilization of operating rooms as illustrated schematically in FIG. 5.

HVAC ducts often have 90 degree turns and multiple pathways, which poses challenges for air flow being pushed from a central area into all reaches of the system. For example, multiple story homes may be difficult to air-condition with a single down-stairs unit. In order to avoid this, and to exploit the fact that $ClO_2$ is heavier than many air molecules, a particular configuration of a modular/portable decontamination system was designed. The test house from Example 6 was used. All ducts and 34 of the register vents around the house were sealed. An activating unit was placed in each of six rooms on the upper floor. Each unit had its own variable speed blower, activating cup, and three-conduit system for reagents, water and neutralizing solution as provided on the main unit. Unsealed vents were fitted with a connection that covered the vent but had anti-static tubing going back to the activating unit. If there was more than one register vent in a room, a second connection and tubing was installed and run back to the blower on the activator's intake side. This resulted in providing a mini loop circulation per room while remaining open to the main trunk of the HVAC. The main decontamination system unit was placed in the basement attached to the main trunk of the HVAC system making a closed loop which included the entire house. One MB-10 tablet was in each activating unit, while three tablets were used in the main unit, for a total of 9 tablets. The blowers were turned on low for $ClO_2$ activation. Two biological indicators were placed in the main HVAC trunk area and the cycle lasted 4 hours. At the end of the cycle the valve to the activating cups was closed and the neutralizing area was opened. Blowers were adjusted to high speed and $ClO_2$ gas was entirely evacuated in 20 minutes.

The biological indicators indicated that sterilization of the HVAC system was successfully effectuated.

L. $ClO_2$ Fumigant Activation Unit

Figure 6:
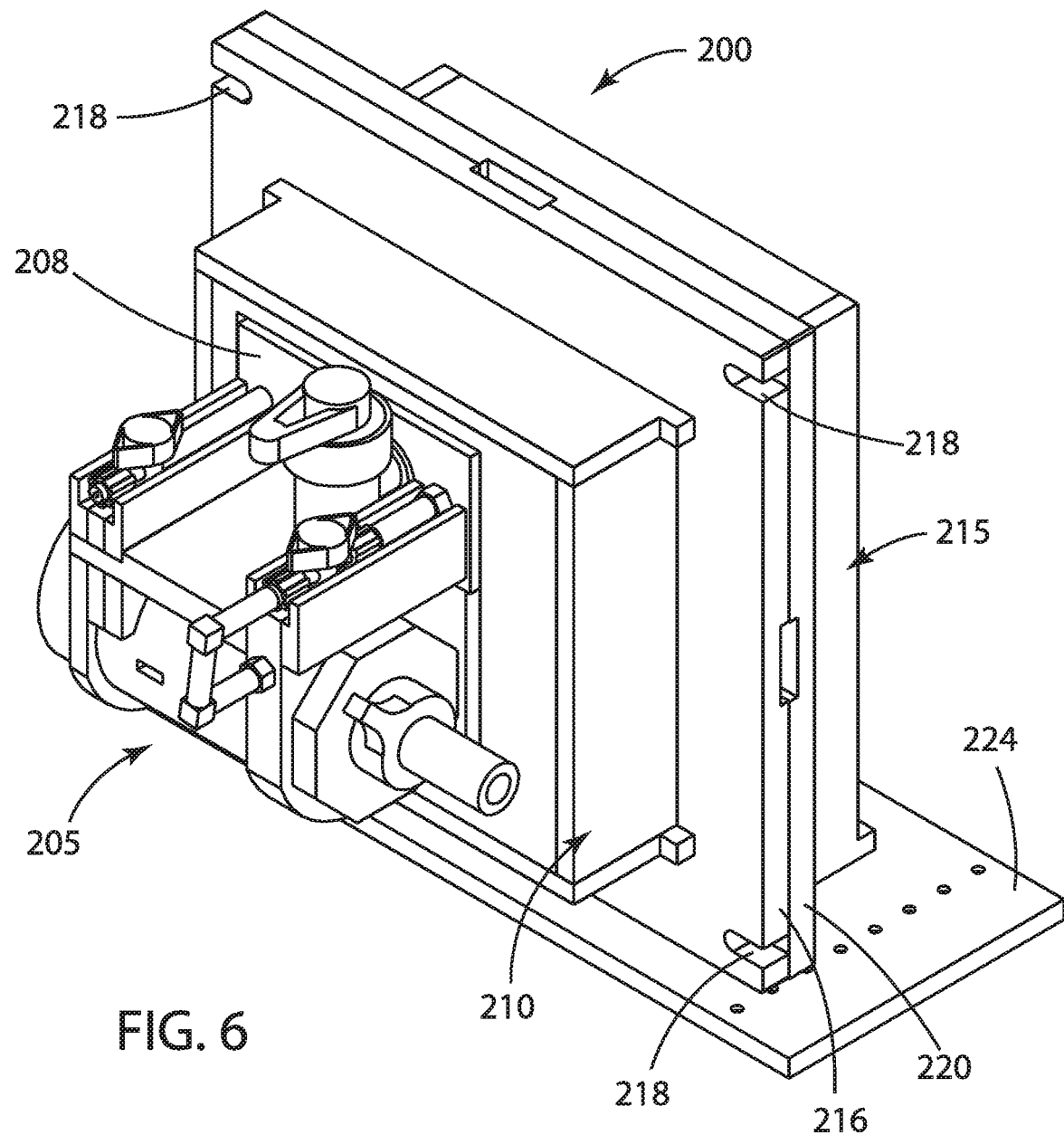
FIG. 6 is a perspective view of a $ClO_2$ fumigant activation unit according to an example embodiment with a back plate oriented in a downward direction.

Referring to FIG. 6, an example embodiment of a $ClO_2$ fumigant activation unit 200 is shown. The fumigant activation unit 200 comprises an activator 205, an activation chamber 210, and a back plate 215. Similar to the fumigant activating area 3 described above, the fumigant activation unit 200 is operable to selectively generate a decontamination fumigant of $ClO_2$ gas and air, and to direct the decontamination fumigant to an area to be decontaminated at a selected concentration and for a selected dwell time. The fumigant activation unit 200 also is operable to stop a $ClO_2$ gas generating reaction, and to recirculate $ClO_2$-containing air between the activation unit and the area to be decontaminated while neutralizing it.

As will be described in further detail below, fumigant activation unit 200 may be used as a standalone unit for generating and neutralizing $ClO_2$ fumigant gas with or without a separate neutralizing area, such as the separate neutralizing area 7 described above in connection with the example embodiment of FIG. 4. The fumigant activation unit 200 is specifically adapted for interfacing with the vents of an air distribution system such as the ductwork of an HVAC or similar system. Thus, the fumigant activation unit 200 is particularly suitable for use in generating and distributing decontamination fumigant in an "open-loop" decontamination system, such as the example embodiment of FIG. 4, wherein multiple activating areas 3 and a separately housed neutralizing area 7 are interfaced to the air distribution ductwork of a building's HVAC system. However, the fumigant activation unit 200 also includes components allowing it to be used in a "closed-loop" decontamination application. The fumigant activation unit 200 also may be adapted to interface directly to surfaces defining openings other than HVAC vents, such as window openings, flexible duct openings, and openings in sealed enclosures.

Figure 10:
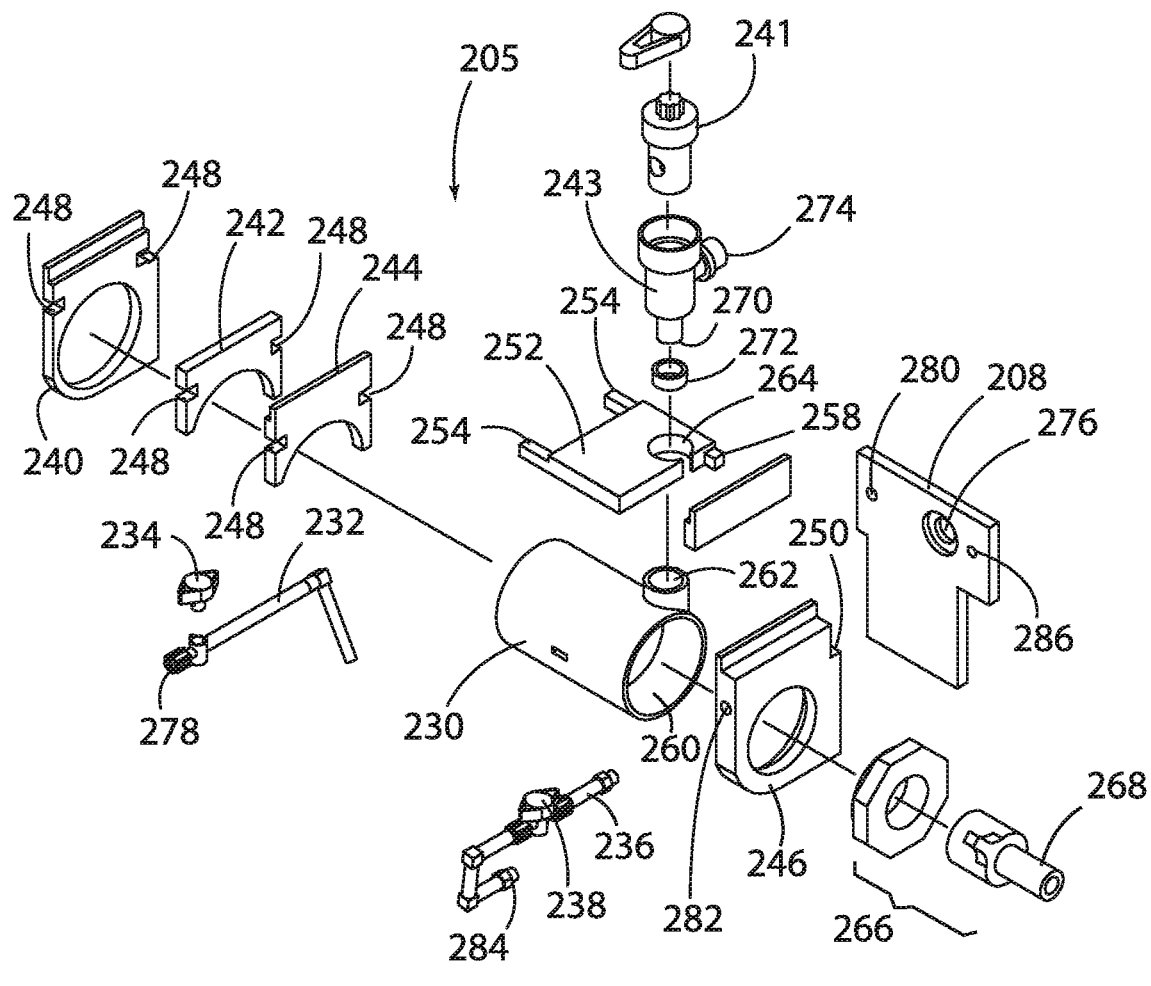
FIG. 10 is an exploded perspective view of an activator of a $ClO_2$ fumigant activation unit according to an example embodiment.

The fumigant activation unit 200 is assembled as a sealed unit. As best seen in FIGS. 6, 8, and 10, the front of the activator 205 includes a bulkhead 208 comprising a substantially flat plate. The activation chamber 210 has a back wall 212 with a recessed portion 214 on its outer surface. The recessed portion 214 is shaped and dimensioned to receive and retain the bulkhead 208 when the front of the activator 205 is aligned and brought into contact with the back wall of the activation chamber 210. The bulkhead 208 and activation chamber 210 are securely held together with conventional fasteners and gasket material (not shown) is adhered between them to provide an air/gas tight sealed assembly.

Figure 11:
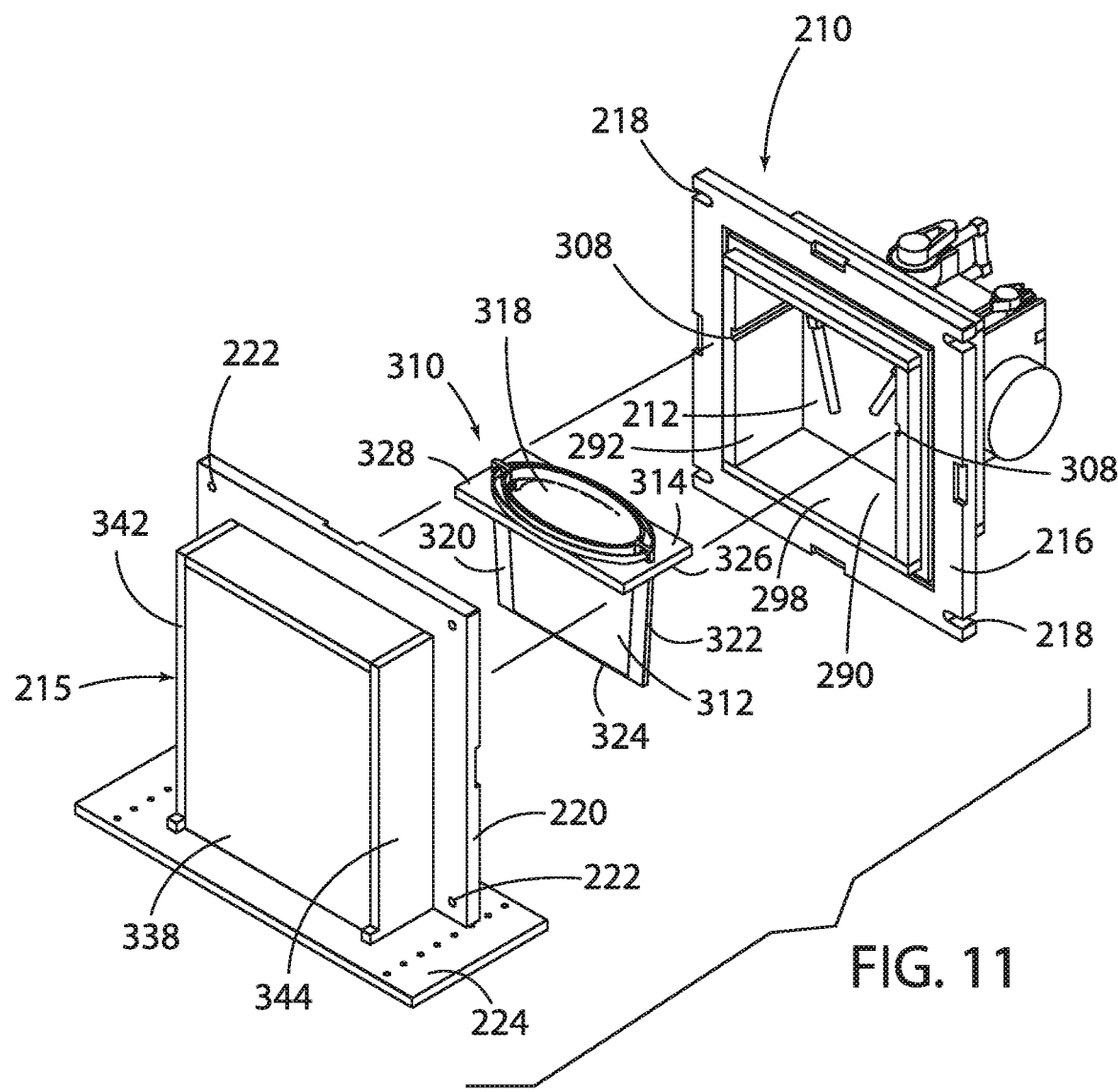
FIG. 11 is an exploded front perspective view of an activator, activation chamber, activation pouch, and back plate of a $ClO_2$ fumigant activation unit according to an example embodiment.
Figure 12:
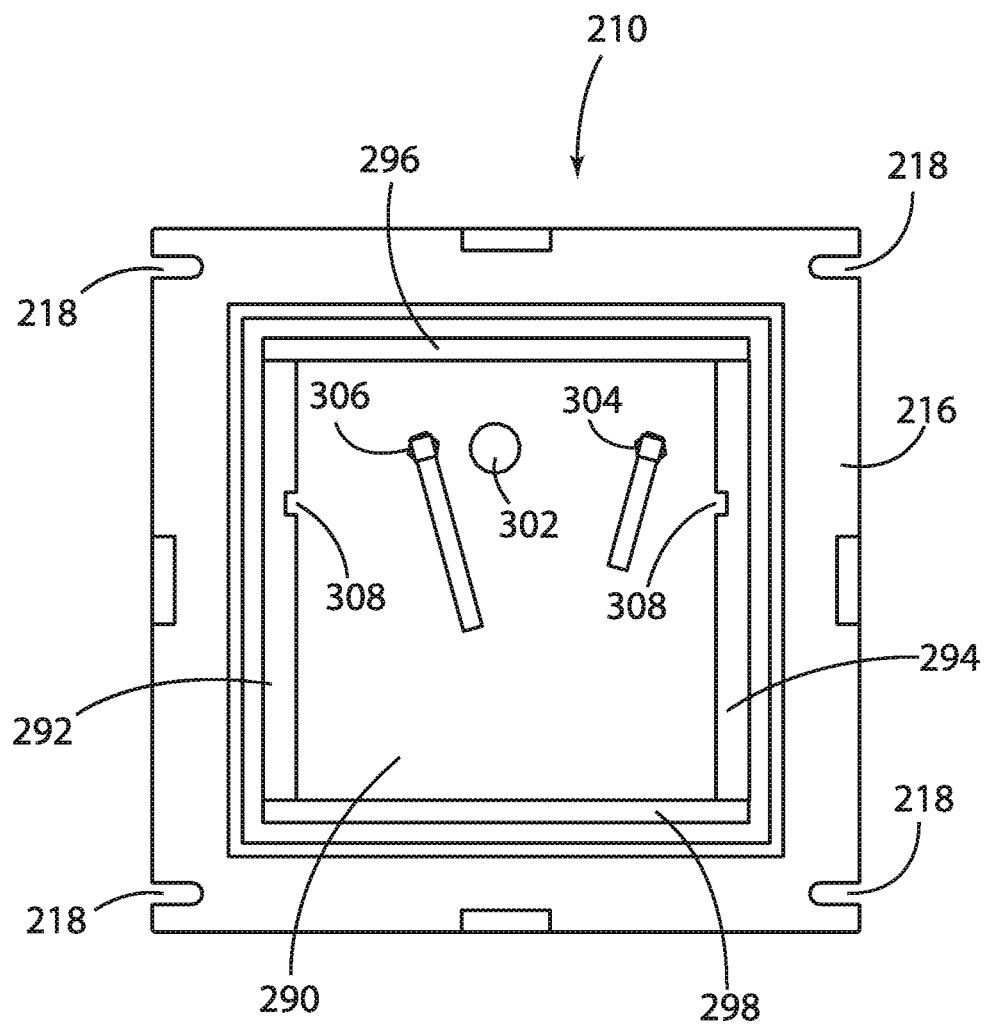
FIG. 12 is a front view of an activation chamber of a $ClO_2$ fumigant activation unit according to an example embodiment.

As best seen in FIGS. 6, 8, and 11, the front of activation chamber 210 comprises a flange or frame 216 that extends around the periphery of the activation chamber. The front surface of the flange or frame 216 is substantially flat. Slots 218 extend through the flange or frame near the corners. The back of the back plate 215 comprises a corresponding flange or frame 220 that extends around the periphery of the back plate. The back surface of the flange or frame 220 is substantially flat. Holes 222 extend through the flange or frame 220 of the back plate 215 near the corners. The frames 216 and 220 are shaped and dimensioned so that they fit together with the flat faces of the frames 216 and 220 flush and the holes 222 in alignment with the slots 218 when the front of the activation chamber 201 is aligned and brought into contact with the rear of the back plate 215. Conventional threaded fasteners are used to securely hold the activation chamber 210 and back plate 215 together and gasket material (not shown) is adhered between the frames 216 and 220 to provide an air/gas tight sealed assembly.

Figure 7A:
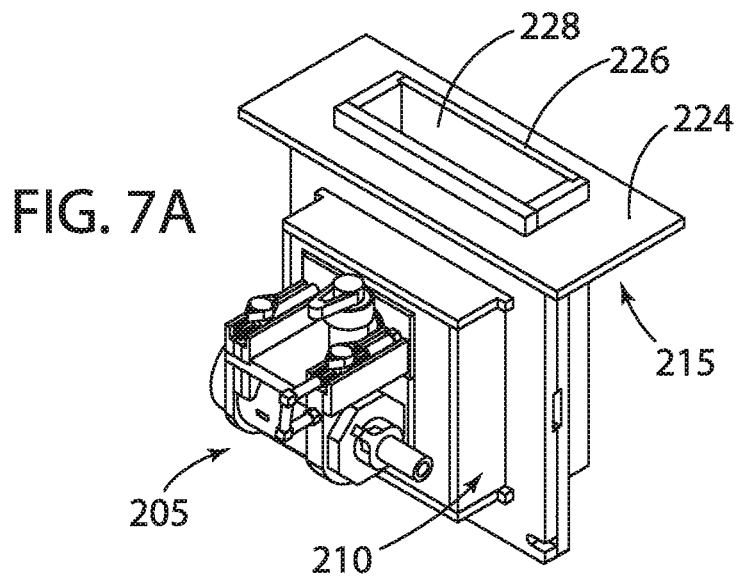
FIGS. 7A-7C are perspective views of a $ClO_2$ fumigant activation unit according to an example embodiment with a back plate oriented in upward and first and second lateral directions respectively.
Figure 7B:
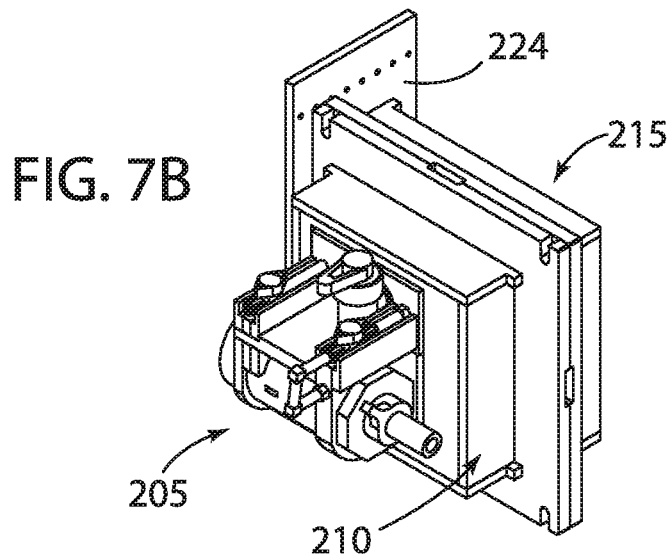
Figure 7C:
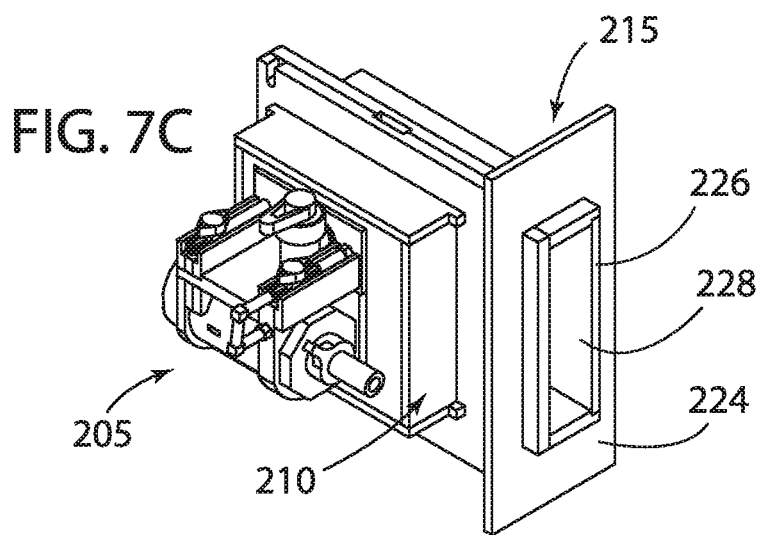

The back plate 215 further includes a mounting plate 224. The mounting plate includes a vent adaptor 226 surrounding an air/gas opening or port 228 on an outward facing surface of the mounting plate for interfacing the fumigant activation unit 200 to a vent of an air distribution system of an HVAC or similar system. As best seen in FIGS. 6 and 7A-7C, the back plate 215 can be selectively mounted to the activation chamber 210 in multiple orientations. In the particular example embodiment of FIGS. 6 and 7A-7C, the frame 216 of the activation chamber 210 and the frame 220 of the back plate 215 are square with slots 218 and holes 222 positioned in alignment near their respective corners. Accordingly, the back plate 215 can be mounted to the activation chamber 210 in four different orientations rotated by 90°. FIG. 6 shows the back plate 215 mounted to the activation chamber 210 with the vent adaptor 226 facing downward in an orientation that is convenient for use with floor mounted vents. FIG. 7A shows the vent adaptor 226 facing upward in an orientation that is convenient for use with ceiling mounted vents. FIGS. 7B and 7C show the vent adaptor 226 facing in opposite horizontal directions, which are convenient for use with wall vents.

Of course persons skilled in the art will realize that the various orientations of the back plate 215 shown in FIGS. 7A-7C and described above are not necessarily limited to use with vents mounted in the corresponding locations described. Rather, the back plate 215 may be mounted in any available orientation that is convenient or desired to best interface the fumigant activation unit 200 with a particular vent given its location and orientation. Moreover, persons skilled in the art will realize that the shape and dimensions of the vent adaptor may be altered as necessary depending on the shapes and dimensions of vents to which the fumigant activation unit 200 is desired to be interfaced. Still further, persons skilled in the art will realize that the shapes of the frames 216 and 220 could be changed to provide more available mounting orientations and orientations not necessarily limited to 90° iterations. For example, the frames 216 and 220 could be constructed as hexagons, octagons, or even circles. By aligning slots 218 and holes 222 near the vertices or otherwise around the peripheries of the respective frames, multiple mounting orientations and angles can be achieved.

In another variation, the mounting plate 224 may be configured so as to not include a vent adaptor 226 and the air/gas opening or port 228 may be enlarged or otherwise resized and reoriented. In this variation, the fumigant activation unit 200 may be mounted via the mounting plate to a variety of surfaces with the opening or port 228 in sealed air/gas communication with a variety of openings in such surfaces. In yet another variation the back plate 215 may be eliminated altogether. In this variation, the fumigant activation unit 200 may be mounted directly to a variety of surfaces via the flange or frame 216 of the activation chamber 210 with the open front of the chamber 290 of the activation chamber 210 in sealed air/gas communication with a variety of openings in such surfaces. Thus, for example, the fumigant activation unit 200 may be interfaced via the mounting plate or directly to a window frame and opening of a structure or vehicle, a surface of a sealed enclosure having an air/gas inlet or opening, and any number of other surfaces and openings. Still further, the mounting plate 224 or flange 216 may comprise or be provided with flexible interfacing material to enable the fumigant activation unit 200 to be interfaced to flexible structures, such as flexible ducts or other flexible air/gas conduits.

M. Activator

Figure 9:
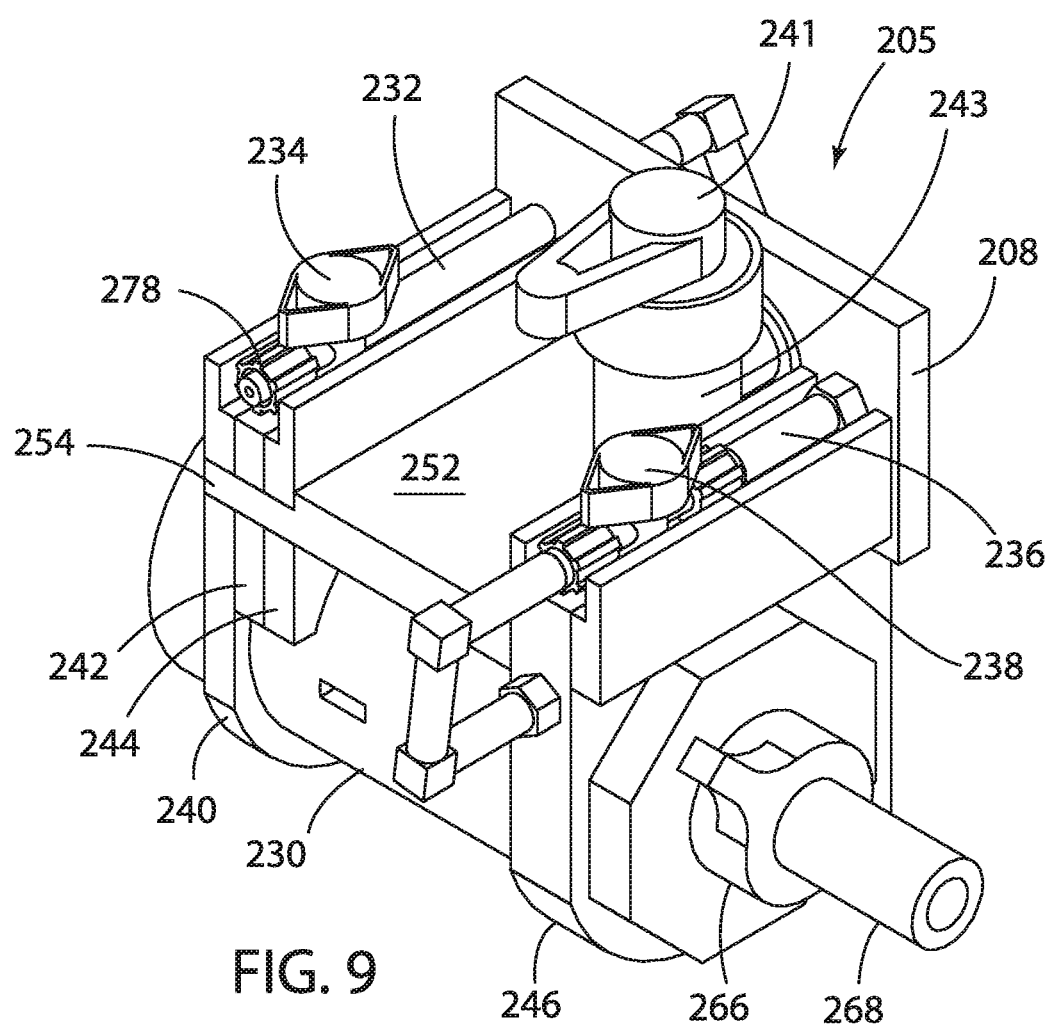
FIG. 9 is a perspective view of an activator of a $ClO_2$ fumigant activation unit according to an example embodiment.

Referring primarily to FIGS. 9 and 10, the activator 205 comprises an air blower or pump 230, a metered water conduit 232 and valve 234, an air bubbler conduit 236 and valve 238, and an air/gas circulation valve 241.

The blower 230 is mounted and held in a horizontal orientation by sandwiched vertical bracket plates 240, 242, and 244 on one longitudinal end and vertical bracket plate 246 on the opposite longitudinal end. Each bracket plate 240, 242, and 244 has corresponding key slots 248 formed therein. The key slots are aligned when the bracket plates 240, 242, and 244 are sandwiched together. The bracket plate 246 also has a key slot 250. A horizontal support plate 252 has horizontally extending keys 254 on one side and a horizontally extending key 258 on the opposite side. When the activator 205 is assembled with the blower 230 mounted in the vertical support plates 240, 242, 244, and 250, the horizontal support plate 252 sits above the body of the blower 230 and is supported by the vertical support plates 240, 242, 244, and 250 with the keys 254 engaged and supported in the aligned key slots 248 of the vertical bracket plates 240, 242, and 244 and the key 258 engaged and supported in the key slot 250 of the vertical support plate 246. All of the foregoing components may be assembled together and to the bulkhead 208 by conventional threaded or other fasteners and/or suitable adhesives. In addition, any areas where components are assembled and that could provide a leakage path for air and/or $ClO_2$ gas are sealed with a suitable sealant, e.g., silicone gasket, closed cell neoprene, or plumbing putty, to provide an air/gas-tight sealed unit.

The blower 230 has an air/gas inlet port 260 and a first air/gas outlet port 262. The ports 260 and 262 are in fluid communication within the blower. The air/gas inlet port 260 is exposed in the vertical support plate 246. A fitting 266 provides a point of connection for the air/gas inlet port 260 to one end of a conduit 268. By leaving the other end of the conduit exposed to the ambient, the fumigant activation unit 200 is configured to function as an "open loop" decontamination system. Alternatively by using the fitting 266 or a different or additional fitting to connect the air/gas inlet port 260 directly or indirectly to a duct, container, bag, or confined space, the fumigant activation unit 200 is configured to function as a "closed loop" decontamination system. The first air/gas outlet port 262 is exposed through an opening 264 in the horizontal support plate 252 and connects to the air/gas circulation valve 241.

The air/gas circulation valve 241 has a body 243 with an air/gas inlet port 270, an air/gas outlet port 274, and an internal passageway between the ports. The valve 241 fits within the body 243 between the ports 270 and 274. The air/gas inlet port 270 connects to the first air/gas outlet port 262 of the blower 230. The air/gas outlet port 274 connects to an air/gas circulation opening 276 in the bulkhead 208. Both connections are preferably sealed using an O-ring or similar seal to prevent air/gas leakage. The valve 241 is operable to selectively open and close the passageway between the air/gas inlet and outlet ports 270, 274 thereby selectively controlling the flow of air/gas between the first air/gas outlet port 262 of the blower 230 and the air/gas circulation opening 276 in the bulkhead 208.

The metered water conduit 232 and valve 234 are supported atop the sandwiched vertical support plates 240, 242, 244. The conduit has a first end with a fitting 278 for connection to a source of metered water or neutralizing solution (not shown) and an opposite second open end. The conduit 232 extends through an opening 280 in the bulkhead 208, a corresponding opening in the recessed portion 214 of the back wall 212 of the activation chamber 210 and into the interior of the activation chamber 210. The openings through which the conduit passes are preferably sealed around the conduit using suitable fittings and/or flexible sealants to prevent air/gas leakage. Various fittings may be used to position the conduit as desired in the activation chamber 210 and preferably to extend the second open end of the conduit at least partially into the pouch through the open top, as further described below. The valve 234 is located in-line in the conduit between the fitting 278 and the opening 280 in the bulkhead 208.

The air bubbler conduit 236 and valve 238 are supported atop the vertical support plate 246. The support plate 246 has an air/gas passageway that extends from the interior of the support plate near where the air/gas inlet port 260 of the blower 230 is exposed to an opening 282 in an outer surface of the support plate. A first open end of the conduit 236 connects to the opening 282 via a fitting 284. The conduit 236 extends through an opening 286 in the bulkhead 208 and a corresponding opening in the recessed portion 214 of the back wall 212 of the activation chamber 210. The openings through which the conduit passes are preferably sealed around the conduit using suitable fittings and/or flexible sealants to prevent air/gas leakage. A second open end of the conduit 236 is positioned in the interior of the activation chamber 210. Various fittings may be used to facilitate routing the conduit from the opening 282 in the vertical support plate 246 over the top of the plate and through the opening 286 in the bulkhead and corresponding opening in the back wall of the activation chamber. Fittings also may be used to facilitate positioning the conduit 236 as desired in the activation chamber 210 preferably with the second open end of the conduit extending at least partially into the pouch through the open top, as further described below. The valve 238 is located in-line in the conduit between the fitting 284 and the opening 286 in the bulkhead 208.

The reference to element 230 as an air "blower" or "pump" is not intended to limit the element to any particular form. Rather, it is intended to encompass any source capable of providing a suitable flow of air and $ClO_2$ decontamination fumigant for the purposes described herein and may include, without limitation, a fan, blower, pump, or compressor unit.

Similar to the air blowers described above in connection with other example embodiments, air blower 230 preferably is a variable speed blower. As described above, variable speed is advantageous in order to adapt the flow speed to particular decontamination needs and environmental sizes and configurations. Further, when the blower is operating to provide bubbling air to facilitate the generation of $ClO_2$ gas or to direct $ClO_2$ fumigant to an area to be decontaminated low flow force may be desirable in order to avoid degrading the $ClO_2$ and producing chlorine gas; whereas when recirculation of $ClO_2$-containing air is desired for neutralization higher speeds may be desired in order to promote degradation of the $ClO_2$. In addition, air blower 230 preferably employs a DC motor that runs off batteries or another DC power source to avoid potential ignition risks associated with $ClO_2$ gas. As noted above with respect to the air blower elements identified in other example embodiments, the type of air blower used in marine ventilation applications may be suitable for use as air blower 230. Attwood Marine Products, Inc. and numerous other companies manufacture such blowers.

Similar to the valves described above in connection with other example embodiments, valves 234, 236, and 241 may be manually operable valves, such as ball valves, electronic controlled and driven valves, or a combination of both.

It is preferred that, to the extent possible, the various components of the activator, including the conduits and fittings, be constructed of chemical resistant and anti-static materials, such as PVC and other plastics. Such materials are preferred to minimize the risks of leakage as well as accidental ignition of $ClO_2$ gas. Components constructed of materials that may accumulate a static charge should be preferably be grounded.

N. Activation Chamber

Referring primarily to FIGS. 8 and 11-13, activation chamber 210 comprises a chamber 290 defined by a vertical back wall 212, first and second opposing vertical side walls 292, 294, and opposing horizontal top and bottom walls 296, 298. The front of the chamber is open and is surrounded by flange or frame 216. The front edges of the opposing vertical side walls 292, 294 and opposing horizontal top and bottom walls 296, 298 preferably project slightly outwardly from the plane of the surface of flange or frame 216. The projecting front edges are designed to fit just within the inner edges of a corresponding opening of the back plate 215 as described further below to help align the activation chamber 210 and back plate 215 during assembly and help maintain a flush air/gas tight sealed connection between them after assembly. Gasket or other sealant material also may be used to help provide an air/gas tight sealed assembly and prevent air/gas leakage.

In one variation of the fumigant activation unit 200 mentioned previously, the activation chamber 210 may be adapted to mount directly to a surface via the flange or frame 216 rather than be mounted to the back plate 215. In this variation, the flange or frame is mounted to the surface positioned so that the open front of the chamber 290 of the activation chamber 210 is in sealed air/gas communication with an opening in the surface. The front edges of vertical side walls 292, 294 and horizontal top and bottom walls 296, 298 may project slightly outwardly from the plane of the surface of the flange 216 to fit within the opening in the surface, or may be terminated flush with the plane of the flange 216. The flange or frame may be affixed to the surface using suitable fasteners. Gasket or other sealant material may be used to help seal the interface between the flange 216 of the activation chamber 210 and the surface and prevent air/gas leakage.

The back wall 212 of activation chamber 210 has openings 302, 304, and 306. Opening 302 is an air/gas circulation inlet. Air/gas circulation inlet 302 corresponds to and is aligned with opening 276 in the bulkhead 208 of activator 205 when the fumigant activation unit 200 is assembled. As described further below, the air/gas circulation inlet 302 provides a passage through which the air/gas blower 230 of the activator 205 blows air into and through the activation chamber 210. The air flow entrains $ClO_2$ gas generated in the activation chamber and produces a decontamination fumigant. The air flow also helps direct and distribute the decontamination fumigant to an area to be decontaminated. In a closed loop configuration, the air/gas circulation inlet 302 also provides a passage through which decontamination fumigant is recirculated through the activation chamber for neutralization.

Opening 304 corresponds to and is aligned with opening 280 in the bulkhead 208 of activator 205 when the fumigant activation unit 200 is assembled. As described herein, conduit 232 of the activator 205 passes through opening 304 into the activation chamber 290 and is employed to deliver a quantity of water to the activation pouch for generating $ClO_2$ gas or a quantity of neutralizing solution to stop the generation of $ClO_2$ gas and to neutralize remaining decontamination fumigant if the fumigant activation unit is configured and operating as a recirculating closed-loop system.

Opening 306 corresponds to and is aligned with opening 286 in the bulkhead 208 of activator 205 when the fumigant activation unit 200 is assembled. As described herein, conduit 236 of the activator 205 passes through opening 306 into the activation chamber 290 and is employed to deliver a flow of air directly into the activation pouch to agitate the reaction solution and facilitate efficient generation of $ClO_2$ gas.

The dimensions of the openings 302, 304, and 306 depend on the sizes of the conduits to be accommodated and the volume of air/gas flow desired. For example, the dimensions may be scaled up for larger scale decontamination applications requiring the generation and distribution of a larger volume or higher concentration of $ClO_2$ fumigant and scaled down for applications involving decontamination of small spaces and objects.

Each of the opposing vertical side walls 292 and 294 has a horizontal slot 308. The slots 308 are adapted to receive and retain the opposite edges of a holding plate that is part of the activation pouch assembly, which is described in further detail below. The slots 308 are positioned on the respective side walls 292 and 294 so that the activation pouch is mounted in the activation chamber 290 with the open ends of the conduits 232 and 236 extending through the open top of the pouch at least partially into the volume of the pouch, and so that the air/gas circulation inlet 302 is approximately centered on and slightly above the open top of the pouch. The slots 308 also are positioned so that the pouch is suspended within the activation chamber 290 with clearance from the top, bottom, and side walls 296, 298, 292, 294 so that air blown into the activation chamber through the air/gas circulation inlet 302 can flow over, around, and through the pouch without significant impediment.

O. Activation Pouch

Figure 13:
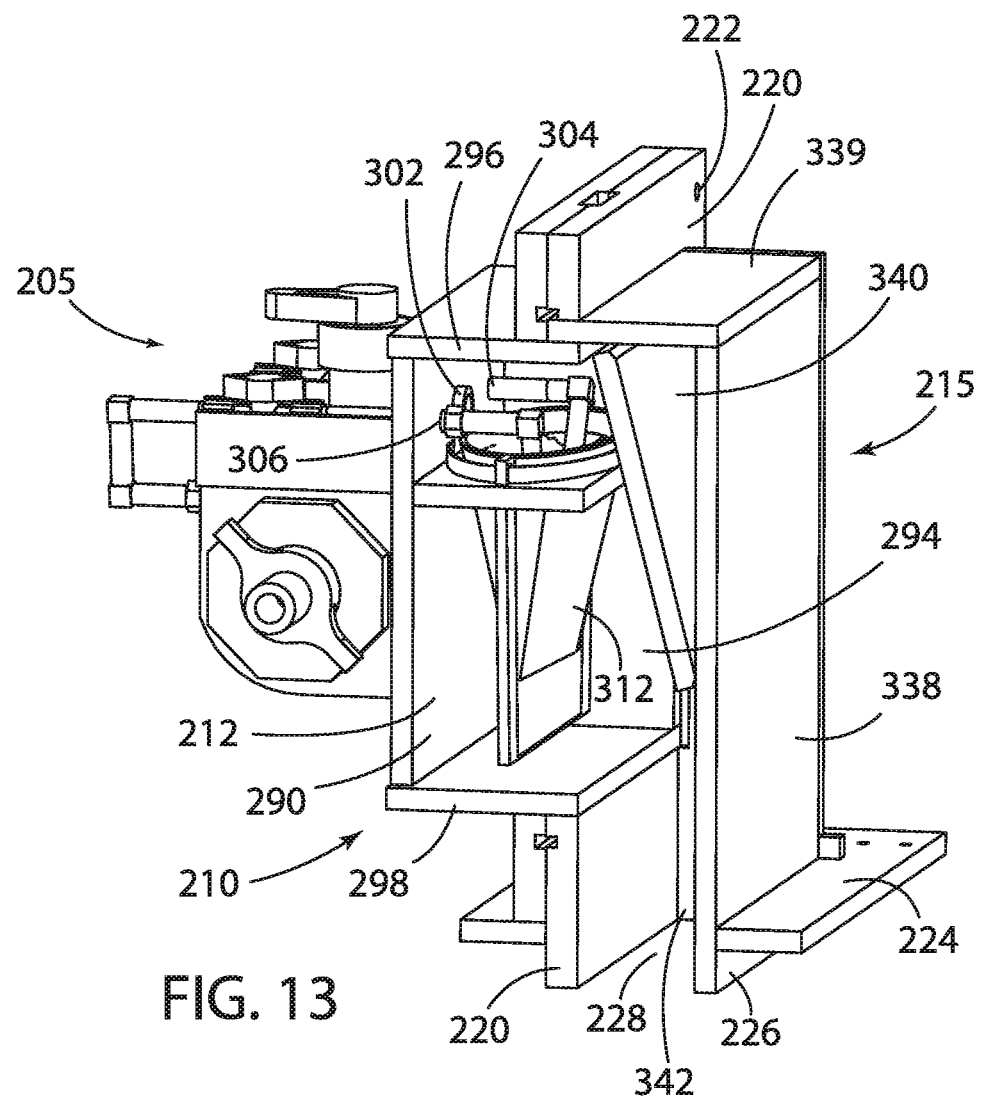
FIG. 13 is a cross-sectional cutaway view of a $ClO_2$ fumigant activation unit according to an example embodiment with an activation pouch in the activation chamber.
Figure 14:
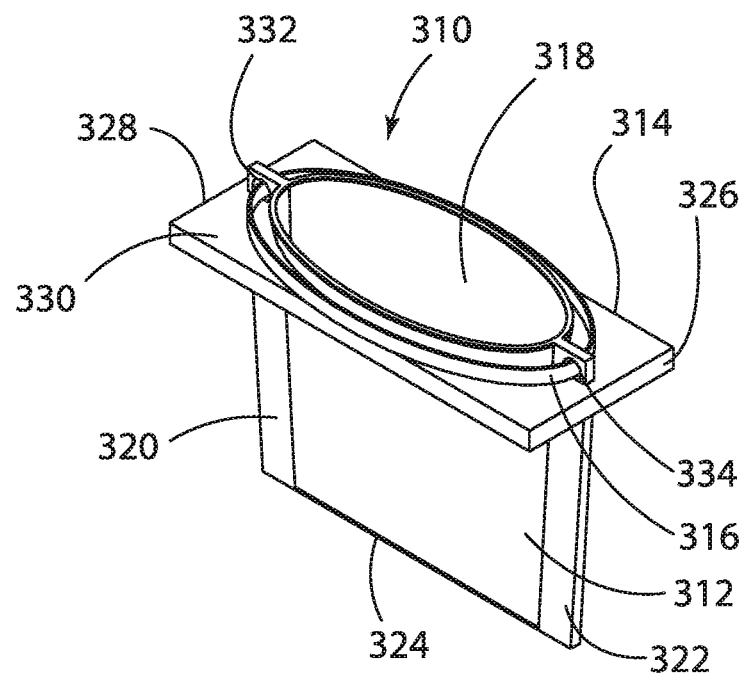
FIG. 14 is a perspective view of an activation pouch according to an example embodiment.
Figure 14A:
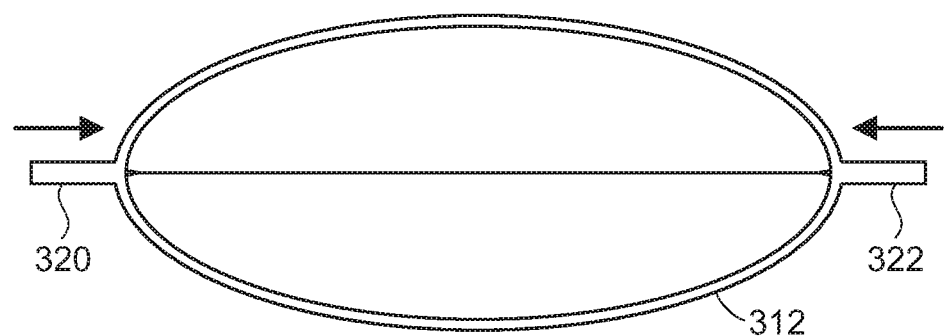
FIG. 14A is a top plan view of an activation pouch according to an example embodiment with inward force applied to opposite sides.
Figure 14B:
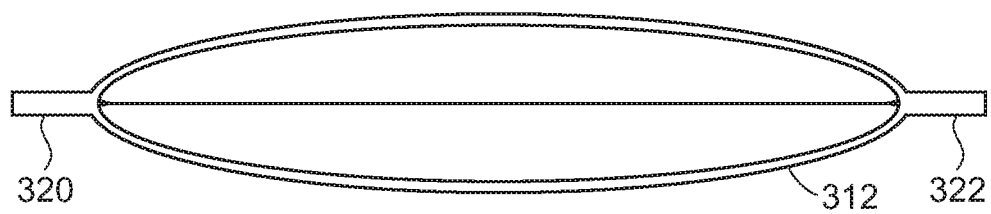
FIG. 14B is a top plan view of an activation pouch according to an example embodiment.

As best seen in FIGS. 14, 14A, and 14B taken together with FIGS. 11 and 13, a preferred activation pouch assembly 310 comprises an activation pouch body 312, an activation pouch holding plate 314, and an activation pouch retaining ring 316. The activation pouch body 312 has an open top 318, a closed bottom 324, and opposing sides 320 and 322 with sealed edges. The pouch body 312 preferably is trapezoid shaped for reasons that will become apparent from the description below.

The activation pouch 312 is preferably formed from substantially the same type of material having substantially the same characteristics as described above with respect to activation cup 13. For example, the activation pouch may be formed of a multi-layer filter material comprising a layer of non-woven media and a PTFE liner layer adhered together in a sheet. Like the activation cup 13, the material from which activation pouch 312 is formed has the benefit of being permeable to air and $ClO_2$ gas but substantially impermeable to water and reaction by-products. Suitable materials are available commercially from a number of manufacturers.

A substantial improvement is that the activation pouch 312 is simple and inexpensive to produce with no molding operations being required. In one variation, the activation pouch body 312 is formed from a single piece of material. Generally, a flat piece of the material is cut or otherwise formed in the desired shape of the pouch with the desired width of the finished pouch but with approximately twice the desired height of the finished pouch. The material is then folded in half in the height direction and the opposing side edges are bonded, preferably continuously along the entirety of their length from the top of the pouch to the bottom, to form a substantially fluid-tight seal along the entire side edges. The side edges may be sonically welded using a sonic welding bar and anvil. Other alternatives such as thermal bonding may also be used, so long as they produce a substantially fluid-tight seal. As best seen in FIG. 14, this process produces a leak-proof pouch body with an open top 318, opposing sides 320, 322 with sealed edges, and a closed bottom 324 comprising a continuous piece of folded pouch material. The continuously bonded side edges also impart a degree of rigidity to the structure of the pouch body.

In the preferred trapezoid-shaped embodiment, the width of the top of the pouch body is greater than the width of the bottom, and the side edges extend linearly from the top to the bottom. To produce this embodiment, a flat piece of the pouch material is cut or otherwise formed as described above, but in the shape of two mirror image trapezoids with a common bottom. The material is then folded in half and the side edges continuously bonded as described above to form the trapezoid shaped pouch 312 shown in FIG. 14. The same process may be used to form pouch bodies with various other geometric shapes including squares, rectangles, cones, and others.

In another variation, the activation pouch body 312 may be formed by first overlaying two adjacent rolls or discrete pieces of flat material having the desired width of the pouch body. The overlaid rolls or pieces of flat material are then sealed together as described above in locations and with orientations corresponding to the desired side edges of the pouch body. The material is then cut to the desired height of the pouch body and the bottom is sealed, leaving the top open. It is contemplated that this alternative approach may be well suited for automatic manufacturing. Like the first variation, this variation may be used to form pouch bodies of various geometric shapes including trapezoids, squares, rectangles, and cones.

Regardless of the manner of manufacture, those skilled in the art will appreciate that the pouch may be formed in various sizes to accommodate more or less dry reagent and water, and to enable more or less $ClO_2$ fumigant to be generated. The size of the pouch thus depends on the application, including the size, surface area and volume of the items and spaces to be decontaminated.

The activation pouch holding plate 314 is designed to retain the activation pouch 312 as best seen in FIG. 14. The holding plate 314 is a substantially flat substantially rectangular plate with opposing edges 326, 328 and a top surface 330. The top surface 330 has an opening (not shown) which is preferably in the shape of an elongated oval. Small slits (not shown) extend outwardly from the opposing longitudinal ends of the opening substantially on the longitudinal axis of the opening. Preferably the longitudinal dimension of the opening is somewhat greater than the width of the bottom of the trapezoid shaped pouch body 312 and somewhat less than the width of the top. As a result, the bottom 324 of the pouch 312 can be inserted through the opening with the bonded edges of the opposing sides 320, 322 engaged in the slits. However, as the pouch 312 is further inserted through the opening, the bonded edges of the opposing sides 320, 322 are engaged and squeezed together by the inner edges of the opening. This causes the pouch to flex open at the top 318 and the trapezoid shaped side surfaces to bow outward in a substantially oval shape determined by the elongated oval shape of the opening as shown in FIG. 14A. The expansion of the opening facilitates the introduction of reagents, water, and neutralizing solution to the pouch body, creates a volume of open space within the interior of the pouch body for efficient $ClO_2$ gas generation reactions to take place, and facilitates the efficient escape of the generated $ClO_2$ gas from the pouch.

The length, width, and thickness dimensions of the holding plate are selected so that the holding plate 314, together with the retained activation pouch 312, can be slid into, mounted in, and retained within the chamber 290 of the activation chamber 210 with the opposing edges 326, 328 of the holding plate captured in and supported by the slots 308 in the interior surfaces of the opposing side walls 292, 294 of the chamber. Similar to the other components of the fumigant activation unit, the activation pouch holding plate 314 is preferably constructed of a chemical resistant and non-static material such as PVC or a similar plastic.

It will be appreciated by those skilled in the art that the holding plate 314 can be dimensioned and provided with openings to retain multiple activation pouches. Similarly, the activation chamber and slots 308 can be dimensioned to accommodate such a modified holding plate such that multiple activation pouches can be positioned in the activation chamber simultaneously. With the provision of suitable additional water and air bubbler conduits and valves for the additional pouches, such an arrangement allows the fumigant activation unit 200 to be used multiple times without requiring disassembly to replace the activation pouch and dry reagent.

The activation pouch retaining ring 316 extends around the periphery of the top of the pouch 312 near and preferably just below the open top 318. Retaining openings 332 and 334 are formed in the bonded edges of opposing sides 320, 322 of the pouch body 312 just below their top edges. The retaining ring is looped through the retaining openings 332 and 334 to form a loop that preferably is slightly larger than the opening in the holding plate 314 when the pouch 312 is fully inserted in the opening. The retaining ring engages the top surface 330 of the holding plate 314 at this point and retains the activation pouch within the opening of the holding plate while preventing the pouch from sliding completely through the opening. The retaining ring 316 also assists in maintaining the substantially oval shape of the opening and interior volume of the pouch once reagents and water are added and while reactions are taking place. The retaining ring can also be used to suspend or otherwise position or locate the pouch in an activation chamber. A nylon or other plastic zip tie is suitable to use as retaining ring 316.

P. Back Plate

The back plate 215 provides an air/gas conduit between the activation chamber 210 and a vent of an air distribution system, such as duct work of an HVAC or similar system, that distributes $ClO_2$ decontamination fumigant generated in the activation chamber to an area or areas to be decontaminated. Referring primarily to FIGS. 8, 11, and 13, and as previously described, one variation of the back plate includes a mounting plate 224 with a vent adaptor 226 for interfacing to a vent of the air distribution system in any of a plurality of different orientations. Also as previously described, the back plate 215 includes a frame 220 that extends around the periphery of the back plate and that is adapted to fit in a flush air/gas tight sealed arrangement with a corresponding frame 216 of the activation chamber 210 when the fumigant activation unit 200 is assembled.

The back plate 215 further comprises an air/gas inlet opening 336, defined by the frame 220, and an air/gas conduit between the inlet 336 and the air/gas outlet opening 228 in the mounting plate 224. The inlet 336 is intended to align with and be in air/gas communication with the open front of the chamber 290 in the activation chamber 210 when the fumigant activation unit 200 is assembled. The air/gas conduit is defined by a back wall 338, first and second opposing side walls 342, 344, and a top wall 339. The bottom of the air/gas conduit is the air/gas outlet opening 228. The back wall 338, opposing side walls 342, 344, and lower portion of the frame 220 extend slightly through the mounting plate 224 to form the vent adaptor 226. Within the air/gas conduit is an air/gas deflection plate 340. The air/gas deflection plate 340 slants inwardly from the back wall 338 toward the opening 336 and functions to help deflect air/gas flowing from the activation chamber and direct it into the air/gas conduit and toward the air/gas outlet opening 228.

As previously mentioned, in another variation of the back plate 215 the vent adaptor 226 may be eliminated from the mounting plate 224 and the air gas outlet opening 228 may be resized and reoriented as desired or necessary to allow the back plate 215 to be mounted to a surface other than a vent of an HVAC duct. The vent adaptor can be eliminated by simply terminating the back wall 338, opposing side walls 342, 344, and lower portion of the frame 220 flush with the mounting plate 224. In this variation, the mounting plate is 224 is mounted to the surface positioned so that the air/gas outlet opening 228 of the activation chamber 210 is in sealed air/gas communication with an opening in the surface. The mounting plate may be affixed to the surface using suitable fasteners. Gasket or other sealant material may be used to help seal the interface between the mounting plate and the surface and prevent air/gas leakage.

Q. $ClO_2$ Fumigant Activation Unit Method of Operation

Similar to the embodiments of the invention described above, the $ClO_2$ fumigant activation unit 200 can be operated and used to generate a $ClO_2$ decontamination fumigant, direct it to an area and/or items to be decontaminated, stop the $ClO_2$ reaction, and neutralize remaining $ClO_2$ fumigant. Initially, the activation pouch assembly 310 is inserted into the activation chamber 210 with the edges 326, 328 of the activation pouch holding plate 310 engaged and supported in the slots 308 of the chamber 290. In this position, the open ends of the metered water conduit 232 and air bubbler conduit 236 of the activator 205 extend partially into the activation pouch 324 through its open top 318, and the air/gas circulation inlet opening 302 of the activation chamber 210 is approximately centered on and slightly above the open top 318. A desired amount of $ClO_2$ generating reagent is added to the activation pouch 312. The activation chamber 210 and the back plate 215 are then sealed closed as described previously.

The valve 234 in the metered water conduit, the valve 238 in the air bubbler conduit, and the air/gas circulation valve 242 are initially closed. A source of metered water is connected to the fitting 278 of the metered water conduit 232. The source of metered water may be a syringe or the like if desired. If the fumigant activation unit is to operate as an open-loop decontamination system, the fitting 266 and/or conduit 268 connected to the air/gas inlet 260 of blower 230 is left exposed to the ambient. If the fumigant activation unit is to operate as a closed-loop decontamination system, the fitting 266 and/or conduit 268 are connected in fluid communication with the area or item to be decontaminated. Next, the valve 234 is opened to add a small amount of water to the activation pouch 312 and then closed again. The reaction solution of the water and the dry reagents begins to generate essentially pure $ClO_2$ gas. The blower 230 is energized at relatively low speed and the valve 238 in the air bubbler conduit 236 and the air/gas circulation valve 241 are opened. This introduces a relatively low speed air flow into the activation pouch which agitates the reaction solution and causes it to bubble, thereby further enhancing the $ClO_2$ gas generating reaction and efficiently forcing nearly all of the $ClO_2$ gas out of the water solution and into the activation chamber.

The generated $ClO_2$ gas naturally wants to flow toward an area of least pressure resistance. Hence, it naturally flows out the expanded open top 318 of the activation pouch 312 and into the chamber 290 of the activation chamber 210. The generated $ClO_2$ gas flowing out the open top of the activation pouch relieves the head pressure within the pouch resulting from the on-going $ClO_2$ gas generating reaction, which results in an even more efficient reaction and maximizes the volume and concentration of $ClO_2$ gas that is produced from the solution.

With the air/gas circulation valve 242 opened, the air blower 230 blows air into the chamber 290 through the air/gas circulation opening inlet 302. Because the activation pouch 312 is effectively suspended in the chamber 290 and is permeable to air and gas, the air from air blower 230 flows both around and through the activation pouch, further enhancing the reaction. The air flow also entrains the generated $ClO_2$ gas escaping from the open top 318 of the activation pouch 312 thus producing a decontamination fumigant and directs the fumigant into the back plate 215 and out through the air/gas outlet opening 228 into a vent or other opening to which the mounting plate 224 is interfaced. Alternatively, if a back plate 215 is not used, the air flow directs the fumigant directly from the activation chamber to the opening in the surface to which the activation chamber is mounted. From there, the fumigant is carried to an area and/or items to be decontaminated. By maintaining the air speed relatively low during the decontamination fumigant generation and distribution process, the production of $ClO_2$ gas is enhanced and the efficacy of the decontamination fumigant is not substantially degraded as it is directed and distributed to the areas and items to be decontaminated.

The air blower 230 remains energized and the valves 238 and 241 remain open until the $ClO_2$ gas generating reaction is substantially completed and all or a substantial volume of the resulting decontamination fumigant is distributed to the area or item to be decontaminated. The blower 230 may then be de-energized and the valves 238 and 241 closed. Alternatively, if the fumigant activation unit is connected in a closed-loop configuration, the blower 230 may continue to run and the valves 238 and 241 may remain open if it is desired to continuously recirculate the decontamination fumigant between the fumigant activation unit and the area or item to be decontaminated.

Similar to other embodiments of the invention, any commercially available dry reagents for generating the $ClO_2$ gas are suitable for use in the fumigant activation unit 200. These include effervescent dry reagent tablets comprising sodium chlorite and sodium dichloroisocyanurate dihydrate, which are available from BASF, Quip Laboratories, Inc. of Wilmington, Del., Beckart and other sources. Because the $ClO_2$ gas generating reaction proceeds so efficiently and completely in the open top activation pouch 312 suspended in the fumigant activation unit 200, little water is required to be added to the activation pouch 312 to support the reaction. Accordingly, little or no moisture is entrained in the air flow with the essentially pure $ClO_2$ gas. As a result, adverse effects due to inclusion within the fumigant of chlorine gas, chlorine-based acids, reaction by-product salts and excess moisture are substantially eliminated. What small amount of water and reaction by-products are left over from the reaction remain trapped in the activation pouch 312 and can be properly disposed of at a later time.

The generation of $ClO_2$ gas can be halted at any time, if desired, by introducing a neutralizing solution into the activation pouch 312. To do this, the valve 234 in the metered water conduit 232 is closed. The source of metered water is removed from the fitting 278 and replaced by a source of neutralizing solution. The valve 234 is then opened to introduce the neutralizing solution into the activation pouch 312 and immediately closed again. As described previously, a suitable neutralizing agent is a solution of sodium thiosulfate.

Those skilled in the art will realize that the size of the activation pouch 312, the activation chamber 290, etc. can be scaled up or down as needed for the particular decontamination application. Similarly, the amount of water and reagents employed can be varied depending on the desired fumigant concentration and volume, the size/volume of the area to be decontaminated, and the amount of decontamination time desired. In addition, flexible control is maintained over the process even while it is underway. For example, additional water may be added at any time to produce a higher volume or higher concentration of $ClO_2$ gas, or neutralizing solution may be added to discontinue the further generation of $ClO_2$ gas and, if desired and if the system is configured in a closed-loop, to neutralize the decontamination fumigant already produced.

Typically once the $ClO_2$ generation reaction has completed or been stopped and the decontamination fumigant has been directed to the areas and/or items to be decontaminated, the fumigant is allowed to remain resident for a desired dwell or residential time sufficient to obtain the desired decontamination. During this time, the air blower 230 typically is de-energized and valves 238 and 241 are closed.

After the desired dwell time has elapsed, the remaining decontamination fumigant may be directed to a central neutralizing area like the neutralizing area 7 in the example embodiment of FIG. 4. An additional blower and conduits (not shown) which are either separate or a part of the central neutralizing area may be used to draw the remaining fumigant from the decontaminated area into the neutralizing area. Alternatively, or in addition, if the fumigant activation unit 200 is connected in an open-loop configuration with the air/gas inlet 260 of air blower 230 exposed in the ambient, the air blower 230 can be energized and air/gas circulation valve 241 opened to blow ambient air through the back plate 215 (or directly) into the decontaminated area to dilute the remaining fumigant and help direct it to the neutralizing area.

Also alternatively, or in addition, if the fumigant activation unit 200 is configured (or can be configured) in a closed-loop with the air/gas inlet 260 of air blower 230 in fluid communication with the decontaminated area, the fumigant activation unit may be operated to recirculate and neutralize the remaining decontamination fumigant. To do so, valves 234, 236, and 241 are closed. A source of neutralizing solution is connected to the conduit 232 via the fitting 278. The source of neutralizing solution may be a syringe for example. The fitting and/or conduit 266, 268 of air blower 230 is connected by hose, conduit, or another air/gas passage to the area that was decontaminated and that retains residual $ClO_2$ fumigant to be neutralized. The air blower 230 is energized at a relatively high speed and the air/gas circulation valve 241 is opened. Suction created by the blower 230 at the fitting 266 and/or conduit 268 causes the remaining fumigant to be drawn from the decontaminated area through the air blower and to recirculate through the air/gas circulation fitting 240, air/gas circulation opening 302, activation chamber 210 and back plate 215 (if present) back to the area decontaminated. The valve 234 is opened to introduce neutralizing solution into the activation pouch 312 in the activation chamber and then closed. The $ClO_2$-containing fumigant is neutralized by the solution as it passes through and around the activation pouch while recirculating through the activation chamber. The relatively high speed at which the air is recirculated assists in disrupting the $ClO_2$ molecules and facilitating the neutralization. Additional neutralizing solution can be added to the activation pouch from time to time as needed by opening the valve 234 in conduit 232, adding the desired quantity of additional neutralizing solution, and then closing the valve.

In either alternative, $ClO_2$ sensors may be used at one or more locations in the areas that were decontaminated and/or in the air distribution system to detect the remaining concentration of $ClO_2$ in the fumigant. Once the concentration of $ClO_2$ reaches an acceptable level, the neutralizing operation is complete.

R. Sealed Package/Contents Sterilization System and Method

There is a particular need in the health and medical industries for assurance that medical instruments, such as scalpels, infusion pumps, endoscopes, and the like are completely sterilized before being used in a medical procedure. A challenge is presented because some such instruments include small openings and lumens that can harbor microbes in the interstices of the instruments. Complete sterilization to remove such microbes can be difficult. Another challenge is presented because instruments may be transported between various locations after they are sterilized and before they are used and may be handled by various persons. For example, an endoscope may be sterilized in one location and then stored in another before being transported to a treatment location for use. Instruments that have been sterilized can become contaminated again in the process and, even if they do not actually become contaminated again, there can be no assurance that they remain sterile at the time they are ultimately used with a patient.

Figure 15:
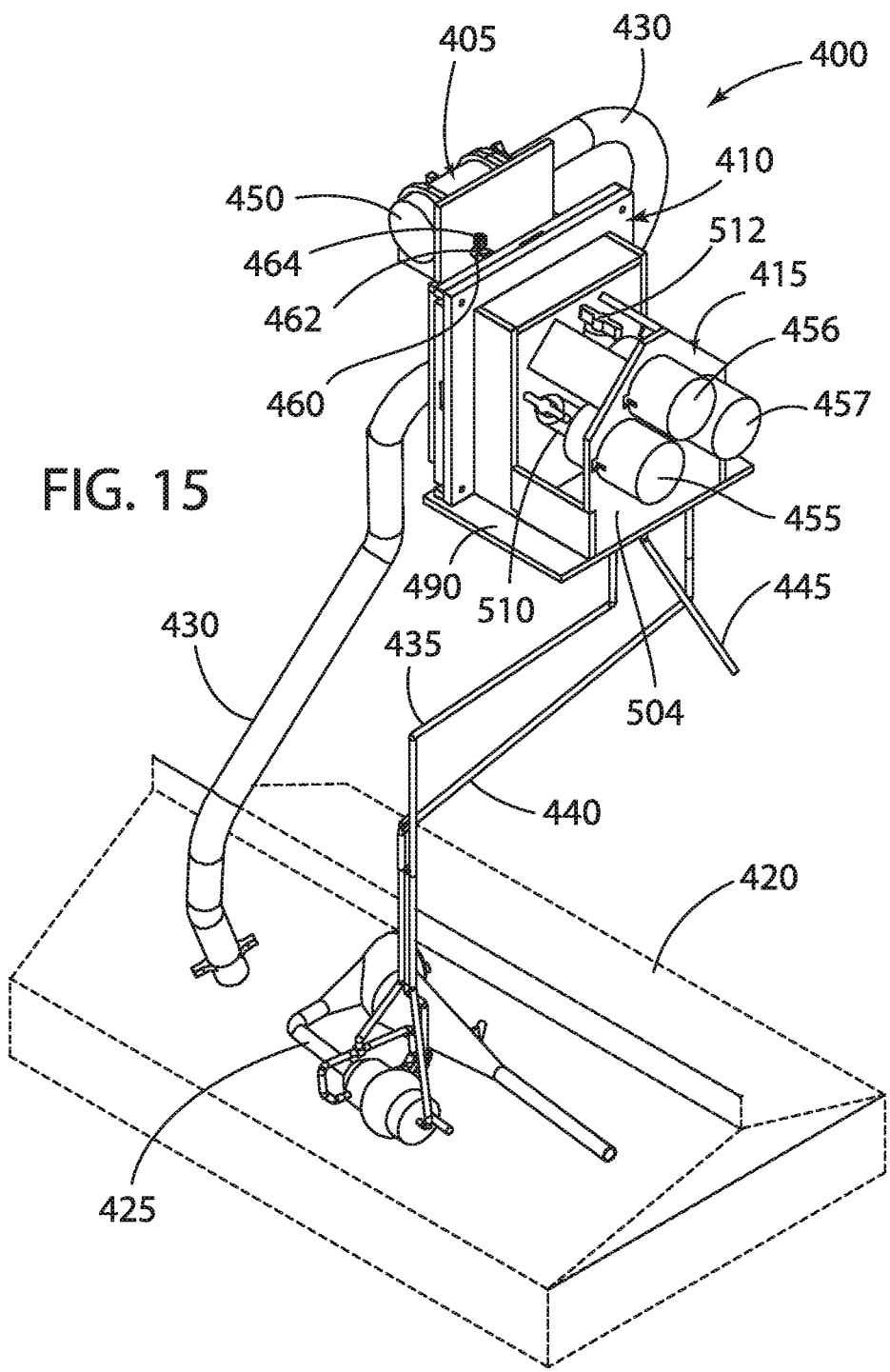
FIG. 15 is a rear perspective view of a $ClO_2$ sterilization system according to an example embodiment connected by conduits to an item to be sterilized within a sealed package.
Figure 16:
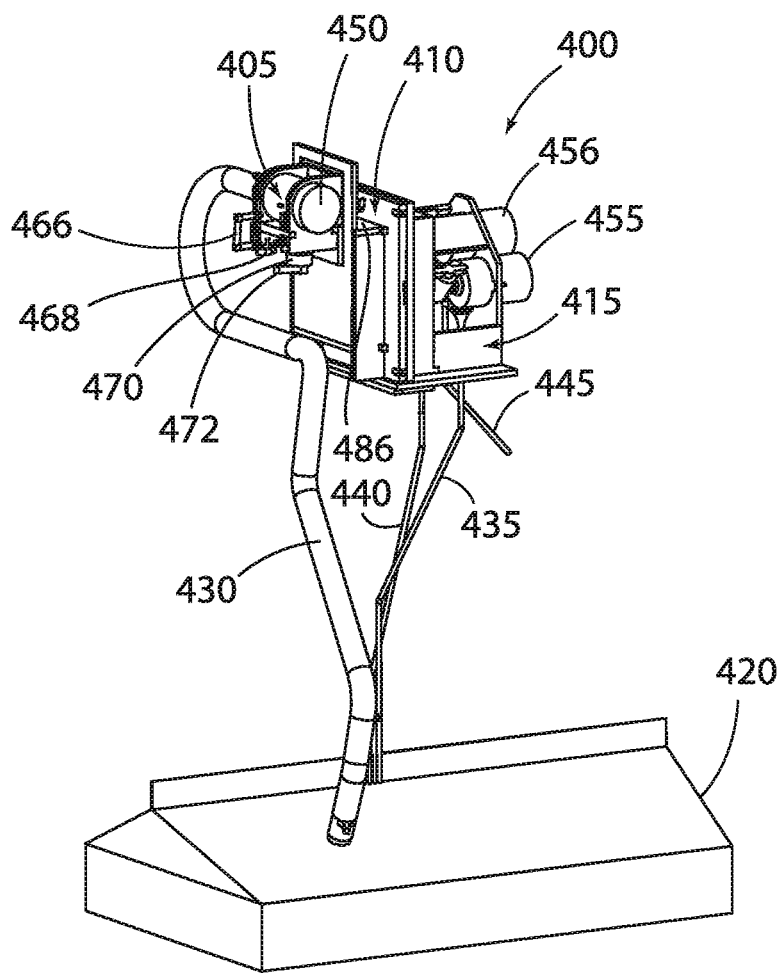
FIG. 16 is a front perspective view of a $ClO_2$ sterilization system according to an example embodiment connected by conduits to a sealed package.

FIGS. 15-16 illustrate an example embodiment of a $ClO_2$ sterilization system that is adapted for sterilizing objects enclosed in sealed packages as well as the packages themselves. The example embodiment can be employed in numerous settings including laboratories, field facilities, buildings, hospitals, clinics, veterinary facilities, nursing homes, day care facilities, urgent care facilities, and many others. It has numerous applications including sterilizing marine items, military items, perishable goods, hazmat contaminated items, and others. As described below, the example $ClO_2$ sterilization system is particularly well adapted to sterilize medical instruments contained in sealed packages, including the small internal openings, lumens, and other interstices of certain medical instruments, such as endoscopes and the like. Also as described below, the example $ClO_2$ sterilization system can be adapted to sterilize not only the contents of the packages but also the packages themselves if desired. The example sterilization system is thus able to provide assurance that a medical instrument remains completely sterile at the time of use despite the package enclosing it having been handled by various persons, moved between various locations, and stored for a period of time since the instrument was sterilized.

The $ClO_2$ sterilization system comprises a $ClO_2$ fumigant activation unit 400 that includes an activator 405, an activation chamber 410, and a back plate 415. The activator 405 and activation chamber 410 are substantially similar in structure and function to the activator 205 and activation chamber 210 respectively of the example $ClO_2$ fumigant activation unit 200 described above, with several variations pointed out below. The back plate 415 also is substantially similar in structure and function to the back plate 215 of the fumigant activation unit 200 described above, but with a few unique differences and additions described in detail below.

The $ClO_2$ fumigant activation unit 400 is adapted to interface with a sealed package 420, which in turn is adapted to contain an item to be decontaminated. In the particular example illustrated in FIG. 15, the package 420 encloses an endoscope 425 to be decontaminated. Air/gas conduit 430 interfaces an air/gas inlet port of blower 450 of the activator 405 with a port (not shown) of the package 420. Air/gas conduits 435 and 440 interface air/gas blowers 455 and 457 of the back plate 415 with openings in the endoscope 425 through ports (not shown) in the package 420, and air/gas conduit 445 also is available to interface an additional air/gas blower 456 of the back plate 415 as necessary or desired.

Like the fumigant activation unit 200 described above, the fumigant activation unit 400 is operative to selectively generate $ClO_2$ gas to produce a decontamination fumigant, and to direct the decontamination fumigant to an area to be decontaminated at a selected concentration and for a selected dwell time. In the case of the $ClO_2$ sterilization system, the area to be decontaminated is the interior of the sealed package 420 and its contents, e.g., endoscope 425. Also, like fumigant activation unit 200, fumigant activation unit 400 is operative to selectively halt the generation of $ClO_2$ fumigant with a neutralizing solution and to selectively recirculate residual $ClO_2$-containing fumigant between the fumigant activation unit 400 and the sealed package 420 while neutralizing the fumigant if desired.

Figure 20:
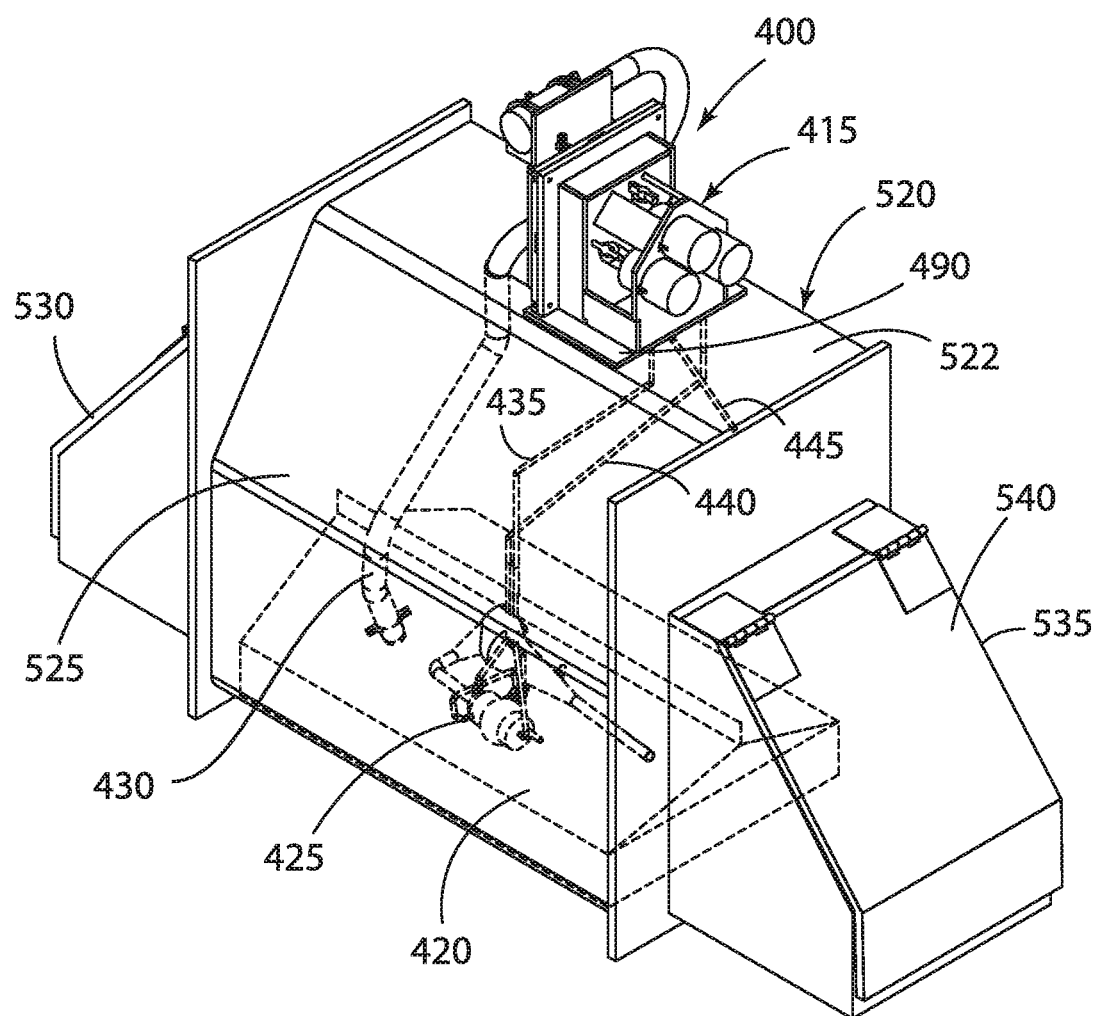
FIG. 20 is a perspective view of a $ClO_2$ sterilization system according to an example embodiment with a sealed enclosure containing a sealed package enclosing an item to be sterilized, and internal tubing in the item.

The example fumigant activation unit 400 illustrated in FIGS. 15-16 is shown directly interfaced with the sealed package 420 and is adapted to sterilize the interior of the package and contents. However, as illustrated in FIG. 20, fumigant activation unit 400 also may be interfaced with a sealed enclosure and adapted to sterilize not only the interior and contents of the sealed package, but the sealed package itself. Further, the fumigant activation unit 400 may be used as a standalone unit for generating and neutralizing $ClO_2$ decontamination fumigant with or without a separate neutralizing area, such as the separate neutralizing area 7 described above in connection with the example embodiment of FIG. 3.

The fumigant activation unit 400 is assembled as a sealed unit in essentially the same way as fumigant activation unit 200 described above. The assembly details are not repeated here, but generally the activator 405 is mounted to a back wall of the activation chamber 410, and the activation chamber 410 is assembled in a sealed flush relationship with the back plate 415, as best illustrated in FIGS. 16A-16D, such that decontamination fumigant generated in the activation chamber 410 may be directed through the back plate 415 to the sealed package 420 and its contents, such as endoscope 425. One difference between the assembly of fumigant activation unit 400 compared to fumigant activation unit 200 is that the activator 405 is mounted to the back of the activation chamber 410 rotated by 180 degrees such that the conduit 466 and valve 468 for providing air for bubbling the $ClO_2$ generating reaction solution, and the valve 472 for providing air/gas circulation into and through the activation chamber, which are described further below, are routed beneath the blower 450 rather than over it.

S. Activator

Figure 17:
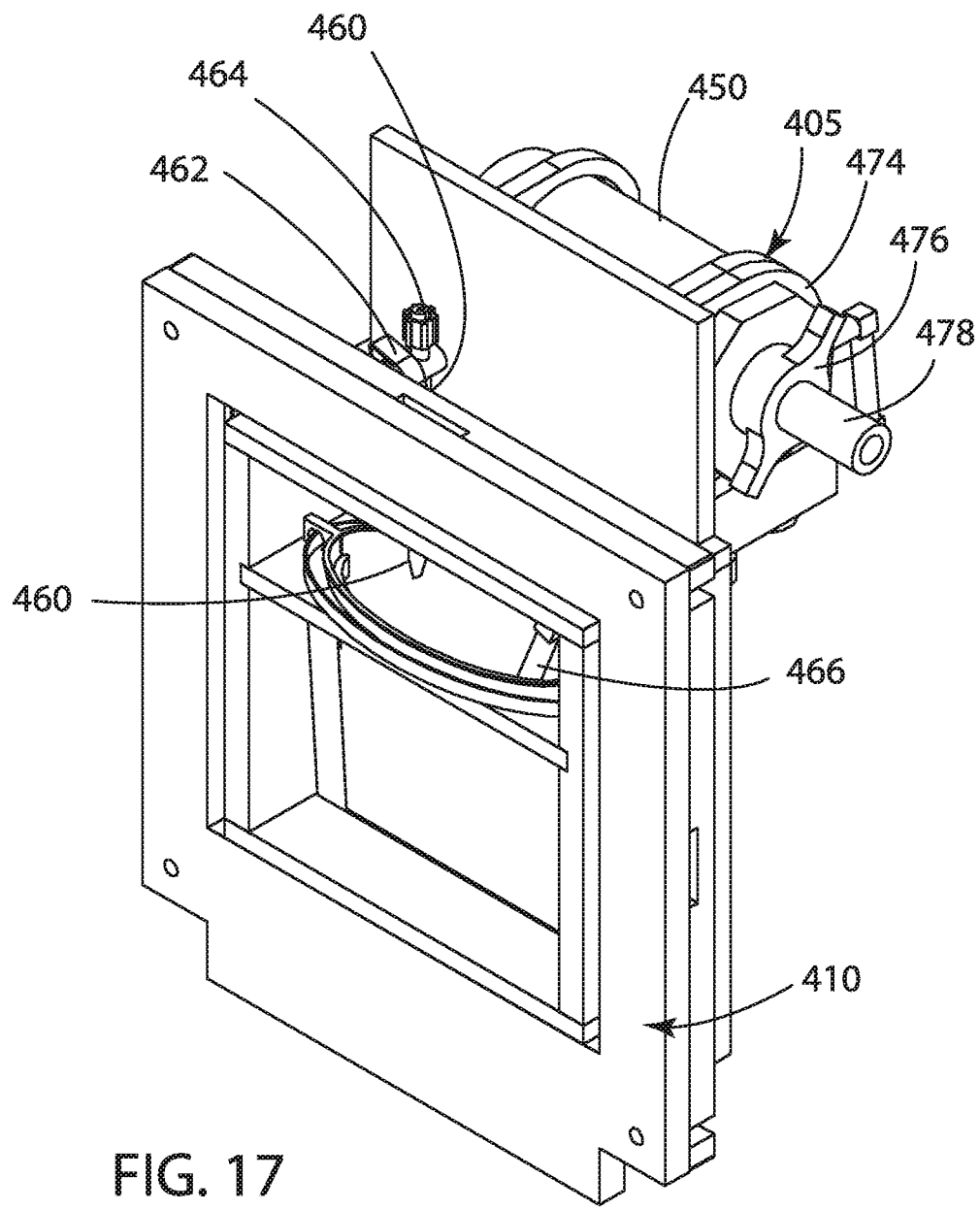
FIG. 17 is a front perspective view of an activation chamber and activator of a $ClO_2$ sterilization system according to an example embodiment.

Referring primarily to FIGS. 15-17, the activator 405 comprises an air/gas blower 450, metered water conduit 460 and valve 462, air bubbler conduit 466 and valve 468, and air/gas circulation valve 472. Each of these components has substantially the same structure and characteristics as, and functions substantially the same as, the corresponding component of the activator 205 described above, with a couple exceptions noted below. Blower 450 is mounted to the back wall of the activation chamber 410 rotated by 180 degrees such that the air bubbler conduit 466 and valve 468, and the air/gas circulation valve 472 are routed under the blower 450 to the activation chamber 410 rather than over the blower as in fumigant activation unit 205. In addition, metered water conduit 460 and valve 462 are not mounted on the activator, but are mounted on a top wall 486 of the activation chamber 410.

The air/gas blower 450 has an air/gas inlet port 474 and a first air/gas outlet port (not shown—hidden by the air gas blower 450). The air/gas inlet port 474 connects via a fitting 476 to a conduit 478. The conduit 478 in turn may be connected via a suitable fitting (not shown) to an air/gas conduit 430 for connection to the sealed bag 420. Alternatively, air/gas conduit 430 may be connected directly to the air/gas inlet port 474 via a suitable fitting. The first air/gas outlet port connects to the air/gas circulation valve 472 as further described below.

The air/gas circulation valve 472 resides within a body 470 having an air/gas inlet port and an air/gas outlet port. An internal passageway connects the ports. The valve 472 is positioned in the body 470 between the ports. The inlet port connects to the first air/gas outlet port of the blower 450. The outlet port connects to an air/gas circulation inlet opening 480 in the back wall of the activation chamber 410. Preferably both connections are sealed using O-rings and/or a suitable sealant to prevent air/gas leaks. The air/gas circulation valve 472 is operable to selectively open and close the passageway between the air/gas inlet and outlet ports and thereby to control the flow of air/gas between the air/gas inlet port 474 of the blower 450 and the air/gas circulation inlet 480 of the activation chamber.

A first open end of the air bubbler conduit 466 is connected by a fitting to a passageway in air/gas communication with the air/gas inlet port 474 of the air/gas blower 450 in the same manner as described above with respect to the air bubbler conduit 236 of the activator 205 of fumigant activation unit 200. From there, the conduit is routed beneath the air/gas blower 450 to an opening 482 in the back wall 484 of the activation chamber 410. The conduit extends through the opening 482 into the interior of the activation chamber 410. A second open end of the conduit is positioned in the interior of the activation chamber 410 preferably extending through the open top of the activation pouch at least partially into the body of the pouch as shown in FIG. 17. Preferably the opening 482 is sealed around the conduit via suitable fittings and/or a suitable sealant material to prevent air/gas leaks. Various fittings also may be used to facilitate routing the conduit 466 under the air/gas blower 450, through the opening 482, and into the interior of the activation chamber 410 with the second open end extending through the open top of the activation pouch at least partially into the body of the pouch. The valve 468 is located in-line in the conduit 466 between the air/gas inlet port of the blower 450 and the opening 482 in the back wall 484 of the activation chamber 410.

The metered water conduit 460 and valve 462 are positioned atop a top wall 486 of the activation chamber 410. The conduit 460 has a first open end with a fitting 464 for connection to a source of metered water or neutralizing solution (not shown) and an opposite second open end. The conduit 460 extends through an opening 488 in the top wall 486 of the activation chamber 410 and into the interior of the activation chamber preferably with the second open end of the conduit 460 extending through the open top of the activation pouch at least partially into the pouch body. Preferably the opening 488 is sealed around the conduit 460 via suitable fittings and/or a suitable sealant material to prevent air/gas leaks. The valve 462 is located in-line in the conduit between the first open end and the opening 488 in the top wall 486 of the activation chamber 410.

T. Activation Chamber and Activation Pouch

Figure 18:
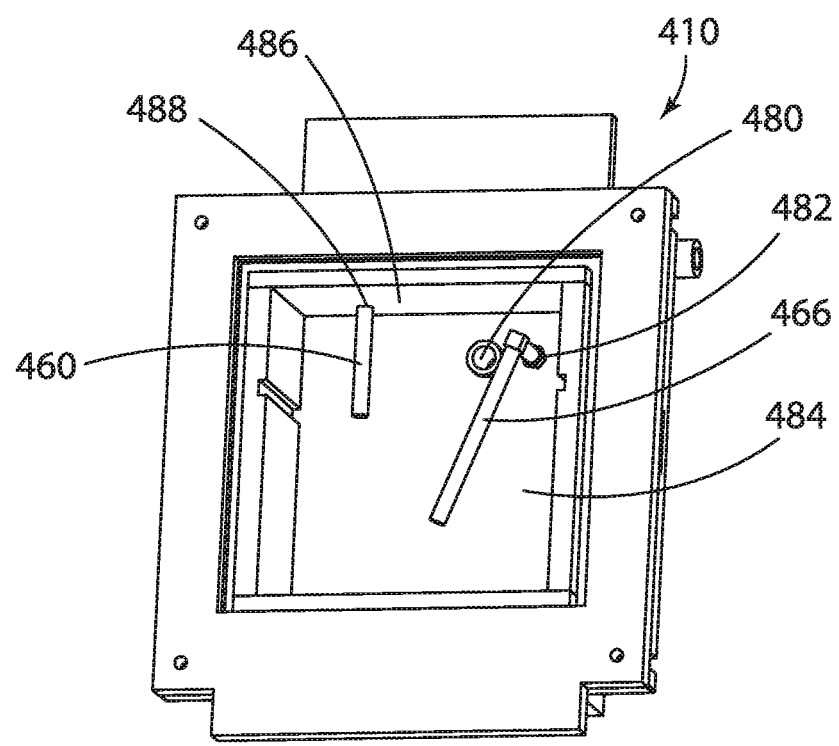
FIG. 18 is a front view of an activation chamber of a $ClO_2$ sterilization system according to an example embodiment.

The activation chamber 410, which is best shown in FIGS. 17-18, has substantially the same structure as and functions in substantially the same manner as the activation chamber 210 of the fumigant activation unit 200 described above. Accordingly, those details are not repeated here. One difference is that the metered water conduit 460 enters activation chamber through an opening 488 in the top wall 486 of the activation chamber, rather than through the back wall 484.

The activation pouch assembly and activation pouch shown in FIG. 17 mounted and suspended in activation chamber 410 are identical to the activation pouch assembly 310 and activation pouch 312 illustrated in FIG. 14 and described in detail above. The activation pouch assembly also mounts in the activation chamber 410 using the same structures and in the same manner as described above with respect to activation chamber 210 of fumigant activation unit 200. Thus, those details also are not repeated here.

U. Back Plate

The back plate 415 of the fumigant activation unit 400 has substantially the same structure as and functions in substantially the same manner as the back plate 215 of the fumigant activation unit 200 described above, but with a few unique differences and additions described below.

Figure 19:
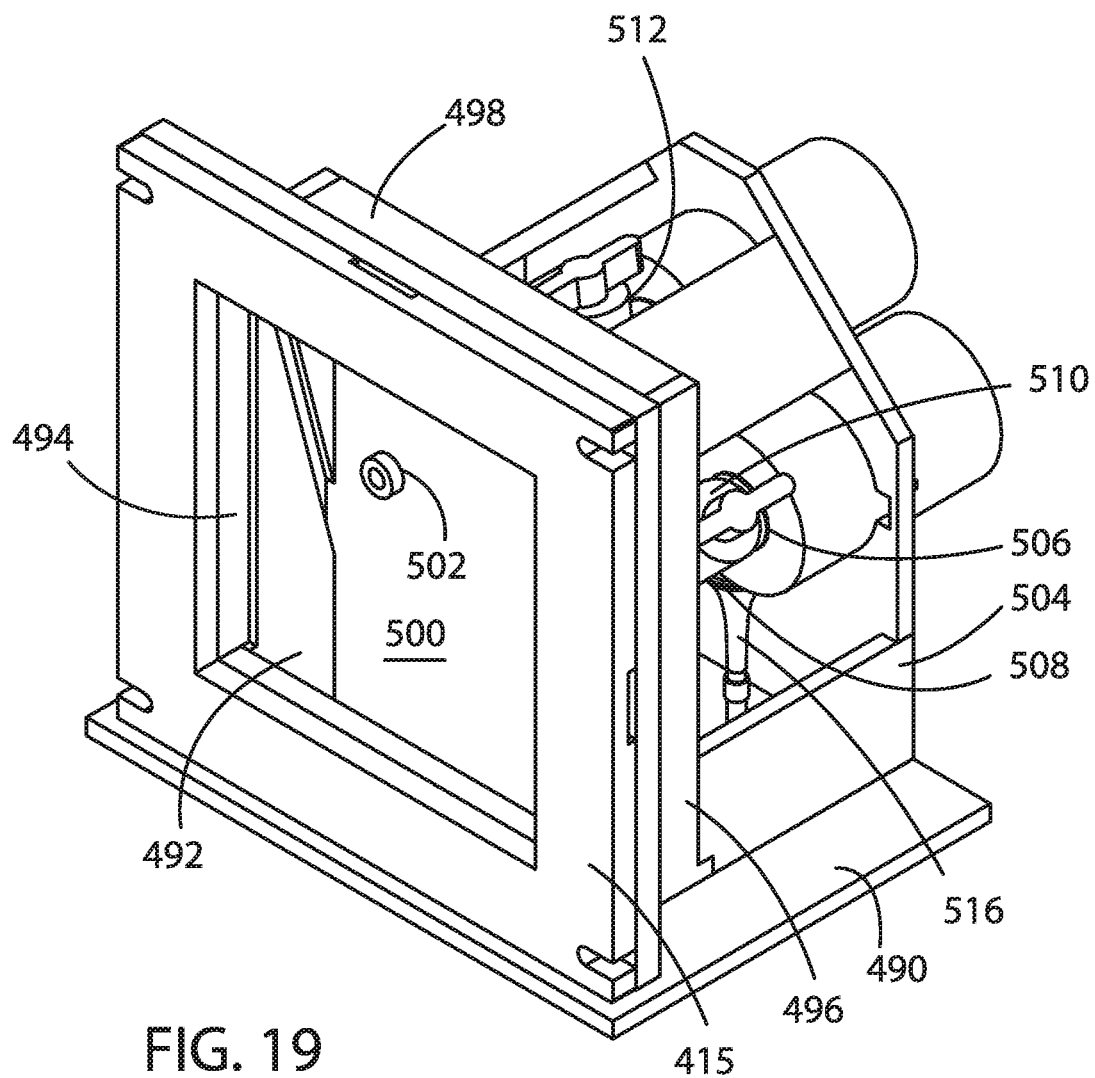
FIG. 19 is a front perspective view of a back plate of a $ClO_2$ sterilization system according to an example embodiment.

Referring primarily to FIGS. 15, 16, and 19, the back plate 415 includes a mounting plate 490 that has substantially the same structure as and functions substantially the same way as the mounting plate 224 of the back plate 215 of fumigant activation unit 200 described above. However, in addition to having an air/gas outlet opening, the mounting plate 490 has additional openings (not shown) adapted to pass air/gas conduits 435, 440, and 445.

The back plate 415 defines an air/gas conduit between the activation chamber 410 and the air/gas outlet opening in the mounting plate 490. The air/gas conduit is structurally and functionally very similar but not identical to the air/gas conduit defined by back plate 215 of fumigant activation unit 200. The air/gas conduit is defined by an air/gas inlet opening 492, opposed vertical side walls 494 and 496, horizontal top wall 498, and vertical back wall 500. The air/gas conduit terminates in the air/gas outlet opening in the mounting plate 490. Unlike the air/gas conduit of back plate 215, the air/gas conduit of back plate 415 does not include a slanted air/gas deflection plate extending from the back wall 500. Also, the back wall 500 of the air/gas conduit includes additional air/gas outlet openings 502 (only one shown) for air/gas to flow from the air/gas conduit.

The back plate 415 of the fumigant activation unit 400 also includes several additional components not present in the back plate 215 of the fumigant activation unit 200. An air/gas blower mounting frame 504 is mounted to the mounting plate 490 and back wall 500 of the back plate 415. Air/gas blowers 455, 456, and 457 are mounted in the mounting frame 504. Each air/gas blower has an air/gas inlet port 506 and an air/gas outlet port 508. The air/gas inlet port 506 of each air/gas blower 455, 456, and 457 is connected to an air/gas outlet 502 of the back plate 415 through an air/gas valve 510, 512, and 514. Each air/gas valve has an air/gas inlet port and an air/gas outlet port connected internally by a passageway, and a valve operable to open and close the passageway to selectively control the flow of air/gas between the inlet and outlet ports. The inlet port of each air/gas valve is connected to an air/gas outlet opening 502 of the back plate via a suitable fitting and/or sealant and the outlet port of each air/gas valve is connected to the air/gas inlet port 506 of an air/gas blower by a suitable fitting. The air/gas outlet port 508 of each air/gas blower is connected by a fitting 516 to a first open end of one of the air/gas conduits 435, 440, 445. The opposite second open ends of the conduits may be connected to an item to be sterilized, such as endoscope 425, enclosed within sealed package 420, as further described below.

The air/gas blower s 435, 440, and 445 preferably are substantially the same as the blowers 9 and 450 described above, e.g., they are sealed, variable speed, DC-powered blowers, such as marine ventilation pumps. Alternatively, as described above, they may be pumps, compressors or the like with similar characteristics. Similarly, the metered water, air bubbling, and air/gas circulation valves 462, 468, and 472 are substantially the same as the valves 234, 238, and 242 described above, e.g. they may be manually controllable or electronically controlled and driven.

Persons skilled in the art will realize that while three air/gas blowers 455, 456, 457 and related conduits 435, 440, 445 and valves 510, 512, 514 are illustrated and described in connection with the example $ClO_2$ sterilization system, more or fewer air/gas blowers, conduits, and valves may be employed depending on the size, nature, and structural characteristics of the item or items to be sterilized and other application specific considerations.

V. Sealable Package and Contents

The package 420 is preferably constructed of a material that is gas impermeable and sturdy enough to withstand normal handling, movement, and storage with an item enclosed without the material breaking or tearing. The material may be transparent, translucent or opaque. Transparency is beneficial for visually observing the enclosed item 425, conduit connections, and the presence of $ClO_2$ fumigant during various phases of the sterilization process. Further, the material preferably is flexible and should be sealable in such a way that the seal is gas impermeable as well. Still further, it is preferred that the material be relatively inexpensive such that it is economical to dispose of a package after use. A suitable material is a flexible sealable plastic, such as the type of material used to make vacuum bags. A package 420 made of the preferred material is suitably formed by molding, extrusion or other processes in various shapes and sizes. Preferably the package 420 is formed with one or more openings to facilitate inserting an item, such as endoscope 425, to be sterilized. The openings can be suitably sealed using RF-welding, thermal sealing, sonic welding or other similar processes. Suitable preformed packages, including flexible vacuum bags, are available from a variety of manufacturers including Saint-Gobain, Grainger, American National Mfg. and others. These preformed packages can be obtained with suitable air/gas ports pre-integrated in the package. The use of such ports is described below.

The package 420 is fitted with a number of air/gas ports (not shown) sufficient to accommodate connections with as many conduits, e.g., conduits 430, 435, 440, and 445 as may be needed. The air/gas ports include check or ball valves, which are gas impermeable when not in use. The air/gas ports and integral valves can be formed integrally with the package 420 when it is manufactured, or may be mounted in openings formed in the package after the package is manufactured so long as the air/gas ports are sealed to be completely gas impermeable when not in use. The gas impermeable characteristic of the air/gas ports ensures that, once sterilized, the item within the package 420 remains sterilized regardless of the subsequent chain of custody, handling, and storage of the package 420 until the package is unsealed.

W. Sealed Enclosure

As briefly indicated above, and as illustrated in FIG. 20, the fumigant activation unit 400 may be interfaced with a sealable enclosure 520 in addition to being directly connected to package 420 and its contents. In this embodiment, the fumigant activation unit 400 is able to sterilize not only the interior and contents of the package 420, but the exterior of the package as well. In addition, although not shown in FIG. 20, an item other than a sealed package and its contents could be placed within the enclosure 520 and sterilized by fumigant activation unit 400.

Fumigant activation unit 400 may be interfaced to an example sealable enclosure 520 via the mounting plate 490 of back plate 415. The mounting plate 490 is mounted to a surface 522 of a main chamber 525 of the enclosure 520 with the air/gas outlet opening in the mounting plate aligned and in sealed air/gas communication with an opening (not shown) in the surface 522 in substantially the same way the mounting plate 224 of fumigant activation unit 200 is interfaced to a surface with an opening as described above. The mounting plate 490 is securely fastened to the surface 522 to affect an air/gas tight seal using suitable fasteners, adhesives, gasket material, and/or other suitable sealant material. Other openings are provided in the surface 522 to allow passage of conduits 430, 435, 440 and 445 if used. These openings also may be sealed using suitable fittings and/or sealant materials when conduits are employed or suitable sealed covers when conduits are not used. Alternatively, the enclosure 520 can be designed such that the fumigant action unit 400 is incorporated as an integral and permanent component of the enclosure.

The main chamber 525 includes one or more sealable ports or hatches 530, 535 for inserting and removing items to be sterilized, such as package 420 and its contents. Sealable ports or hatches 530, 535 may comprise hinged doors 540 or other sealable hatch or port structures capable of providing substantially gas impermeable sealable access to the main chamber 525.

The use of enclosure 520 with fumigant activation unit 400 to sterilize items, including items such as package 420 and other items enclosed therein, such as endoscope 425, is described below. However, persons skilled in the art will realize that because fumigant activation unit 400 is interfaced to the interior of the enclosure 520 not only by conduits 430, 435, 440, and 445, but also via the air/gas outlet opening in the mounting plate 490 of the back plate 415, the fumigant activation unit 400 is adapted to generate and deliver $ClO_2$ fumigant both to the interior and exterior of the package 420 so as to sterilize both the interior and exterior of the package. In addition, items other than package 420 can be enclosed within enclosure 520 and sterilized.

X. Sterilization System Operation and Method

Prior to using the $ClO_2$ sterilization system to sterilize an item within a sealed package, the item to be sterilized preferably is first high level decontaminated. High level decontamination alone is not sufficient to assure the sterility of certain items, especially certain medical instruments, such as endoscopes, which have small openings and passages. It is very difficult for even very extensive high level decontamination processes to eradicate all elements of contamination in the minute openings and passages of such instruments, and it is well known that even one spore that escapes eradication can cause infection. Moreover, repeated high level decontamination processes can result in a build-up of contaminant material making items even harder to adequately clean, let alone be completely decontaminated. However, high level decontamination procedures can be effective to remove relatively larger debris and other contaminants.

After being optionally high level decontaminated, an item to be sterilized is dried and placed inside package 420. If the item to be sterilized has small openings, passages, lumens, and/or other interstices requiring special attention for complete sterilization, like endoscope 425, the ends of as many conduits as are needed, e.g. conduits 435, 440, 445, are connected by fittings 516 to the air/gas outlet ports of one or more air/gas blowers 455, 456, 457. The opposite ends of the conduits are then routed to the interior of the package 420 through air/gas ports (not shown) in the package using suitable fittings and are positioned in or near the openings, passages, etc. of the item requiring special attention.

Similarly, one open end of conduit 430 is connected to the interior of the package 420 via another air/gas port (not shown). The opposite open end of the conduit 430 may be connected to the air/gas inlet port 474 of the air/gas blower 450 of the activator 405 via fitting 476 and/or conduit 478. Alternatively, for reasons which will become apparent, the opposite open end of the conduit may be left exposed in the ambient or connected to an air/gas inlet of another air/gas blower (not shown), the air/gas outlet of which is exposed to the ambient. The package 420 is then sealed with item 425 fully enclosed.

It is important to note that when the fumigant activation unit 400 is interfaced directly to the package 420 and contents 425 thereof, the air/gas outlet opening in the mounting plate 490 of the back plate 415 is sealed closed before initiating a $ClO_2$ gas generating reaction to prevent $ClO_2$ gas from being directed through that air/gas outlet into a space not intended to be sterilized.

A desired amount of a suitable dry reagent, described above, is added to the activation pouch and the activation pouch assembly is positioned within the activation chamber 410 as previously described. The activation chamber 410 and the back plate 415 are sealed closed, also as previously described.

All valves 462, 468, 472, 510, 512, and 514 are initially closed. Valve 462 is opened to add a small amount of water to the activation pouch and then closed. The solution of the water and dry reagents in the activation pouch react to generate essentially pure $ClO_2$ gas. The blower 450 is energized at relatively low speed and the valve 468 in the air bubbler conduit 466 is opened to introduce a relatively low speed air flow into the activation pouch. This agitates the reaction solution, causing it to bubble, thus enhancing the reaction, as previously described.

If desired, the air/gas circulation valve 472 may be opened for the air/gas blower 450 to blow air into the activation chamber 410 through the air/gas circulation inlet opening 480 to entrain the $ClO_2$ gas and help direct the decontamination fumigant to the air/gas outlet openings 502 in the back plate 415. However, this is not necessarily required. The air/gas blowers 455, 456, and 457 are energized and air/gas valves 510, 512, and 514 are opened. The air/gas blowers 455, 456, and 457 draw the decontamination fumigant through the air/gas outlet openings of the back plate through the air/gas valves 510, 512, and 514 and into conduits 435, 440, and 445. The $ClO_2$ fumigant is delivered by the conduits through the air/gas ports in the package 420 into the interior of the package and to the item 425 to be sterilized. The decontamination fumigant enters and circulates through the openings, passages, and other interstices of the item. The air/gas blowers 455, 456, and 457 remain energized and the air/gas valves 510, 512, and 514 remain open for a period of time sufficient for decontamination fumigant to fill the interior of the package 420 with a sufficient volume and concentration of fumigant to completely sterilize the item 425. For an endoscope-sized package, this can usually be accomplished within about 15 minutes. The concentration of the decontamination fumigant within the package 420 can be tested to ensure that the desired concentration has been achieved using Drager tubes inserted through air/gas ports in the package, or with ATI detectors, for example. As previously described, by operating the air/gas blowers at relatively low speeds during this process the production of $ClO_2$ gas is enhanced and the efficacy of the decontamination fumigant is not substantially degraded as it is directed and distributed to the package 420 and enclosed item 425.

The air/gas blowers 455, 456, 457 preferably remain energized and the air/gas valves 510, 512, 514 remain open until the $ClO_2$ gas generating reaction is substantially completed and all or a substantial volume of the resulting decontamination fumigant is distributed to the interior of the package 420 and enclosed item 425. The air/gas blowers may then be de-energized and the valves closed. Alternatively, if the fumigant activation unit is connected in a closed-loop configuration, such as shown in FIG. 15, the air/gas blowers 450, 455, 456, and 457 may continue to run and the valves 472, 510,512, 514 may remain open if it is desired to continuously recirculate the decontamination fumigant between the fumigant activation unit 400 and the interior of the package 420.

The generation of $ClO_2$ gas can be halted at any time by introducing a suitable neutralizing solution, as previously described, into the activation pouch. To do this, the valve 462 in the metered water conduit 460 is closed. The source of metered water is removed from the fitting 464 and replaced by a source of neutralizing solution. The valve 462 is then opened to introduce the neutralizing solution into the activation pouch and then closed again.

As previously described, the amount of water and reagents employed can be varied depending on the desired fumigant concentration and volume, the size/volume of the area to be decontaminated, and the amount of decontamination time desired. In addition, flexible control is maintained over the process even while it is underway. For example, additional water may be added at any time to produce a higher volume or higher concentration of $ClO_2$ gas, or neutralizing solution may be added to discontinue the further generation of $ClO_2$ gas and, if desired, to neutralize the decontamination fumigant already produced.

Typically once the $ClO_2$ generation reaction has completed or been stopped and the decontamination fumigant has been directed to the interior of the package 420, the fumigant is allowed to remain resident within the package for a dwell or residential time sufficient to completely sterilize the item 425 as well as the entire interior of the package 420. For a package sized to enclose an endoscope, for example, a dwell time of approximately 2-3 hours is typically sufficient to accomplish complete sterilization. During this time, the air/gas blowers 450, 455, 456, 457 typically are de-energized and valves 472, 510,512, 514 are closed.

After the desired dwell time has elapsed, the decontamination fumigant is purged from the interior of the package 420. The blower pumps 455, 456, and 457 are de-energized and air/gas valves 510, 512, and 514 are closed. An additional blower (not shown) which is either separate or a part of a central neutralizing area, such as neutralizing area 7 in the example embodiment of FIG. 3, may be used to draw the remaining decontamination fumigant from the interior of the package 420 through the air/gas port and fumigant purge conduit 430 or through another air/gas port in the package (not shown) and conduit (not shown) into the neutralizing area. Alternatively, in some applications the other air/gas blower can be operated to exhaust the remaining fumigant through an air/gas outlet port into the ambient, if appropriate, where the fumigant would be diluted and neutralized by natural factors, such as sunlight.

Also alternatively, or in addition, the fumigant activation unit 400 can be connected in an open-loop configuration with the air/gas inlet 474 exposed in the ambient (if the ambient air is sufficiently clean) or connected to a source of purified air to purge or assist in purging the remaining decontamination from the interior of the package 420. In this configuration, some or all of the air/gas blowers 450, 455, 456 can be energized and air/gas circulation valve 472 and some or all of air/gas valves 510, 512, 514 opened to direct ambient or purified air through the activation chamber 410, back plate 415, and conduits 435, 440, 445 into the interior of the package 420. The ambient or purified air dilutes the remaining fumigant and the air flow helps direct it to the neutralizing area or into the ambient either directly through conduit 430 or another conduit (not shown), or through another air/gas blower and conduit as described above.

Further, alternatively or in addition, the fumigant activation unit 400 can be operated to neutralize or help neutralize the remaining decontamination fumigant while it is directed to a central neutralizing area or into the ambient as described above. To operate the fumigant activation unit in this way, a source of neutralizing solution is connected to the fitting 464 of conduit 460 and valve 462 is opened to add the neutralizing solution to the activation pouch in activation chamber 410. The valve is then closed. The valves and blowers are then operated as described above, except that valve 468 is also opened to introduce bubbling air into the activation pouch. This causes the neutralizing solution in the pouch to bubble and become entrained as a mist in the ambient air flowing through the activation chamber. The air/mist is directed to the interior of the package 420 as described above and thus assists in neutralizing the remaining fumigant as it is directed from the interior of the package to the central neutralizing area or the ambient.

Still further, alternatively or in addition, the fumigant activation unit 400 can be operated to recirculate and neutralize the remaining decontamination fumigant. To do so, the fumigant activation unit is connected in a closed-loop configuration as shown in FIG. 15 and described above. All air/gas blowers 450, 455, 456, 457 are de-energized and all valves 462, 468, 472, 510, 512, 514 are closed. A source of neutralizing solution is connected to the conduit 460 via the fitting 464 and valve 462 is opened to introduce the neutralizing solution into the activation pouch in the activation chamber 410 and then closed. Air/gas blower 450 and some or all of air/gas blowers 455, 456, 457 are energized at a relatively high speed and air/gas valves 472, 510, 512, 514 are opened. This causes the fumigant to recirculate between the interior of the package 420 and the fumigant activation unit 400 through fumigant purge conduit 430 and fumigant delivery conduits 435,440, 445. Air bubbler valve 468 also is opened to cause the neutralizing solution in the activation pouch to bubble. This causes the neutralizing solution to become entrained as a mist in the fumigant as it passes through the activation chamber, thus neutralizing it as it recirculates. The relatively high speed at which the fumigant is recirculated assists in disrupting the $ClO_2$ molecules and facilitates the neutralization process. Additional neutralizing solution can be added to the activation pouch from time to time as needed simply by opening and closing the valve 462. $ClO_2$ sensors may be used at one or more locations in the package, conduits, and fumigant activation unit 400 to detect the remaining concentration of $ClO_2$ fumigant. Once the concentration of $ClO_2$ reaches an acceptable level, the neutralizing operation is complete.

Following the sterilization process, the sealed package 420 may be disconnected from the fumigant purge and delivery conduits 430, 435, 440, and 445. The package may then be handled by different persons, moved between different locations, and stored for lengthy periods of time while maintaining assurance that the enclosed item, e.g. endoscope 425, is completely sterile and will remain completely sterile until the package is opened to retrieve the item for use.

The sequence and method of operation of the fumigant activation unit 400 to sterilize a sealed package 420 and enclosed item 425 are substantially the same when the fumigant activation unit 400 is interfaced to a sealed enclosure 520 as when it is directly connected to the package 420 and item 425 as described above. One difference is that the air/gas opening in the mounting plate 490 of the back plate 415 is not sealed shut. As a result, $ClO_2$ fumigant is directed not only into the interior of the package 420 through conduits 435, 440, and 445, but also into the interior of the sealed enclosure through the air/gas opening in the back plate 415. Accordingly, not only are the interior of the package 420 and enclosed item 425 completely sterilized, but also the exterior of the package. In addition, an additional conduit (not shown) and optionally an additional air/gas blower (not shown) may be used to purge the remaining decontamination fumigant from the interior of the enclosure either to a central neutralizing area or into the ambient similar to the purge process described above.

Y. Compact, Portable Sterilization System and Method for Sterilizing an Item in a Sealed Package FIGS. 21-23 illustrate another example embodiment of a $ClO_2$ sterilization system that is adapted for sterilizing various items contained within sealed packages. Similar to the example embodiments illustrated in FIGS. 15, 16, and 20 and described above, the example sterilization system shown in FIGS. 21-23 is able to provide assurance that an item that has been sterilized will remain completely sterile as long as its sealed package is not opened or otherwise breached. Thus, the item will remain free of contamination despite being handled by various persons, moved between various locations, and stored, even for lengthy periods of time. The example embodiment shown in FIGS. 21-23 has the additional benefit of being highly portable, compact and inexpensive.

The example embodiment of the $ClO_2$ sterilization system comprises a $ClO_2$ fumigant activation unit 550, a sealable bag 575 adapted to contain an item 576 to be sterilized, and air/gas conduits 582, 584 fluidly connecting the activation unit and the bag. The system is designed to comprise a relatively small number of parts and to be readily assembled and disassembled by hand or with readily available hand tools. It is to be understood that while the description of an example embodiment may refer in various locations to a single item to be sterilized, such reference is for ease of description only and a single bag 575 may contain one or multiple items to be sterilized.

The fumigant activation unit 550 comprises an activator housing 552, an air/gas blower 554, and an air/gas conduit 558 connecting the blower and housing. The activator housing 552 comprises an open-top container enclosing an interior volume. The container may be shaped and sized similar to a cup or jar. Other shapes and sizes are also suitable so long as they provide an interior space of sufficient volume. The container is adapted to be selectively attached to and detached from a top enclosure 562. The top enclosure functions to seal closed the container when attached the open top. In one embodiment, the container and top enclosure may be provided with corresponding threads for threaded attachment and detachment. Other attachment/detachment mechanisms may also be used, such as snaps, bayonets, and others, provided the mechanism functions to adequately seal closed the container when it is attached. The container may be made of various materials such as glass, plastic, and other materials that are substantially gas and liquid impermeable and that are substantially chemically inert with respect to reagents employed to generate $ClO_2$ fumigant. The container may be constructed of materials, such as glass or plastic, that are relatively inexpensive and thus may be detached and disposed of following one or more uses if desired.

The activator housing 552 has a first inlet 553, a second inlet 555, and an outlet 557. The first inlet 553 extends through the top enclosure 562 and is adapted to receive and pass an air bubbler tube 564 into the interior volume of the activator housing 552. The air bubbler tube is adapted to deliver a source of air into the activator housing 552 to facilitate a reaction producing $ClO_2$ gas in the same manner as previously described with respect to other embodiments. The second inlet 555 also extends though the top enclosure 562 and is adapted to connect with a valve 560 either directly or via a conduit (not shown). Valve 560 is adapted to receive water from a source external to the activator housing and selectively supply the water into the activator housing (directly or via a conduit) as a reactant to generate $ClO_2$ gas in the same manner as previously described with respect to other embodiments. Preferably, the first and second inlets and the air bubbler tube and valve (or conduit) respectively are connected by suitable fittings and sealed to prevent the unintended escape of $ClO_2$ gas from the interior of the activator housing 552 through the top enclosure 562. The outlet 557 also extends through the top enclosure 562 and is adapted for $ClO_2$ fumigant to exit the interior of the activator housing 552. The outlet 557 is connected to the air/gas conduit 558 preferably by a suitable fitting sealed to prevent the unintended escape of $ClO_2$ fumigant.

The air/gas blower 554 preferably is the same type of air/gas blower as any of the blowers 450, 455, 456, 457 described above in connection with other example embodiments. Thus, the air/gas blower 554 may but need not necessarily be variable speed. It preferably has a motor or drive that runs off batteries or another DC power source to avoid potential ignition risks associated with $ClO_2$ gas. While referred to as a blower, it may be a fan, blower, pump, compressor, or other source capable of providing a suitable flow of air and $ClO_2$ fumigant for the purposes described herein.

The air/gas blower 554 has an inlet 572, a first outlet 568, and optionally a second outlet 570. The inlet 572 connects to the air/gas conduit 558 preferably by a suitable fitting sealed to prevent the unintended escape of $ClO_2$ fumigant. The first outlet 568 connects to an air/gas conduit 582 and is adapted to provide a flow of air and ClO$_2$ fumigant from the fumigant activation unit 550 to the sealable bag 575. The optional second outlet 570 connects to one side of a valve 566. The other side of the valve connects to the air bubbler tube 564 external to the activator housing 552. The second outlet, if used, is adapted to provide a flow of air to the air bubble tube to facilitate a ClO$_2$ gas generating reaction in the activator housing 552 in the same manner as previously described. Alternatively, an air/gas blower with only a single outlet may be used and a source of bubbling air may be tapped off that outlet, preferably controlled by a suitable valve or other type of flow controller. Preferably, the first and second outlets 568, 570 are connected to the air/gas conduit 582 and valve 566 respectively by suitable fittings sealed to prevent the unintended escape of ClO$_2$ fumigant.

If desired, the top enclosure 562 of the activator housing 552 and the air/gas blower 554 may be attached to a mounting platform 556. Although illustrated as a substantially planar plate in the example embodiment, the mounting platform may take a variety of shapes. Preferably, however, the mounting platform will be shaped and sized to facilitate ready portability of the fumigant activation unit 550. In that regard, the mounting platform may be provided with an opening 586, handle, or other facility for easily grasping and carrying the fumigant activation unit. In addition, the fittings and connections used to interconnect the fumigant activation unit to conduits and the like as described above can be types that are readily attached and detached, such as various types of "quick" fittings, so that the fumigant activation unit can be readily disconnected from conduits, sources of power, and the like for ready portability. Alternatively, various fittings and connections may be left attached and the fumigant activation unit may be transported connected to various hoses, conduits and the like, as well as the bag 575.

A pouch 567 is sized to fit within the interior volume of the activator housing 552. The pouch 567 may be essentially the same as the pouch 312 shown and described above in connection with other embodiments. The entire pouch assembly 310 may be used or only the pouch body 312 if desired. Alternatively, a cup like activation cup 13 as shown and described above in connection with other embodiments may be used. In either case, the pouch or cup is adapted to receive and retain the water and reagents that react to generate the ClO$_2$ fumigant in the same manner as described above with respect to other embodiments. Also as previously described, the pouch and cup are constructed to be substantially permeable to gasses, e.g., air and ClO$_2$ fumigant, and substantially impermeable to water and by products of the ClO$_2$ gas generating reaction. Also alternatively, a pouch 567 (or cup) may be omitted altogether. In this alternative, the water and reagents are added directly to the activator housing 552 and react within the housing rather than within the pouch or cup.

The sealable bag 575 functions as a sterility assurance bag and assures that once sterilized an item or items contained within the bag will remain sterile. The sealable bag 575 has one or more openings for introducing the item or items 576 to be sterilized and sufficient interior volume to fully contain and enclose the item or items. The sealable bag has at least one inlet 578, preferably with a self-sealing air/gas port, and at least one outlet 580, also preferably with a self-sealing air/gas port. The inlet 578 connects to one end of the air/gas conduit 582 the other end of which is connected to the first outlet 568 of the air/gas blower 554. The outlet 580 connects to one end of the air/gas conduit 584 the other end of which is connected to the air/gas conduit 558 that is in turn connected between the outlet 557 of the activator housing 552 and the inlet 572 of the air/gas blower 554. Although air/gas conduits 558 and 584 are referred to separately, it is understood that they either may be physically separate hoses/conduits connected by a suitable fitting or sections of a single integral hose/conduit.

The sealable bag 575 may be the same as sealable bag 420 shown and described above with respect to other embodiments. Thus, sealable bag 575 is preferably constructed of a material that is substantially gas impermeable and that is relatively flexible, but sturdy enough to withstand normal handling, movement, and storage with an item enclosed without the material breaking or tearing. The material may be transparent, translucent or opaque depending on the needs of the application. The bag has one or more openings for introducing an item and the openings are sealable via mechanical, thermal, RF, sonic, or other means. The bag also has at least two air/gas ports, preferably one-way ports, which may include check or ball valves, and which are gas impermeable when not in use. Suitable bags are manufactured by Saint-Gobain, Grainger, American National Mfg. and others, and such bags can be obtained with suitable integral air/gas ports.

The sequence and method of operation of the example embodiment shown in FIGS. 21-23 to sterilize an item 576 in a sealed package 575 is similar to what is described above with respect to the example embodiment shown in FIGS. 15-16. However, it is somewhat simplified because the example embodiment of FIGS. 21-23 has fewer components.

Initially, the item or items to be sterilized 576 are placed inside the sealable bag 575 and the bag is sealed. The air/gas conduits 582 and 584 are connected to the inlet 578 and outlet 580 of the bag 575 respectively. Air/gas conduit 582 is also connected to the first outlet 568 of the air/gas blower 554. Air/gas conduit 584 is also connected to the outlet 557 of the activator housing 552 and the inlet 572 of the air/gas blower 554 as shown in FIGS. 21-23. This results in a closed-loop air/gas circulation system between the activator housing 552, air/gas blower 554, and interior of the sealed bag 575. The activator housing 552 is detached from the top enclosure 562. A desired amount of reagent suitable for generating ClO$_2$ fumigant is added to the pouch 567, if it is being used, and the pouch is placed in the activator housing. Otherwise, the reagent is added directly to the activator housing. A suitable reagent is the same as described above with respect to other embodiments, e.g., a dry effervescent tablet comprising sodium chlorite and sodium dichloroisocyanurate dihydrate, which is available from a variety of sources. The amount of reagent used will vary with the volume of the bag, the size, shape and characteristics of the item to be sterilized, and the degree of sterilization desired. The activator housing 552 is then re-attached and sealed to the top enclosure 562.

The valves 560 and 566 are initially closed. A source of water, such as a metered syringe (not shown) is connected to valve 560 and valve 560 is opened to introduce the water into the pouch 567, if one is being used, or into the activator housing 552. The valve 560 is then closed. The reaction solution of the water and dry reagent in the pouch 567 or the activator housing 552 generates essentially pure ClO$_2$ gas. The air/gas blower 554 is activated and, if desired, the valve 566 is opened to introduce a relatively low speed air flow through the bubbler tube 564 into the pouch or activator housing to agitate or bubble the reaction solution and enhance the reaction as previously described. The valve 566 may remain open or may be closed as desired at any time during the process.

With the air/gas blower 554 activated, a flow of air is created in the closed circulation loop from the first outlet 568 of the air/gas blower 554 to the interior of the sealed bag 575 through the bag inlet 578, through the interior volume of the bag, out through the bag outlet 580, through the activator housing 552 via the outlet 557, and into the inlet 572 of the air/gas blower 554. As essentially pure $ClO_2$ gas is generated in the activator housing, it is entrained in the air flow as a fumigant which is directed to the interior volume of the bag 575 to sterilize the item or items 576. The air/gas blower preferably remains energized for a period of time sufficient for the fumigant to fill the interior of the bag 575 with a sufficient volume and concentration of fumigant to sterilize the item or items 576. For a relatively small item, such as a typical endoscope, and a corresponding sized bag this can usually be accomplished within about 15 minutes. As described previously, the concentration of the decontamination fumigant within the bag can be tested using a suitable sensor if desired to ensure that the desired concentration has been achieved. Also as previously described, by operating the air/gas blower 554 at a relatively low speed during this process the production of $ClO_2$ gas is enhanced and the efficacy of the decontamination fumigant is not substantially degraded as it is directed and distributed to the interior of the bag.

Once a sufficient volume and concentration of fumigant is present in the bag, the air/gas blower 554 may be de-energized and the fumigant is allowed to remain in the bag for a dwell or residence time sufficient to achieve the desired degree of sterilization of the item or items 576. It is noted that some of the fumigant will also be retained within the closed-loop, however if the closed-loop is effectively sealed there should be no substantial leakage of fumigant and no substantial effect on sterilization of the item or items 576. The dwell time will depend on the size and characteristics of the items 576, the interior volume of the bag 575, and the concentration of the fumigant generated. However, for a relatively small item, such as a typical endoscope, and a corresponding sized bag, a dwell time of approximately 2-3 hours typically would be sufficient to accomplish complete sterilization.

Alternatively, if desired, the air/gas blower 554 may remain energized for part or all of the dwell time and continue to circulate fumigant through the interior of the bag 575. Such operation may facilitate effective sterilization of certain items, such as items with small openings and internal passages.

As described above in connection with other embodiments, the generation of $ClO_2$ gas can be halted at any time by introducing a suitable neutralizing solution, as previously described, into the activation pouch or activator housing 552. To do this, the water source connected to the valve 560 is replaced by a source of neutralizing solution, the valve is opened and the neutralizing solution is introduced into the pouch 567 or activator housing 552. The valve is then closed.

As previously described, the amount of water and reagents employed can be varied depending on the desired fumigant concentration and volume, the size/volume of the area to be decontaminated, and the amount of decontamination time desired. In addition, flexible control is maintained over the process even while it is underway. For example, additional water may be added at any time to produce a higher volume or higher concentration of $ClO_2$ gas, or neutralizing solution may be added to discontinue the further generation of $ClO_2$ gas and, if desired, to neutralize the decontamination fumigant already produced.

After the desired dwell time has elapsed, the decontamination fumigant can be neutralized if desired by adding neutralizing solution as described, activating the air/gas blower 554 and circulating the fumigant through the closed loop. As it circulates through the activator housing 552, the fumigant is exposed to the neutralizing solution, which is also entrained in the flow. The fumigant can be circulated for a period of time sufficient to reduce the concentration of $ClO_2$ gas to a level at which it is safe to release. As previously described, the concentration can be tested using a suitable sensor to determine when a desired concentration level is reached.

Once a safe concentration level is reached, the neutralized fumigant may be purged from the bag 575. Alternatively, in some environments, it may be safe to release even un-neutralized fumigant into the ambient environment. For example, it is known that $ClO_2$ gas is diluted and degrades relatively rapidly in a sunlit open space. Accordingly, releasing the fumigant in such an environment may be acceptable even without neutralization. Whether or not neutralized, any fumigant remaining in the bag 575 after the sterilization process is complete may be purged from the bag using the air/gas blower 554 by disconnecting air/gas conduit 582 from the bag inlet 578, leaving air/gas conduit 584 connected to the bag outlet 580, and activating air/gas blower 554. Also alternatively if desired an additional blower (not shown) may be connected to the outlet 580 of the sealed bag 575 and used to draw out remaining fumigant.

After the sealed bag 575 is purged, the fumigant activation unit 550 may be disconnected from the bag. Although it is preferred that the first inlet 578 and first outlet 580 of the bag include self-sealing valves to prevent any entry of unwanted air or gas into the bag once the air flow in the closed loop is discontinued, if necessary the inlet 578 and outlet 580 can be otherwise sealed.

After the fumigant activation unit 550 is disconnected from the sealed bag 575, the bag functions as a sterility assurance bag and may be handled by different persons, moved between different locations, and stored for lengthy periods of time while maintaining assurance that the enclosed item or items 576 are completely sterile and will remain completely sterile until the bag is opened to retrieve the item. The bag may then be disposed of.

In addition, the activator housing 552 may be detached from the top enclosure 562 and the activator housing and the pouch (if used) may be disposed of if desired. The fumigant activation unit 550 may be easily carried to another location and prepared for use there in the manner described above.

It is expressly contemplated that each of the various aspects, embodiments, and features thereof described herein may be freely combined with any or all other aspects, embodiments, and features. The resulting aspects and embodiments (e.g., products and methods) are within the scope of the invention. It should be understood that headings herein are provided for purposes of convenience and do not imply any limitation on content included below such heading or the use of such content in combination with content included below other headings. Unless otherwise defined, all technical and scientific terms used herein have the same meaning as commonly understood by one of ordinary skill in the art to which this invention belongs.

All articles, books, patent applications, patents, other publications mentioned in this application are incorporated herein by reference. In the event of a conflict between the specification and any of the incorporated references the specification (including any amendments thereto) shall control. Unless otherwise indicated, art-accepted meanings of terms and abbreviations are used herein.

In the claims articles such as "a", "an" and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. It is to be understood that the invention encompasses all variations, combinations, and permutations in which one or more limitations, elements, clauses, descriptive terms, etc., from one or more of the listed claims is introduced into another claim. For example, any claim that is dependent on another claim may be modified to include one or more elements, limitations, clauses, or descriptive terms, found in any other claim that is dependent on the same base claim. Furthermore, where the claims recite a product, it is to be understood that methods of using the product according to any of the methods disclosed herein, and methods of making the product, are included within the scope of the invention, unless otherwise indicated or unless it would be evident to one of ordinary skill in the art that a contradiction or inconsistency would arise.

Where elements are presented as lists, it is to be understood that each subgroup of the elements is also disclosed, and any element(s) may be removed from the group. The invention provides all such embodiments.

The terms "approximately" or "about" in reference to a number generally include numbers that fall within ±10%, in some embodiments ±5%, in some embodiments ±1%, in some embodiments ±0.5% of the number unless otherwise stated or otherwise evident from the context (except where such number would impermissibly exceed 100% of a possible value). Where ranges are given, endpoints are included. Furthermore, it is to be understood that unless otherwise indicated or otherwise evident from the context and understanding of one of ordinary skill in the art, values that are expressed as ranges may assume any specific value or subrange within the stated ranges in different embodiments of the invention, to the tenth of the unit of the lower limit of the range, unless the context clearly dictates otherwise. Any one or more embodiment(s), element(s), feature(s), aspect(s), component(s) etc., of the present invention may be explicitly excluded from any one or more of the claims.

Those skilled in the art will recognize, or be able to ascertain using no more than routine experimentation, many equivalents to the specific embodiments of the invention described and exemplified herein. The scope of the present invention is not intended to be limited to the above Description and Examples, but rather is as set forth in the appended claims.

What is claimed is:

1. A sterilization system for sterilizing an item, comprising:
   an activator housing adapted to receive water and reagent for generating $ClO_2$ fumigant, wherein the activator housing has an air/gas outlet;
   an air/gas blower having an air/gas inlet and a first air/gas outlet, wherein the air/gas inlet is in fluid communication with the air/gas outlet of the activator housing;
   a sealable package adapted to contain the item to be sterilized and having an air/gas inlet and an air/gas outlet, wherein the air/gas inlet is in fluid communication with the first air/gas outlet of the air/gas blower and the air/gas outlet is in fluid communication with the air/gas outlet of the activator housing;
   an activator housing top enclosure adapted to seal closed the activator housing; and
   a portable mounting platform;
   wherein the activator housing top enclosure and the air gas blower are mounted to the portable mounting platform;
   wherein the activator housing has an open top that is adapted to receive the water and reagents, and that is detachably connectable to the activator housing top enclosure; and
   wherein the air/gas blower is selectively operable to direct $ClO_2$ fumigant generated in the activator housing through a closed circulation loop between the activator housing and the sealable package to sterilize the item.

2. The sterilization system of claim 1, wherein the activator housing is disposable.

3. The sterilization system of claim 1, comprising:
   a first valve; and
   a first inlet in the activator housing top enclosure;
   wherein the first inlet in the activator housing top enclosure is in fluid communication with the first valve;
   wherein the first valve is mounted to the portable mounting platform and is adapted for removable attachment with a source of water; and
   wherein the first valve is operable to selectively introduce water into the activator housing through the first inlet in the activator housing top enclosure.

4. The sterilization system of claim 3, comprising:
   a second valve;
   a second inlet in the activator housing top enclosure; and
   the air gas/blower having a second air/gas outlet;
   wherein the second inlet in the activator housing top enclosure is in fluid communication with the second valve;
   wherein the second valve is mounted to the portable mounting platform and is in fluid communication with the second air/gas outlet of the air/gas blower; and
   wherein the second valve is operable to selectively introduce a flow of bubbling air from the second air/gas outlet of the air/gas blower into the activator housing though the second inlet in the activator housing top enclosure.

5. The sterilization system of claim 1, comprising an activation pouch, wherein the activation pouch is:
   adapted to reside within the activator housing and to receive the water and reagents; and
   substantially permeable to air and gas and substantially impermeable to liquid and $ClO_2$ fumigant generating reaction by-products.

6. The sterilization system of claim 1, wherein the package comprises a substantially flexible gas impermeable material, wherein the material contains at least one opening adapted to receive the item to be sterilized and encloses an interior space adapted to contain the item, and wherein the at least one opening is adapted to be sealed closed, whereby upon the item being sterilized the package assures the item will remain sterilized.

7. The sterilization system of claim 1, wherein:
   the air/gas inlet of the package is detachably connected to the first air/gas outlet of the air/gas blower by a first air/gas conduit; and the air/gas outlet of the package is detachably connected to the air/gas outlet of the activator housing and the air/gas inlet of the air/gas blower by a second air/gas conduit.

8. The sterilization system of claim 1, wherein the air/gas inlet and the air/gas outlet of the package comprise self-sealing air/gas valves.

9. The sterilization system of claim 1, wherein the package is disposable.

10. A method of sterilizing an item using the sterilization system recited in claim 1, comprising:
    detachably connecting the open top of the activator housing containing the reagent to the activator housing top enclosure;
    inserting the item to be sterilized in the package and sealing the package closed;
    introducing water into the activator housing to produce $ClO_2$ fumigant; and
    activating the air/gas blower direct the $ClO_2$ fumigant to the package to sterilize the item.

11. The method of claim 10, comprising:
    transporting the mobile mounting platform to a selected location where the package is located prior to introducing water into the activator housing;
    deactivating the air/gas blower after a selected period of time; and
    transporting the mobile mounting platform from the selected location.

12. A sterilization system for sterilizing an item, comprising:
    an activator housing having an opening adapted to receive water and reagent for generating $ClO_2$ fumigant, wherein the activator housing has an air/gas outlet;
    an air/gas blower having an air/gas inlet and an air/gas outlet, wherein the air/gas inlet is in fluid communication with the air/gas outlet of the activator housing;
    a sealable package adapted to contain the item to be sterilized and having an air/gas inlet and an air/gas outlet, wherein the air/gas inlet is in fluid communication with the air/gas outlet of the air/gas blower and the air/gas outlet is in fluid communication with the air/gas outlet of the activator housing; and
    a portable mounting platform;
    an activator housing top enclosure, wherein the activator housing top enclosure is mounted to the portable mounting platform;
    wherein the activator housing is selectively detachable from the activator housing top enclosure to receive the reagent and is selectively connectable to the portable mounting platform to generate the $ClO_2$ fumigant, wherein the air/gas blower is mounted to the portable mounting platform; and
    wherein the air/gas blower is selectively operable to direct the $ClO_2$ fumigant generated in the activator housing through a closed circulation loop between the activator housing and the package to sterilize the item.

13. The sterilization system of claim 12, wherein the activator housing is disposable.

14. The sterilization system of claim 12, wherein the activator housing top enclosure is adapted to detachably connect to the activator housing and to seal the opening of the activator housing.

15. The sterilization system of claim 12, wherein the activator housing top enclosure comprises an inlet adapted to receive water and to introduce the water into the activator housing.

16. The sterilization system of claim 12, wherein the activator housing top enclosure comprises an inlet adapted to receive a flow of bubbling air from the air/gas blower and to introduce the flow of bubbling air into the activator housing.

17. The sterilization system of claim 12, comprising an activation pouch, wherein the activation pouch is adapted to reside within the activator housing and to receive the water and reagent, and is substantially permeable to air and gas and substantially impermeable to liquid and $ClO_2$ fumigant generating reaction by-products.

18. The sterilization system of claim 12, wherein the sealable package is disposable.

19. The sterilization system of claim 12, wherein the sealable package comprises a substantially flexible gas impermeable material with an interior space, wherein the sealable package contains at least one opening adapted to receive the item in the interior space, and wherein the at least one opening is adapted to be sealed to retain the item in the sealable package.

20. The sterilization system of claim 12, wherein the sealable package comprises an inlet with a self-sealing valve and an outlet with a self-sealing valve, and wherein the inlet of the sealable package is in fluid communication with the outlet of the air/gas blower and the outlet of the sealable package is in fluid communication with the activator housing to form the closed circulation loop.

* * * * *